(12) United States Patent
Paez-Pereda et al.

(10) Patent No.: US 8,153,127 B2
(45) Date of Patent: Apr. 10, 2012

(54) METHOD OF TREATING DEPRESSION

(75) Inventors: Marcelo Paez-Pereda, Munich (DE); Marta Labeur, München (DE)

(73) Assignees: PhenoQuest AG, Martinsried (DE); Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 93 days.

(21) Appl. No.: 12/278,023

(22) PCT Filed: Feb. 7, 2007

(86) PCT No.: PCT/EP2007/001044
§ 371 (c)(1),
(2), (4) Date: Aug. 21, 2008

(87) PCT Pub. No.: WO2007/090631
PCT Pub. Date: Aug. 16, 2007

(65) Prior Publication Data
US 2010/0069463 A1    Mar. 18, 2010

(30) Foreign Application Priority Data
Feb. 7, 2006 (EP) .................................. 06002474

(51) Int. Cl.
*A61K 39/395* (2006.01)
*A61K 39/40* (2006.01)
*A61K 39/42* (2006.01)
*A01N 61/00* (2006.01)

(52) U.S. Cl. ............... 424/139.1; 424/130.1; 424/145.1; 514/17.5; 514/17.6

(58) Field of Classification Search .................. None
See application file for complete search history.

(56) References Cited

U.S. PATENT DOCUMENTS

2005/0209181 A1   9/2005   Akil et al.
2005/0276812 A1  12/2005   Ebens et al.

FOREIGN PATENT DOCUMENTS

WO   WO 2005/117986   12/2005

OTHER PUBLICATIONS

International Search Report for International Application No. PCT/EP2007/001044 dated Jun. 19, 2007 (5 pgs.).
Paez-Pereda et al., "New drug targets in the signaling pathways activated by antidepressants". *Progress in Neuro-Psychopharmacology & Biological Psychiatry*, vol. 29, No. 6, Jul. 2005, pp. 1010-1616.
Paez-Pereda et al., "Cushing's syndrome: Drug targets and therapeutic options", *Expert Opinion on Therapeutic Patentts* Oct. 1, 2002, vol. 12, No. 10, Oct. 2002, pp. 1537-1546.
American Psychiatric Association: *Diagnostic and Statistical Manual of Mental Disorders*, Fourth Edition, Text Revision. Washington, DC, American Psychiatric Associate, 2000.
Bohula et al. "Targeting the type 1 insulin-like growth factor receptor as anti-cancer treatment" *Anti-Cancer Drugs* 14: 669-682 (2003).
Surmacz E. "Growth factor receptors as therapeutic targets: strategies to inhibit the insulin-like growth factor I receptor" *Oncogene* 22(42):6589-6597 (2003).
Stein et al. "Neutralization of transthyretin reverses the neuroprotective effects of secreted amyloid precursor protein (APP) in APPSW mice resulting in tau phosphorylation and loss of hippocampal neurons: support for the amyloid hypothesis" *J Neurosci* 24:7707-7717 (2004).
Bard et al. "Peripherally administered antibodies against amyloid beta-peptide enter the central nervous system and reduce pathology in a mouse model of Alzheimer disease" *Nat Med* 6: 916-919 (2000).
"Safety and Tolerability Study in Patients With Mild to Moderate Alzheimer's Disease (AD)" Clinical Trial. Summary obtained from *ClinicalTrails.gov* accessed Nov. 14, 2011.
"Phase II Study of Intravenous Immunoglobulin (IVIg) for Alzheimer's Disease" Clinical Trial. Summary obtained from *ClinicalTrails.gov* accessed Nov. 14, 2011.
"Safety Study of Passive Immunization for Patients With Mild to Moderate Alzheimer's Disease" Clinical Trial. Summary obtained from *ClinicalTrials.gov* accessed Nov. 14, 2011.
Miller et al. "Targeting Alzheimer's disease genes with RNA interference: an efficient strategy for silencing mutant alleles" *Nucleic Acids Res* 32(2):661-668 (2004).
Lucki et al. "Sensitivity to the effects of pharmacologically selective antidepressants in different strains of mice" *Psychopharmacology*; 155:315-22 (2001).
Hoyer et al, "Global down-regulation of gene expression in the brain using RNA interference, with emphasis on monoamine transporters and GPCRs: implications for target characterization in psychiatric and neurological disorders" *J Recept Signal Transduct Res* 26:527-47 (2006). Allgulander C, Sheehan DV "Generalized anxiety disorder: raising the expectations of treatment" *Psychopharmacol Bull.* 36 Suppl 2:68-78 (2002).
Banks et al. "Anti-Amyloid Beta Protein Antibody Passage Across the Blood-Brain Barrier in the SAMP8 Mouse Model of Alzheimer's Disease: An Age-related Selective Uptake with Reversal of Learning Impairment", *Exp Neurol.* Aug. 2007; 206(2): 248-256 (2007).
Bourin et al., "Augmentation effect of combination therapy of aripiprazole andantidepressants on forced swimming test in mice.", *Psychopharmacology* 206:97-107 (2009).
Can et al., "Antidepressant-like responses to lithium in genetically diverse mouse strains" , *Genes Brain Behav* 10:434-43 (2001).
Cañive et al. "Bupropion treatment in veterans with posttraumatic stress disorder: an open study." *J Clin Psychopharmacol.* 18(5):379-83 (1998).

(Continued)

*Primary Examiner* — Olga N Chernyshev
(74) *Attorney, Agent, or Firm* — Foley & Lardner LLP

(57) ABSTRACT

The present invention relates to a method for identifying a TMEFF2 modulator, comprising (a) contacting a cell which expresses TMEFF2 with a candidate compound to be tested; (b) measuring whether said compound to be tested decreases or increases the level of a constituent of the cAMP signalling pathway, preferably the CRH signalling pathway, in said cell when compared to a corresponding cell which does not express TMEFF2; (b') optionally determining whether said compound is capable of reduncing the binding between Activin and TMEFF2; and (c) identifying said modulator compound. Furthermore, a method for identifying a TMEFF2 modulator comprising determining whether said TMEFF2 modulator is capable of reducing the binding between Activin and TMEFF2 is contemplated. It also relates to uses and methods applying a TMEFF2 agonist for the treatment of Cushing's Syndromes and a TMEFF2 modulator for the treatment of affective disorders. Furthermore, methods of diagnosing affective disorders or Cushing's Syndromes are provided.

3 Claims, 22 Drawing Sheets

OTHER PUBLICATIONS

Figure 1:
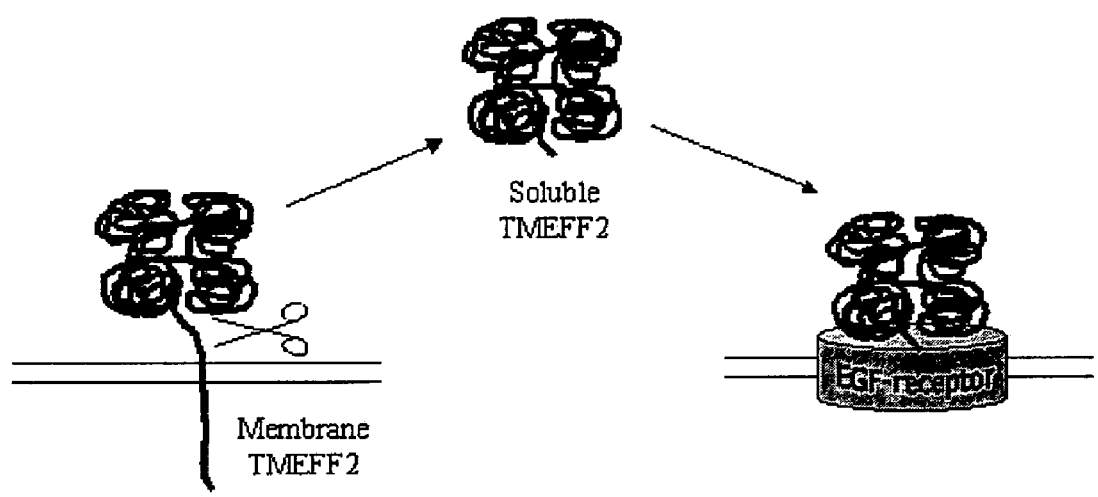

Cekinović et al; "Passive Immunization Reduces Murine Cytomegalovirus-Induced Brain Pathology in Newborn Mice," *J. Virol.* Dec. 2008, vol. 82, No. 24, p. 12172-12180 (2008).

Dhir and Kulkarni, "Risperidone, an atypical antipsychotic enhances the antidepressant-like effect of venlafaxine or fluoxetine: Possible involvement of alpha-2 adrenergic receptors", *Neurosci Lett* 445:83-8 (2008).

Erfurth et al. "Bupropion as add-on strategy in difficult-to-treat bipolar depressive patients" *Neuropsychobiology* 45 Suppl 1:33-6 (2002).

Frieden "Characterization, receptor mapping and blood-brain barrier transcytosis of antibodies to the human transferrin receptor", *J. Pharmacology Expt Therapeutics*, 278(3) 1491-1498 (1996).

Gottfries CG, Karlsson I, Nyth AL. "Treatment of depression in elderly patients with and without dementia disorders", *Int Clin Psychopharmacol.* 6 Suppl 5:55-64. (1992).

Jiao et al., "Antidepressant response to chronic citalopram treatment in eight inbred mouse strains", *Psychopharmacology* 213:509-20 (2011).

Pawar et al., "Evaluation of antidepressant like property of amisulpride per se and its comparison with fluoxetine and olanzapine using forced swimming test in albino mice", *Acta Pol Pharm* 66:327-31 (2009).

Porsolt et al., "Behavioural Despair in Mice: A Primary Screening Test for Antidepressants", *Arch Int Pharmacodyn Ther* 229:327-36 (1977).

Sanchez et al., "Escitalopram, the S-(+)-enantiomer of citalopram, is a selective serotonin reuptake inhibitor with potent effects in animal models predictive of antidepressant and anxiolytic activities", Psychopharmacology 167:353-62 (2003).

Sarkisyan et al., "The 5-HT7 receptor as a mediator and modulator of antidepressant-like behavior", *Behav Brain Res* 209:99-108 (2010).

Silver et al. "Multifunctional pharmacotherapy: what can we learn from study of selective serotonin reuptake inhibitor augmentation of antipsychotics in negative-symptom schizophrenia?" *Neurotherapeutics* 6(1):86-93 (2009).

Tsuchida et al, "Activin signaling as an emerging target for therapeutic interventions", *Cell Commun Signal* 18:7-15 (2009).

Vaidya et al, "Depression—emerging insights from Neurobiology", *Br Med Bull* 57:61-79 (2001).

ver der Loos ML et al "Long-term outcome of bipolar depressed patients receiving lamotrigine as add-on to lithium with the possibility of the addition of paroxetine in nonresponders: a randomized, placebo-controlled trial with a novel design" *Bipolar Disord.* 13(1):111-7 (2011).

Young et al., "GBR 12909 administration as a mouse model of bipolar disorder mania: mimicking quantitative assessment of manic behavior", *Psychopharmacology* 208:443-54 (2010).

Zisook et al. "Citalopram augmentation for subsyndromal symptoms of depression in middle-aged and older outpatients with schizophrenia and schizoaffective disorder: a randomized controlled trial." *J Clin Psychiatry.* 70(4):562-71. (2009).

pCMV: cytomegalovirus promoter
T7: T7 polymerase promoter

Figure 16

Human TMEFF2 nucleotide sequence (cDNA) [SEQ ID NO: 1]

```
   1 cagtagcccg ctgcccggcc cccgcgatcc tgtgttcctc ggaagccgtt tgctgctgca
  61 gagttgcacg aactagtcat ggtgctgtgg gagtccccgc ggcagtgcag cagctggaca
 121 ctttgcgagg gcttttgctg gctgctgctg ctgcccgtca tgctactcat cgtagcccgc
 181 ccggtgaagc tcgctgcttt ccctacctcc ttaagtgact gccaaacgcc caccggctgg
 241 aattgctctg gttatgatga cagagaaaat gatctcttcc tctgtgacac caacacctgt
 301 aaatttgatg gggaatgttt aagaattgga gacactgtga cttgcgtctg tcagttcaag
 361 tgcaacaatg actatgtgcc tgtgtgtggc tccaatgggg agagctacca gaatgagtgt
 421 tacctgcgac aggctgcatg caaacagcag agtgagatac ttgtggtgtc agaaggatca
 481 tgtgccacag atgcaggatc aggatctgga gatggagtcc atgaaggctc tggagaaact
 541 agtcaaaagg agacatccac ctgtgatatt tgccagtttg gtgcagaatg tgacgaagat
 601 gccgaggatg tctggtgtgt gtgtaatatt gactgttctc aaaccaactc caatccctc
 661 tgcgcttctg atgggaaatc ttatgataat gcatgccaaa tcaaagaagc atcgtgtcag
 721 aaacaggaga aaattgaagt catgtctttg ggtcgatgtc aagataacac aactacaact
 781 actaagtctg aagatgggca ttatgcaaga acagattatg cagagaatgc taacaaatta
 841 gaagaaagtg ccagagaaca ccacatacct tgtccggaac attacaatgg cttctgcatg
 901 catgggaagt gtgagcattc tatcaatatg caggagccat cttgcaggtg tgatgctggt
 961 tatactggac aacactgtga aaaaaggac tacagtgttc tatacgttgt tcccggtcct
1021 gtacgatttc agtatgtctt aatcgcagct gtgattggaa caattcagat tgctgtcatc
1081 tgtgtggtgg tcctctgcat cacaaggaaa tgccccagaa gcaacagaat tcacagacag
1141 aagcaaaata cagggcactg tgggtataat actaagttga gatgatatca tttacggggg
1201 aaggcgcttt gtgaagtagg ccttatttct cttgtccttt cgtacaggga ggaatttgaa
1261 gtagatagaa accgacctgg attactccgg tctgaactca gatcacgtag gactttaatc
1321 gttgaacaaa cgaacccttta atagcggctg caccatcggg atgtcctgat ccaacatcga
1381 ggtcgtaaac cctattgttg atatggactc tagaatagga ttgcgctgtt atccctaggg
1441 taacttgttc cgttggtcaa gttattggat caattgagta tagtagttcg ctttgactgg
1501 tgaagtctta gcatgtactg ctcggaggtt gggttctgct ccgaggtcgc cccaaccgaa
1561 atttttaatg caggtttggt agtttaggac ctgtgggttt gttaggtact gtttgcatta
1621 ataaatt
```

(the coding sequence is shown in bold type)

Human TMEFF2 amino acid sequence [SEQ ID NO: 2]

```
MVLWESPRQC SSWTLCEGFC WLLLLPVMLL IVARPVKLAA FPTSLSDCQT
PTGWNCSGYD DRENDLFLCD TNTCKFDGEC LRIGDTVTCV CQFKCNNDYV
PVCGSNGESY QNECYLRQAA CKQQSEILVV SEGSCATDAG SGSGDGVHEG
SGETSQKETS TCDICQFGAE CDEDAEDVWC VCNIDCSQTN FNPLCASDGK
SYDNACQIKE ASCQKQEKIE VMSLGRCQDN TTTTTKSEDG HYARTDYAEN
ANKLEESARE HHIPCPEHYN GFCMHGKCEH SINMQEPSCR CDAGYTGQHC
EKKDYSVLYV VPGPVRFQYV LIAAVIGTIQ IAVICVVVLC ITRKCPRSNR
IHRQKQNTGH CGYNTKLR
```

Figure 20
FST1
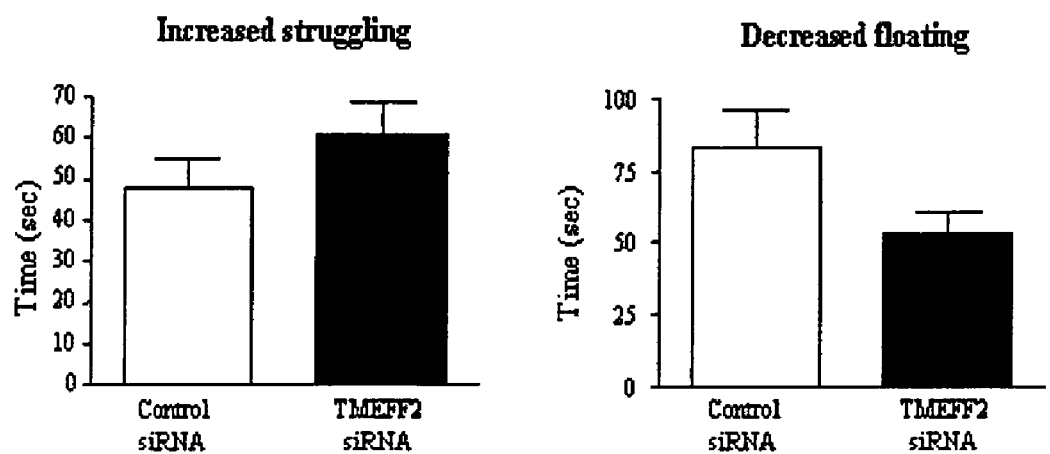
FST2
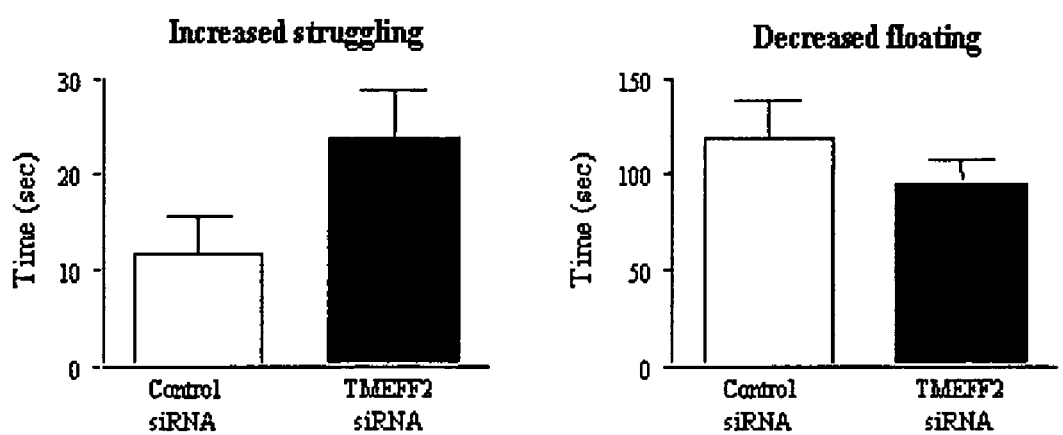

Figure 22

Human Activin (Inhibin beta A) nucleotide sequence (cDNA) [SEQ ID NO: 18]

```
   1 agtacagtat aaaacttcac agtgccaata ccatgaagag gagctcagac agctcttacc
  61 acatgataca agagccggct ggtggaagag tggggaccag aaagagaatt tgctgaagag
 121 gagaaggaaa aaaaaaacac caaaaaaaaa aataaaaaaa tccacacaca caaaaaaacc
 181 tgcgcgtgag gggggaggaa aagcagggcc ttttaaaaag gcaatcacaa caacttttgc
 241 tgccaggatg cccttgcttt ggctgagagg atttctgttg gcaagttgct ggattatagt
 301 gaggagttcc cccaccccag gatccgaggg gcacagcgcg gcccccgact gtccgtcctg
 361 tgcgctggcc gccctcccaa aggatgtacc caactctcag ccagagatgg tggaggccgt
 421 caagaagcac attttaaaca tgctgcactt gaagaagaga cccgatgtca cccagccggt
 481 acccaaggcg gcgcttctga acgcgatcag aaagcttcat gtgggcaaag tcggggagaa
 541 cgggtatgtg gagatagagg atgacattgg aaggagggca gaaatgaatg aacttatgga
 601 gcagacctcg gagatcatca cgtttgccga gtcaggaaca gccaggaaga cgctgcactt
 661 cgagatttcc aaggaaggca gtgacctgtc agtggtggag cgtgcagaag tctggctctt
 721 cctaaaagtc cccaaggcca acaggaccag gaccaaagtc accatccgcc tcttccagca
 781 gcagaagcac ccgcagggca gcttggacac aggggaagag gccgaggaag tgggcttaaa
 841 gggggagagg agtgaactgt tgctctctga aaaagtagta gacgctcgga gagcacctg
 901 gcatgtcttc cctgtctcca gcagcatcca gcggttgctg gaccagggca gagctccct
 961 ggacgttcgg attgcctgtg agcagtgcca ggagagtggc gccagcttgg ttctcctggg
1021 caagaagaag aagaaagaag aggaggggga agggaaaaag aagggcggag gtgaaggtgg
1081 ggcaggagca gatgaggaaa aggagcagtc gcacagacct ttcctcatgc tgcaggcccg
1141 gcagtctgaa gaccaccctc atcgccggcg tcggcgggga ttggagtgtg atggcaaggt
1201 caacatctgc tgtaagaaac agttctttgt cagtttcaag gacatcggct ggaatgactg
1261 gatcattgct ccctctggct atcatgccaa ctactgcgag ggtgagtgcc cgagccatat
1321 agcaggcacg tccgggtcct cactgtcctt ccactcaaca gtcatcaacc actaccgcat
1381 gcggggccat agcccctttg ccaacctcaa atcgtgctgt gtgcccacca gctgagacc
1441 catgtccatg ttgtactatg atgatggtca aacatcatc aaaaaggaca ttcagaacat
1501 gatcgtggag gagtgtgggt gctcatagag ttgcccagcc caggggaaa gggagcaaga
1561 gttgtccaga gaagacagtg gcaaatgaa gaaatttta aggtttctga gttaaccaga
1621 aaaatagaaa ttaaaaacaa aacaaaaaaa aaaacaaaaa aaaacaaaag taattaaaa
1681 acaaaacctg atgaaacaga tgaaggaaga tgtggaaaaa atccttagcc agggctcaga
1741 gatgaagcag tgaaagagac aggaattggg agggaaaggg agaatggtgt accctttatt
1801 tcttctgaaa tcacactgat gacatcagtt gtttaaacgg ggtattgtcc tttccccct
1861 tgaggttccc ttgtgagcct tgaatcaacc aatctagtct gcagtagtgt ggactagaac
1921 aacccaaata gcatctagaa agccatgagt ttgaaagggc ccatcacagg cactttccta
1981 cccaattacc caggtcataa ggtatgtctg tgtgacactt atctctgtgt atatcagcat
2041 acacacacac acacacacac acacacacac acacaggcat ttccacacat tacatatata
2101 cacatactgg taaaagaaca atcgtgtgca ggtggtcaca cttccttttt ctgtaccact
2161 tttgcaacaa aacaa
```

(the coding sequence is shown in bold type)

Human Activin amino acid sequence [SEQ ID NO: 19]

```
MPLLWLRGFL LASCWIIVRS SPTPGSEGHS AAPDCPSCAL AALPKDVPNS QPEMVEAVKK
HILNMLHLKK RPDVTQPVPK AALLNAIRKL HVGKVGENGY VEIEDDIGRR AEMNELMEQT
SEIITFAESG TARKTLHFEI SKEGSDLSVV ERAEVWLFLK VPKANRTRTK VTIRLFQQQK
HPQGSLDTGE EAEEVGLKGE RSELLLSEKV VDARKSTWHV FPVSSSIQRL LDQGKSSLDV
RIACEQCQES GASLVLLGKK KKEEEGEGK KKGGGEGGAG ADEEKEQSHR PFLMLQARQS
EDHPHRRRRR GLECDGKVNI CCKKQFFVSF KDIGWNDWII APSGYHANYC EGECPSHIAG
TSGSSLSFHS TVINHYRMRG HSPFANLKSC CVPTKLRPMS MLYYDDGQNI IKKDIQNMIV
EECGCS
```

METHOD OF TREATING DEPRESSION

The present invention relates to a method for identifying a TMEFF2 modulator, comprising (a) contacting a cell which expresses TMEFF2 with a candidate compound to be tested; (b) measuring whether said compound to be tested decreases or increases the level of a constituent of the CRH signalling pathway, preferably the cAMP signalling pathway, in said cell when compared to a corresponding cell which does not express TMEFF2; (b') optionally determining whether said compound is capable of reducing the binding between Activin and TMEFF2; and (c) identifying said modulator compound. Furthermore, a method for identifying a TMEFF2 modulator comprising determining whether said TMEFF2 modulator is capable of reducing the binding between Activin and TMEFF2 is contemplated. It also relates to uses and methods applying a TMEFF2 agonist for the treatment of Cushing's Syndromes and a TMEFF2 modulator for the treatment of affective disorders. Furthermore, methods of diagnosing affective disorders or Cushing's Syndromes are provided.

The Hypothalamic-Pituitary-Adrenal Axis (HPA Axis) and its Role in Affective Disorders and Cushing's Syndromes Clinical and preclinical studies have gathered substantial evidence that alterations of the stress hormone system play a major causal role in the development of affective disorders. The hypothalamic-pituitary-adrenal axis (HPA axis) is a major part of the neuroendocrine system that controls reactions to stress. The HPA axis represents a hypothesis based on a response to stress by the hypothalamus, the pituitary gland, the adrenal cortices. The HPA axis includes parts of the hypothalamus, the anterior lobe of the pituitary gland, the adrenal cortices, hormones, systems that transport hormones and feedback mechanisms that transport cortisol from adrenal glands back to the hypothalamus and to other parts of the brain. The hypothalamus releases Corticotropin-releasing hormone (CRH) from an area along the median eminence. CRH is transported to the anterior lobe of the pituitary through the portal blood vessel system of the hypophyseal stalk, which descends from the hypothalamus. In the anterior pituitary gland, CRH stimulates release of stored adrenocorticotropic hormone (ACTH), which is transported by the blood to the adrenal cortex of the adrenal gland, where it rapidly stimulates biosynthesis of corticosteroids from cholesterol. Chronic activation of the HPA axis reduces the ability of cortisol to shut off the release of CRH and ACTH. Elevated CRH and ACTH levels are thought to be an important underlying cause of affective disorders. It is also assumed that the most common underlying cause of Cushing's Syndromes are excessive production of ACTH by the pituitary gland.

CRH plays a central role in the regulation of the hypothalamic-pituitary-adrenal (HPA) axis, mediating endocrine and behavioural responses to various stressors (Bale and Vale (2004) Annu. Rev. Pharmacol. Toxicol. 44: 525-557; Perrin and Vale (1999) Ann. N.Y. Acad. Sci. 885:312-328; Reul and Holsboer (2002) Curr. Opin. Pharmacol. 2:23-33; Grammatopoulos, 2002). At the pituitary level, CRH is a potent stimulator of pro-opiomelanocortin (POMC) gene expression and adrenocorticotropin (ACTH) production (Gagner and Drouin (1987) Mol. Endocrinol. 1:677-682). ACTH is produced by the cleavage of POMC. Activation of the CRH receptor 1 (CRHR1) by CRH results in Gs-mediated stimulation of adenylate cyclase, leading to increased levels of intracellular cAMP, which stimulates different transcription factors, including CREB and Nur77, which in turn activate the POMC promoter. A large body of preclinical and clinical evidence points to a key role of the CRHR1 in mediating CRH-elicited effects in anxiety, depressive disorders and stress-associated pathologies (Müller and Wurst (2004) Trends Mol. Med. 1: 409-415). In patients with depression, CRH levels in the cerebrospinal fluid are elevated and CRH expression in the hypothalamic paraventricular nucleus is increased as compared to controls (Müller and Wurst (2004) Trends Mol. Med. 1: 409-415). It has been proposed that normalization of the HPA axis, controlled by CRH signalling, might be the final common step of antidepressant action that is necessary for stable remission of affective disorders (Holsboer and Barden (1996) Endocr. Rev. 17, 187-205).

Accordingly, novel methods to regulate and inhibit CRH signalling can be used for the treatment of affective disorders and/or Cushing's Syndromes.

The Activin Signalling Pathway

Figure 17:
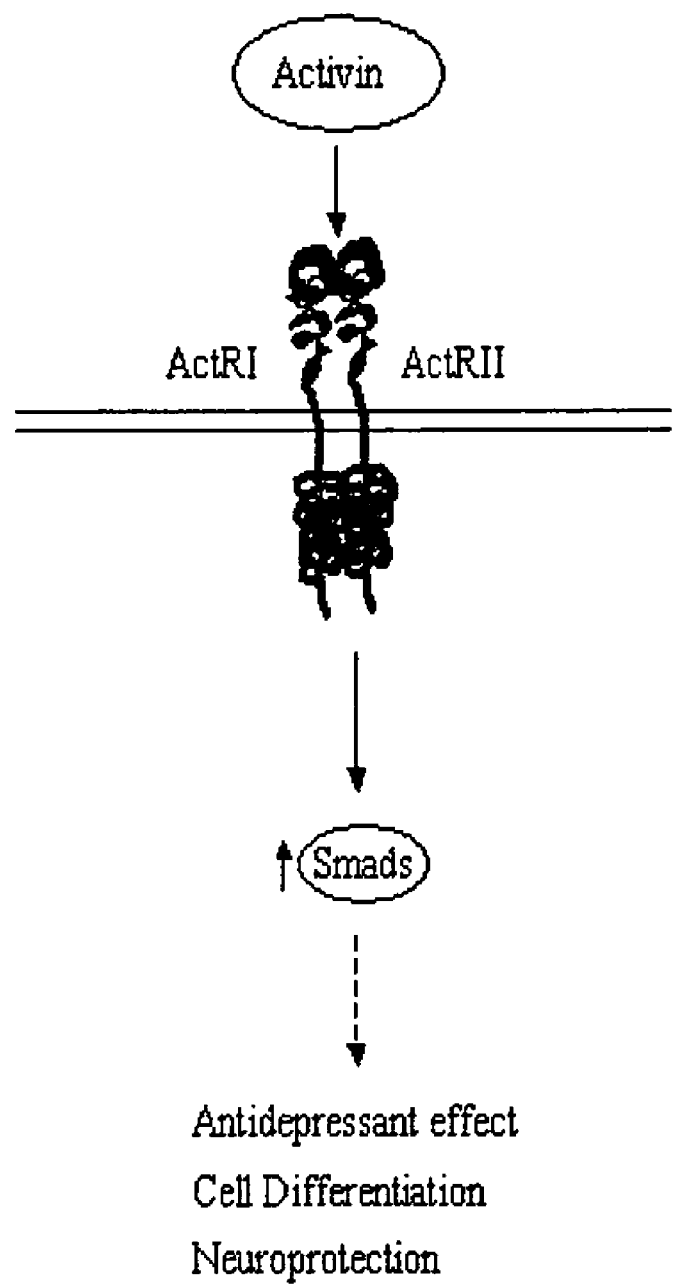

Activin is a member of the TGF-β superfamily and participates in several biological processes such as cell differentiation, neurogenesis, hormonal secretion, and neuronal survival (Schubert et al., 1990, Nature 344:868-870; Ameerum et al., 1996, Cell Growth Differ 12:1679-1688; Iwahori et al., 1997, Brain Res 760:52-58; Sulyok et al., 2004, Mol Cell Endocrinol 225:127-132). Activin is a secreted protein that binds a serine/threonine receptor complex comprised of a type II ligand binding receptor and a type I signal transducing receptor (FIG. 17). There are two subtypes of the type II Activin receptor in vertebrates, type IIA (ActRIIA) and IIB (ActRIIB). ActRIIA and ActRIIB are the primary Activin receptor and are constitutively active serine/threonine kinases that recruit type I receptor ALK4 (Activin receptor-like kinase 4) by means of bound Activin (Greenwald et al. (1999) *Nat Struct Biol* 6:18-22; Bernard et al. (2002) *Mol Cell Endocrinol* 196:79-93; Thompson et al. (2003) *EMBO J.* 22:1555-1566). The functional complex of Activin receptors at the cell surface consists of two type II receptors and two type I receptors. The cellular responses to Activin are mediated by phosphorylation of the transcription factors Smad2, Smad3 and other Smad proteins (Abe et al, 2004, Growth Factors 22:105-110). Smad proteins form homo- and heteromeric complexes that are capable of binding to DNA and regulate the expression of target genes.

Activin expression and Smad2 phosphorylation are increased during treatment with antidepressant drugs (Dow et al., 2005, J Neuroscience 25:4908-4916). Infusion of Activin into the hippocampus of animal models of depression has also been shown to have antidepressant-like effects. Consequently, regulation of Activin and Smad2 signalling can contribute to the action of antidepressant drugs.

Hence, novel methods to regulate and activate Smad signalling can be used for the treatment of affective disorders.

Affective Disorders

Up to 10% of persons visiting a physician are afflicted with an affective disorder (also known as behavioural disorder, mood disorder). Nonetheless, most cases remain undiagnosed or inadequately treated. Affective disorders include among others, depression, anxiety, and bipolar disorder. These diseases are well described in the literature; see, for example, Diagnostic and Statistical Manual of Mental Disorders-4th Edition Text Revision (DMS-IV-TR), American Psychiatric Press, 2000.

Depression, also known as unipolar affective disorder, is characterized by a combination of symptoms such as lowered mood, loss of energy, loss of interest, feeling of physical illness, poor concentration, altered appetite, altered sleep and a slowing down of physical and mental functions resulting in a relentless feeling of hopelessness, helplessness, guilt, and anxiety. The primary subtypes of this disease are major depression, dysthymia (milder depression), and atypical depression. Other important forms of depression are premenstrual dysphoric disorder and seasonal affective disorder. Present treatment of depression consists of psychotherapy, antidepressant drugs, or a combination of both. Most antidepressive drugs target the transport of the neurotransmitters serotonin and/or norepinephrine, or the activity of the enzyme monoamine oxidase. They include: Selective serotonin-reuptake inhibitors (e.g., fluoxetine, paroxetine, sertraline, fluvoxamine), tricyclic antidepressants (e.g., amitriptyline, imipramine, desipramine, nortriptyline), monoamine oxidase inhibitors (e.g., phenelzine, isocarboxazid, tranylcypromine), and designer antidepressants such as mirtazapine, reboxetine, nefazodone. However, all existing antidepressive drugs possess shortcomings such as long latency until response, high degree of non-responders, and undesirable side effects (Holsboer, Biol. Psychol. 57 (2001), 47-65). Therefore, a need exists in the medical community for new antidepressive drugs with different mechanisms of action and improved pharmacological profile (Baldwin (2001) Hum. Psychopharmacol. Clin. Exp. 16:S93-S99; Greden (2002) J. Clin. Psychiatry 63(Suppl 2):3-7).

Anxiety disorders are defined by an excessive or inappropriate aroused state characterized by feelings of apprehension, uncertainty, or fear. They are classified according to the severity and duration of their symptoms and specific affective characteristics. Categories include: (1) Generalized anxiety disorder, (2) panic disorder, (3) phobias, (4) obsessive-compulsive disorder, (5) post-traumatic stress disorder, and (6) separation anxiety disorder. The standard treatment for most anxiety disorders is a combination of cognitive-behavioural therapy with antidepressant medication. Additional medications include benzodiazepines such as alprazolam, clonazepam, diazepam, lorazepam, halazepam, chlordiazepoxide, and other drugs such as buspirone, clonidine, pagoclone, risperidone, olanzapine, quetiapine, ziprasidone. Nonetheless, there are a number of unmet needs in the treatment of anxiety disorders including the need for more effective, rapidly acting, and better tolerated medications; effective treatments for refractory disorders; prevention of relapse; and promotion of resilience and long-lasting response (Pollack, Psychopharmacol. Bull. 38(Suppl 1) (2004) 31-37).

Bipolar disorder, also known as manic-depression, is characterized by mood swings between periods of mania (i.e. mood elevation including exaggerated euphoria, irritability) and periods of depression. Bipolar disorder is classified according to the severity of the symptoms. Patients diagnosed with bipolar disorder type I suffer from manic or mixed episodes with or without major depression. In Bipolar Disorder type II, patients have episodes of hypomania and episodes of major depression. With hypomania the symptoms of mania (euphoria or irritability) appear in milder forms and are of shorter duration. The current drugs used to treat bipolar disorders are lithium, valproate and lamotrigine, which stimulates the release of the neurotransmitter glutamate. As with antidepressive drugs, they take weeks to become effective and can result in undesirable side effects, for example, high levels of lithium in the blood can be fatal (Sachs (2003) J. Clin. Psychopharmacol. 23(Suppl. 1):S2-S8).

Cushing's Syndromes

Cushing's Syndromes are hormonal diseases with an estimated incidence of approximately 10 per 1 million persons (Meier and Biller (1997) Endocrinol Metab Clin North Am 26:741-762). Cushing's Syndromes are associated with an increased blood concentration of cortisol (hypercortisolism) or the presence of glucocorticoid hormone over a long period of time. The most common underlying cause of Cushing's Syndromes are excessive production of ACTH by the pituitary gland. As mentioned above, ACTH stimulates the growth of the adrenal glands and the secretion of other corticosteroids. Elevated ACTH levels is most often produced by pituitary adenomas. Cushing's Syndromes resulting from the production of ACTH in a location other than the pituitary gland is known as ectopic Cushing's Syndromes. Examples of ectopic sites include thymoma, medullary carcinoma of the thyroid, pheochromocytoma, islet cell tumours of the pancreas and oat cell carcinoma of the lung. Symptoms of Cushing's Syndromes include weight gain, central obesity, steroid hypersecretion, elevated urinary cortisol excretion, moon face, weakness, fatigue, backache, headache, impotence, mental status changes, muscle atrophy, and increased thirst and urination. At the pituitary level, CRH stimulates ACTH synthesis. ACTH overproduction by pituitary adenomas leads to excessive glucocorticoid secretion from the adrenal glands which causes endogenous Cushing's Syndromes, characterized by a typical abnormal fat deposition around the neck, thinning of the skin, osteoporosis, insulin resistance, dyslipidemia, myopathy, amenorrhea and hypertension. Fatigue, irritation, anxiety and depression are also common clinical features in these patients (Orth (1995) N. Engl. J. Med. 332: 791-803; Dahia and Grossman (1999) Endocr. Rev. 20:136-55).

Although ACTH-secreting pituitary tumours found in Cushing's Syndromes are rarely invasive, they nonetheless cause considerable morbidity due to the excess of glucocorticoid production. ACTH-secreting tumours cause elevated, non-suppressible, ACTH levels, hypercortisolemia, and varied clinical manifestations, including diabetes, hypertension, muscle weakness, and osteoporosis (Ross et al. (1982) Lancet 2: 646-649). Consequently, ACTH-secreting pituitary tumours are associated with high morbidity and ultimately mortality unless treated (Oldfield et al. (1991) N. Engl. J. Med. 325: 897-905).

Effective drug therapies for Cushing's Syndromes and ACTH-secreting pituitary tumours currently do not exist. Surgery to remove the tumour is the treatment mainstay (Simmons et al. (2001) J. Neurosurg. 95:1-8; Mampalam, et al. (1988) Ann. Intern. Med. 109:487-493; Hoybye et al. (2001) Neurosurgery 49:284-291).

Pharmacological therapy with cyproheptadine, an anti-serotonin agent, has been used in the past to suppress ACTH secretion, but ultimate efficacy was poor, and its use has since been discontinued (Krieger et al. (1975) N. Engl. J. Med. 293:893-896). While the antifungal ketoconazole can suppress adrenal cortisol biosynthesis, the drug does not inhibit pituitary tumour growth or ACTH secretion. Furthermore idiosyncratic hepatic toxicity limits its long-term use in patients (Sonino (1987) N. Engl. J. Med. 317:812-818).

In view of the above, a need exists to provide new therapeutic agents and methods for treating affective disorders and/or Cushing's Syndromes. Therefore, the technical problem underlying the present invention is to provide means and methods for diagnosing and/or treating affective disorders and/or Cushing's Syndromes.

The solution to said technical problem is achieved by providing the embodiments characterized hereinbelow and in the claims.

Surprisingly, the present inventors have found that by modulating TMEFF2 it is possible to provide means and methods for treating affective disorders and/or Cushing's Syndromes. The invention is based, in part, on the observations that TMEFF2 is, without being bound by theory, involved in two signalling pathways. On the one hand TMEFF2 is involved in the CRH signalling pathway, preferably in the cAMP signalling pathway, and on the other hand in the Activin signalling pathway.

Based on these findings the present invention provides the teaching that TMEFF2 agonists increase its effect on the CRH signalling pathway, preferably the cAMP pathway can be useful for treating Cushing's syndromes.

Moreover, the findings that TMEFF2 is involved in the Activin signalling pathway support the conclusion that TMEFF2 modulators which reduce the binding between Activin and TMEFF2 can be used in the treatment of affective disorders.

Accordingly, as detailed herein below and also illustrated in the experimental part of the present application, the instant invention provides for a method for identifying a TMEFF2 modulator, preferably a TMEFF2 modulator of the CRH signalling pathway, preferably the cAMP signalling pathway comprising (a) contacting a cell which expresses TMEFF2 with a candidate compound to be tested;
(b) measuring whether said compound to be tested decreases or increases the level of a constituent of the CRH signalling pathway, preferably cAMP signalling pathway, in said cell when compared to a corresponding cell which does not express TMEFF2; and
(c) identifying said modulator compound.

The TMEFF2 modulator to be identified by the above described method is preferably a TMEFF2 agonist. Said TMEFF2 agonist identified by the above described method is preferably a TMEFF2 agonist of the CRH signalling pathway, preferably the cAMP signalling pathway which is herein referred to as "TMEFF2 agonist of CRH signalling pathway, preferably the cAMP signalling pathway" or as "TMEFF2 CRH signalling pathway, preferably cAMP signalling pathway agonist". Accordingly, if the above described method is applied for identifying a TMEFF2 agonist, then in step (b) the decrease of the level of a constituent of the cAMP signalling pathway, preferably the CRH signalling pathway, is measured in a cell which expresses TMEFF2 and compared to a corresponding cell which does not express TMEFF2.

However, of course, the TMEFF2 modulator, identified by the above described method, may also be a TMEFF2 antagonist as will be described hereinbelow. Said TMEFF2 antagonist identified by the above described method is herein referred to as "TMEFF2 antagonist of the CRH signalling pathway, preferably of the cAMP signalling pathway" or "TMEFF2 CRH signalling pathway, preferably cAMP signalling pathway antagonist". Accordingly, then in step (b) of the above described method the increase of the level of a constituent of the cAMP signalling pathway, preferably the CRH signalling pathway, is measured in a cell which expresses TMEFF2 and compared to a corresponding cell which does not express TMEFF2.

The methods for identifying TMEFF2 modulators are preferably carried out in vitro.

It has been unexpectedly found that inactivation of the transmembrane protein with EGF-like and two follistatin-like domains 2 (TMEFF2) can activate Corticotropin-releasing hormone (CRH) signalling, while activation of TMEFF2 can inhibit CRH signalling. Without being bound by theory, inhibition of CRH signalling is believed to finally lead to a decreased level of ACTH. Since an increased level of ACTH is believed to play a major role in the onset and/or manifestation of affective disorders and Cushing's Syndromes, it is desired to lower the level of ACTH. The present inventors have now found that CRH signalling can be modulated via TMEFF2.

Figure 2:
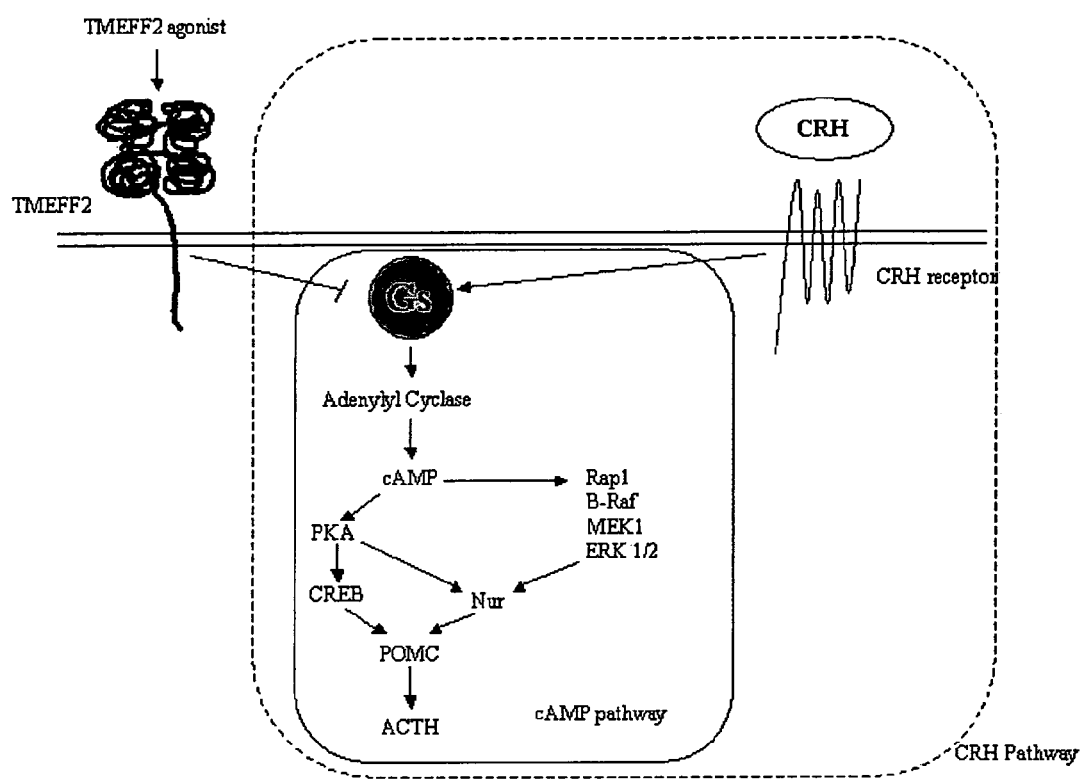

FIG. 2 illustrates the signalling pathway in which, inter alia, TMEFF2 is believed to be involved. Specifically, FIG. 2 shows the CRH signalling pathway, in particular the cAMP signalling pathway. In more detail, activation of the CRH receptor 1 (CRHR1) by CRH results in Gs-mediated stimulation of adenylate cyclase (also referred to herein as adenylyl cyclase), leading to increased levels of intracellular cAMP, which stimulates protein kinase A which can activate different transcription factors, including CREB and Nur77 and Nurr1 (both belong to the Nurr family), which in turn activate the POMC promoter. ACTH is produced by the cleavage of POMC. The role of TMEFF2 is, according to the findings of the present invention, to act as an inhibitor of the CRH signal transduction pathway.

Accordingly, activation of TMEFF2 inhibits CRH signalling and, thus, leads to a decrease of the level of ACTH which is desirable when aiming at the treatment of affective disorders and/or Cushing's Syndromes.

Thus, TMEFF2 agonists, preferably TMEFF2 agonists of the CRH signalling pathway, preferably the cAMP signalling pathway, such as TMEFF2 itself and agents as described hereinbelow that stimulate the activity of TMEFF2 can be used in the treatment of affective disorders and/or Cushing's Syndromes which is described in more detail herein below. The treatment of Cushing's Syndromes by applying a TMEFF2 agonist is preferred.

Indeed, as shown in Example 2, TMEFF2 is expressed in pituitary cells which are a major source for ACTH. Furthermore as demonstrated in Example 4, inhibition of TMEFF2 results in an increase of POMC expression. In Examples 6 and 7 it is demonstrated that inhibition of TMEFF2 enhances Nurr1 and Nur77 and CREB transcriptional activity. Example 8 demonstrates that TMEFF2 inhibition increases CRH-induced stimulation of cAMP. Since ACTH is produced by the cleavage of POMC, an increase in POMC expression is indicative of an increase in ACTH levels. By contrast, a decrease in POMC expression is indicative of a decrease of ACTH levels. Accordingly, it is assumed that TMEFF2 activation decreases POMC expression and, thus, ACTH production. In fact, in Example 11 it is demonstrated that activation of TMEFF2 inhibits CRH-signalling and ACTH production.

Consequently, TMEFF2s, preferably TMEFF2 agonists of the CRH signalling pathway, preferably cAMP signalling pathway can be used to treat affective disorders and/or Cushing's Syndromes. Cushing's Syndromes are preferred.

The expression of POMC, and consequently the production of ACTH, is regulated by the transcription factor Nurr1 (Philips et al. (1997) Mol. Cell. Biol. 17:5952-5959; Philips et al., (1997) Mol. Cell. Biol. 17:5946-5951). Example 6 shows that inhibition of TMEFF2 increases the stimulation of Nurr1 activity by CRH. Consequently, activation of TMEFF2 will results in a decrease of CRH-induced activity of Nurr1. Reduction in Nurr1 is indicative of a decrease of POMC expression and ACTH synthesis.

CRH effects on corticotroph cells in the pituitary gland are mediated by G protein-coupled CRHR1 (i.e. the receptor for CRH). CRH stimulation of the receptor activates a Gs-protein that in turn activates the adenylate cyclase resulting in the conversion of ATP to cyclic AMP (cAMP). cAMP activates protein kinase A (PKA) leading to the transcription of POMC and ACTH synthesis (Boutillier et al. (1991) Mol. Endocrinol. 5:1301-1310). As demonstrated in Example 8, inhibition of TMEFF2 increases the levels of cAMP induced by CRH. By contrast, activation of TMEFF2 decreases the levels of cAMP induced by CRH. This indicates that TMEFF2 inhibits protein Gs and does not activate a G protein as previously speculated by Uchida et al. (1999) Biochem. Biophys. Res. Commun. 266:593-602. cAMP is an activator of the transcription factor CREB (cyclic AMP response element binding) which mediates CRH signal transduction (Boutillier et al. (1998) Pituitary 1:33-43). Inhibition of TMEFF2 results in an increase of CREB activity as demonstrated in Example 7. By contrast, activation of TMEFF2 decreases CREB activity and reduces the effects of CRH signalling.

The above examples demonstrate for the first time that downregulation of TMEFF2 enhances the effects of CRH on pituitary cells, thus increasing cAMP, which in turn upregulates POMC transcription and increases ACTH levels. These examples further demonstrate that TMEFF2 acts as an inhibitor of the CRH signal transduction pathway. Therefore activation of TMEFF2 by agonists and partial agonists can inhibit the effects of CRHR1 signalling and can be used in the treatment of affective disorders and/or Cushing's Syndromes. Cushing's Syndromes are preferred.

The role of TMEFF2 in the treatment of Cushing's Syndromes is further illustrated in Examples 9 and 10. Inhibition of TMEFF2 in ACTH-producing pituitary tumour cells increases cell proliferation. This demonstrates that activation of TMEFF2 exerts antiproliferative effects on pituitary tumours. TMEFF2 expression is also reduced in pituitary tumours isolated from patients suffering from Cushing's Syndromes; see Example 10. Low or no expression of TMEFF2 is observed in Cushing's adenomas. These examples demonstrate that activation of TMEFF2 can be used to reduce the size and effects of ACTH-producing pituitary tumour for the treatment of individuals with Cushing's Syndromes. The examples further demonstrate that Cushing Syndromes can be diagnosed according to the expression levels of TMEFF2. Reduced or absent TMEFF2 expression is indicative of Cushing's Syndromes. Similarly, also an affective disorder can be diagnosed according to the expression levels of TMEFF2. Methods for diagnosing Cushing's Syndromes or affective disorders are further described hereinbelow.

The above described findings which are illustrated in the appended Examples are indeed surprising since the prior art believed that TMEFF2 would have an activating role on a Gs protein (see Uchida, et al. (1999) Biochem. Biophys. Res. Commun. 266:593-602). However, the present invention shows that TMEFF2 acts in an inhibitory fashion on the cAMP signalling pathway, preferably the CRH signalling pathway, which is involved in the regulation of the production of ACTH. ACTH, if present in unphysiological high amounts over a prolonged period of time, is believed to play a major role in the onset and/or manifestation of affective disorders and/or Cushing's Syndromes as described in more detail hereinbelow. These findings thus pave the way for the development of novel means and methods for treating and/or preferably diagnosing affective disorders and/or Cushing's Syndromes by modulating the cAMP signalling pathway via TMEFF2.

In the brain, TMEFF2 has been shown to be highly expressed in the medial habenular, CA2, CA3 and dentate gyrus region of the hippocampus, corpus callosum, cerebellar cortex and cranial nerve nuclei III, IV, VII, X, and XII (Kanemoto et al. (2001) Mol. Brain. Res. 86:48-55). Recombinant TMEFF2 protein fragment consisting of the putative extracellular domain has been used and it was shown that TMEFF2 increased survival of neurons from the hippocampus and midbrain, but not from the cerebral cortex, indicating that the survival effects of TMEFF2 are specific to certain cell types. Recombinant TMEFF2 also promoted survival of mesencephalic dopaminergic neurons. These findings indicate that TMEFF2 holds promise as a candidate for use in the treatment of neurodegenerative disorders such as Parkinson's disease (Horie et al. (2002) Genomics 67:146-152). However, there is no indication in the prior art that TMEFF2 or the activation of TMEFF2 by agonist agents can be used to treat affective disorders or preferably Cushing's Syndromes.

TMEFF2 was first identified in human brain cDNA library (see Uchida, et al. (1999) Biochem. Biophys. Res. Commun. 266:593-602), and later isolated from a human foetal brain (see Horie, et al. (2000) Genomics 67:146-152). Further human or mouse nucleic acids for TMEFF2 are disclosed in Genbank Accession numbers NM_016192, NM_019790, BC034850, BC008973, AY412287, AY412288, AY412289, AB017270, and AB017269. TMEFF2 is also known as tomoregulin, TR, hyperplastic polyposis gene 1, HPP 1, and TENB2.

The TMEFF2 gene encodes a protein that contains two follistatin-like domain, and one EGF-like domain. The protein also possesses a cytolosic tail that contains a G protein activating motif; see also Example 1. It has been suggested that the extracellular domain of TMEFF2 can be released into the extracellular matrix via proteolytic cleavage (Horie et al. (2002) Genomics 67:146-152); see also Example 1. FIG. 1 illustrates the soluble form of the TMEFF2 protein.

TMEFF2 expression may be controlled by androgen (Gery et al. (2002) Oncogene 21:4739-4746).

Moreover, in addition to the above, it has been further surprisingly found that TMEFF2 is involved in the Activin signalling pathway. In particular, as mentioned herein-above, the TMEFF2 protein possesses an extracellular region containing follistatin-like and EGF-like domains, a transmembrane region and a cytoplasmic tail (FIG. 1). The extracellular domain has been shown to be cleaved by proteases near the transmembrane region. This proteolytic cleavage releases the extracellular portion of TMEFF2, which then can act as a cytokine or growth factor capable of binding to the erbB family of EGF receptors (Horie et al. (2002) Genomics 67:146-152).

Activin is a member of the TGF-β superfamily and participates in several biological processes such as cell differentiation, neurogenesis, hormonal secretion, and neuronal survival (Schubert et al., 1990, Nature 344:868-870; Ameerum et al., 1996, Cell Growth Differ 12:1679-1688; Iwahori et al., 1997, Brain Res 760:52-58; Sulyok et al., 2004, Mol Cell Endocrinol 225:127-132). Activin is a secreted protein that binds a serine/threonine receptor complex comprised of a type II ligand binding receptor and a type I signal transducing receptor (FIG. 17). There are two subtypes of the type II Activin receptor in vertebrates, type IIA (ActRIIA) and IIB (ActRIIB). ActRIIA and ActRIIB are the primary Activin receptor and are constitutively active serine/threonine kinases that recruit type I receptor ALK4 (Activin receptor-like kinase 4) by means of bound Activin (Greenwald et al. (1999) *Nat Struct Biol* 6:18-22; Bernard et al. (2002) *Mol Cell Endocrinol* 196:79-93; Thompson et al. (2003) *EMBO J.* 22:1555-1566). The functional complex of Activin receptors at the cell surface consists of two type II receptors and two type I receptors. The cellular responses to Activin are mediated by phosphorylation of the transcription factors Smad2, Smad3 and other Smad proteins (Abe et al, 2004, Growth Factors 22:105-110). Smad proteins form homo- and heteromeric complexes that are capable of binding to DNA and regulate the expression of target genes.

Activin expression and Smad2 phosphorylation are increased during treatment with antidepressant drugs (Dow et al., 2005, J Neuroscience 25:4908-4916). Infusion of Activin into the hippocampus of animal models of depression has also been shown to have antidepressant-like effects. Consequently, regulation of Activin and Smad2 signalling can contribute to the action of antidepressant drugs.

The present inventors now obtained experimental results which support the conclusion that TMEFF2 through its follistatin-like domains is capable of binding Activin, prevent the binding of Activin to type II Activin receptors, and by consequence inhibit Activin signalling (FIG. 18), thereby reducing activity of Smad proteins. Thus, molecules which reduce the binding of Activin to TMEFF2 allow Activin to bind its receptor, activate Smads and promote antidepressant effects, cell differentiation and neuronal survival (FIG. 19).

Accordingly, the TMEFF2 modulators identified in accordance with the methods of the present invention described hereinabove, i.e. TMEFF2 agonists or antagonists can be further tested whether or not they can modulate the Activin signalling pathway via action on TMEFF2, in particular whether they can lead to a reduced binding of Activin to TMEFF2.

Accordingly, the present invention provides a method for identifying a TMEFF2 modulator comprising
(a) contacting a cell which expresses TMEFF2 with a candidate compound to be tested;
(b) measuring whether said compound to be tested decreases or increases the level of a constituent of the CRH signalling pathway, preferably a constituent of the cAMP signalling pathway, in said cell when compared to a corresponding cell which does not express TMEFF2;
(b') determining whether said compound to be tested reduces binding of Activin to TMEFF2; and
(c) identifying said modulator compound.

However, the present invention not only provides TMEFF2 modulators identified in accordance with the above described methods (referred to as "modulators of the CRH signalling pathway, preferably cAMP signalling pathway"), but also provides a screening method for identifying compounds which can reduce the binding of Activin to TMEFF2. Such compounds are, in the following referred to as "TMEFF2 modulators that act on the Activin signalling pathway" or "TMEFF2 modulators of the Activin signalling pathway". By reducing the binding of Activin to TMEFF2, the effect of Activin on the Activin signalling pathway is increased. Thus, such compounds can be used in methods or uses for treating affective disorders.

Thus, in essence, a TMEFF2 modulator that acts on the Activin signalling pathway could also be seen as an "agonist of the Activin signalling pathway". As described above, a TMEFF2 modulator which reduces the binding of Activin to TMEFF2 enhances the binding of Activin to its cognate receptor which in turn leads to a more efficient activation of the Activin signalling pathway.

Accordingly, the present invention provides a method for identifying a modulator of TMEFF2, preferably with regard to its involvement in the Activin signalling pathway, in particular a modulator which reduces the binding of Activin to TMEFF2.

In particular, the present invention provides a method for identifying a TMEFF2 modulator by determining whether it is capable of reducing the binding between Activin and TMEFF2. Such a method can be carried out by techniques known to the person skilled in the art, e.g.
(a) contacting TMEFF2 and Activin with a candidate compound to be tested;
(b) measuring whether said compound to be tested reduces or inhibits the binding of Activin to TMEFF2; and
(c) identifying said modulator compound.

The term "binding of Activin to TMEFF2" or "binding between Activin or TMEFF"" means that Activin binds to TMEFF2 and vice versa.

The term "reduced" or "reducing" as used herein defines the reduction of the binding of Activin to TMEFF2 when compared to the normal/natural binding of Activin to TMEFF2. Accordingly, it will be understood that the reduction mediated by the test compound, preferably a TMEFF2 modulator that acts on the Activin signalling pathway, aims at "reducing" the binding of Activin to TMEFF2. It is also envisaged that the test compound, preferably a TMEFF2 modulator that acts on the Activin signalling pathway totally abolishes the binding of Activin to TMEFF2 when compared to the normal/natural binding of Activin to TMEFF2. The term "normal/natural binding" means the capability of Activin to bind to TMEFF2 or vice versa. As is described herein, binding of Activin to its cognate receptor leads to the induction of, inter alia, Smad proteins. TMEFF2 is believed to bind to Activin and, thereby, reducing the ability to bind to its receptor.

Accordingly, it is envisaged that the test compound at least reduces the binding of Activin to TMEFF2 by 5%, 10%, 20%, 30%, 40%, 50%, 60%, 70%, 80%, 90% or even 100% when compared to a normal/natural binding of Activin to TMEFF2. The binding of Activin to TMEFF2 can be measured, e.g., as described herein below.

In view of the above described surprising findings of the invention, the present invention provides means and methods for identifying TMEFF2 modulators. Said TMEFF2 modulators are preferably either antagonists or agonists, preferably antagonists or agonists of the CRH signalling pathway, preferably the cAMP signalling pathway, and/or preferably modulators that act on the Activin signalling pathway.

As mentioned above, TMEFF2 antagonists or agonists of the CRH signalling pathway, preferably cAMP signalling pathway can be further tested whether or not they can act as TMEFF2 modulators of the Activin signalling pathway. Likewise, TMEFF2 modulators of the Activin signalling pathway can be tested whether or not they can act as TMEFF2 antagonists or agonists of the CRH signalling pathway, preferably cAMP signalling pathway. Accordingly, for example, a TMEFF2 antagonist or agonist of the CRH signalling pathway, preferably cAMP signalling pathway can also act as a TMEFF2 modulator of the Activin signalling pathway.

Likewise, a TMEFF2 modulator of the Activin signalling pathway can also be a TMEFF2 antagonist or agonist of the CRH signalling pathway, preferably cAMP signalling pathway.

Preferably, a TMEFF2 agonist or antagonist of the CRH signalling pathway, preferably cAMP signalling pathway is also a TMEFF2 modulator of the Activin signalling pathway.

Of course, it is possible to differentiate whether a compound to be tested acts as a TMEFF2 antagonist or agonist of the CRH signalling pathway, preferably cAMP signalling pathway, or as modulator of the Activin signalling pathway. Specifically, activation of the CRH signalling pathway, preferably cAMP signalling pathway, can be measured by different outputs as disclosed herein. Thus, the skilled person is readily in the position to determine whether a compound to be tested is a TMEFF2 antagonist or agonist of the CRH signalling pathway, preferably cAMP signalling pathway or a modulator of the Activin signalling pathway, respectively, or acts on both signalling pathways which, as described above, is possible.

Before the present invention is described in detail, it is to be understood that this invention is not limited to the particular methodology, protocols, cell lines, vectors, and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

TMEFF2

When used in the context of the present application the term "TMEFF2" includes a TMEFF2 (also known as tomoregulin, TR, hyperplastic polyposis gene 1, HPP 1, and TENB2) polynucleotide or polypeptide having a nucleotide or amino acid sequence, respectively, as is known in the art; see Uchida, et al. (1999) Biochem. Biophys. Res. Commun. 266:593-602); Horie, et al. (2000) Genomics 67:146-152); or Genbank Accession numbers NM_016192, NM_019790, BC034850, BC008973, AY412287, AY412288, AY412289, AB017270, and AB017269. FIG. 16 shows the nucleotide sequence and the amino acid sequence of human TMEFF2 as described in Uchida, et al. (1999), cited above. When referring herein to TMEFF2 nucleotide sequences or TMEFF2 amino acid sequences, the sequences shown in FIG. 16 are preferred as "reference sequences" when, e.g. determining the degree of identity of nucleotide or amino acid sequences which are encompassed by the term "TMEFF2".

The term "TMEFF2" also includes nucleotide sequences which are 60, 70, 80, 90, 95, 97, 98, 99% identical to the TMEFF2 nucleotide sequences which are known in the art and described herein, wherein these 60, 70, 80, 90, 95, 97, 98, 99% identical nucleotide sequences encode a TMEFF2 polypeptide which retains the activity of modulating the cAMP signalling pathway as described herein. The nucleotide sequences according to the invention may be any type of nucleic acid, e.g. DNA, RNA or PNA (peptide nucleic acid).

The term "TMEFF2" also includes amino acid sequences which are 60, 70, 80, 90, 95, 97, 98, 99% identical to the TMEFF2 amino acid sequences which are known in the art and described herein, wherein these 60, 70, 80, 90, 95, 97, 98, 99% identical amino acid sequences retain the activity of modulating the cAMP signalling pathway as described herein. Said term also includes TMEFF2 polypeptide variants having an amino acid sequence, wherein in such variants one or more, preferably 2, 4, 6, 8, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350 or 360 amino acids are added, deleted and/or substituted as long as such TMEFF2 polypeptide variants retain the activity of modulating the cAMP signalling pathway as described herein. Said term also includes TMEFF2 polypeptide fragments, preferably of 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350 or 360 amino acids in length, wherein such fragments retain the activity of modulating the cAMP signalling pathway as described herein.

Said term also includes polynucleotides encoding said TMEFF2 polypeptide, fragments or variants thereof, respectively.

Activin

When used in the context of the present application, the term "Activin" includes an Activin (also known as inhibin beta A; activin A; activin AB alpha polypeptide) polynucleotide or polypeptide having a nucleotide or amino acid sequence, respectively, as is known in the art; see Risbridger et al. (2001) Endocrine Reviews 22:836-858; or Genbank Accession numbers NM_002192, AC005027, AU137531, BC007858, CCDS5464, NP_002183, AF218018, AK222742, AU137531, BC007858, BX648811, D49743, J03634, M13436, X72498, AAG17260, BAD96462, AAH07858, CAI46003, BAA08577, AAA35787, AAA59168, CAA51163, P08476, Q53H39, Q5HYA2, Q9HBP0, NM_008380, NP_032406, X69619, CCDS26251, AK134991, AK135474, BC053527, CT010380, X69619, BAE22374, BAE22545, AAH53527, CAJ18587, CAA49325, Q04998, Q3UXL8, Q3UY39, Q4FJM4, Q9JJQ1, NM_017128, M37482, NP_058824, and AAA41436. FIG. 22 shows the nucleotide sequence and the amino acid sequence of human Activin as disclosed in Genbank Accession number NM_002192. When referring herein to Activin nucleotide sequences or Activin amino acid sequences, the sequences shown in FIG. 22 are preferred as "reference sequences" when, e.g. determining the degree of identity of nucleotide or amino acid sequences which are encompassed by the term "Activin".

The term "Activin" also includes nucleotide sequences which are 60, 70, 80, 90, 95, 97, 98, 99% identical to the Activin nucleotide sequences which are known in the art and described herein, wherein these 60, 70, 80, 90, 95, 97, 98, 99% identical nucleotide sequences encode a Activin polypeptide which retains the property of binding to TMEFF2 as described herein. The nucleotide sequences according to the invention may be any type of nucleic acid, e.g. DNA, RNA or PNA (peptide nucleic acid).

The term "Activin" also includes amino acid sequences which are 60, 70, 80, 90, 95, 97, 98, 99% identical to the Activin amino acid sequences which are known in the art and described herein, wherein these 60, 70, 80, 90, 95, 97, 98, 99% identical amino acid sequences retain the property of binding to TMEFF2 as described herein. Said term also includes Activin polypeptide variants having an amino acid sequence, wherein in such variants one or more, preferably 2, 4, 6, 8, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350 or 360 amino acids are added, deleted and/or substituted as long as such Activin polypeptide variants retain the property of binding to TMEFF2 as described herein. Said term also includes Activin polypeptide fragments, preferably of 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350 or 360 amino acids in length, wherein such fragments retain the property of binding to TMEFF2 as described herein.

Said term also includes polynucleotides encoding said Activin polypeptide, fragments or variants thereof, respectively".

TMEFF2 Modulators

In the context of the present invention the term "TMEFF2 modulator" (sometimes also referred to herein simply as "modulator") means (a) compound(s), a complex of compounds, (a) substance(s) or complex of substances which can modify, i.e. modulate the activity of TMEFF2 or the expression of TMEFF2 either directly or indirectly. The modulation can, for example, occur at the protein level. Particularly, the TMEFF2 protein may interact with the modulator such that it is either more active or less active. The modulation can also occur on nucleic acid level. Namely, the TMEFF2 gene is transcribed more frequently or less frequently giving rise to more or less protein. Modulation can also influence RNA or protein stability. The term "TMEFF2 modulator" encompasses both a TMEFF2 antagonist and a TMEFF2 agonist.

The present invention in particular relates to "TMEFF2 antagonists" which encompass TMEFF2 antagonists of the CRH signalling pathway.

Moreover, the present invention relates to "TMEFF2 agonists" which encompass TMEFF2 agonists of the CRH signalling pathway.

The terms "TMEFF2 antagonist of the CRH signalling pathway, preferably cAMP signalling pathway" or "TMEFF2 agonist of the CRH signalling pathway, preferably cAMP signalling pathway" mean that a TMEFF2 antagonist or agonist influences or acts on the CRH signalling pathway, preferably cAMP signalling pathway via modulating TMEFF2. As described herein and shown in FIG. 2 TMEFF2 is, without being bound by theory, involved in the CRH signalling pathway, preferably cAMP signalling pathway.

The present invention moreover relates to "TMEFF2 modulators of the Activin signalling pathway" which refers to compounds which reduce the binding of Activin to TMEFF2 (and vice versa) and thereby influence or act on the Activin signalling pathway. Accordingly, a TMEFF2 modulator of the Activin signalling pathway could also be seen as an agonist of the Activin signalling pathway. As described herein and shown in FIG. 18 TMEFF2 is, without being bound by theory, involved in the Activin signalling pathway. As mentioned herein, a TMEFF2 modulator of the Activin signalling pathway" can preferably be a TMEFF agonist or antagonist, preferably a TMEFF2 agonist or antagonist of the CRH signalling pathway, preferably the cAMP signalling pathway.

A "TMEFF2 agonist" encompasses full agonists and partial agonists. A full agonist comprises an endogenous substance, a compound, a small molecule, an agent, or a drug that can interact with the TMEFF2 protein and initiate a maximal or complete physiological or a pharmacological response characteristic of TMEFF2. A partial agonist of TMEFF2 is an endogenous substance, a compound, a small molecule, an agent, or a drug which possesses affinity for TMEFF2, but unlike a full agonist, will elicit only a small degree of physiological or a pharmacological response characteristic of TMEFF2, even if a high proportion of TMEFF2 proteins are occupied by the endogenous substance, a compound, a small molecule, an agent, or a drug. Alternatively, a TMEFF2 agonist can interact with the TMEFF2 gene so as to enhance its transcription. The term "gene" means a nucleotide sequence associated with the production of a protein, including promoter sequences, enhancer sequences, intron sequences, exon sequences, coding regions, 5' untranslated region (5'UTR), 3' untranslated region (3'UTR), and splice variants. A TMEFF2 agonist can also influence RNA or protein stability.

The characteristics of a TMEFF2 agonist and partial agonist may be determined according to the formula:

$$\text{Response} = f(S) = f\left(\frac{[A]\varepsilon[R_T]}{[A] + K_d}\right)$$

where (S) correspond to stimulus; f is the efficiency of the mechanisms which convert (S) to effector response; [A] correspond to the concentration of an endogenous substance, a compound, a small molecule, an agent; $[R_T]$ is the total number of TMEFF2 protein; $\varepsilon$ is the intrinsic efficacy that denotes the ability of an endogenous substance, a compound, a small molecule, an agent, or a drug to produce a response; $K_d$ is the equilibrium dissociation constant of the agonist-receptor complex.

The magnitude of the response will thus depend ion the intrinsic efficacy value so that, by classical definition, full agonists ($\varepsilon$=1) produce that maximum response for a given tissue, partial agonists produce a maximum response that is below that induced by the full agonist ($0 \leq \varepsilon \leq 1$), and antagonists produce no visible response and block the effect of agonists ($\varepsilon$=0). Further quantitative approaches to characterise agonists, partial agonists and antagonist are well known in the art, see for example Wermuth (Ed) "The Practice of Medicinal Chemistry", Academic Press, 1996.

In accordance with the present invention, the term "TMEFF2 antagonist", also referred herein as "TMEFF2 inhibitor" denotes molecules/substances, which are capable of inhibiting and/or reducing an agonistic effect. A TMEFF2 antagonist comprises an endogenous substance, a compound, a small molecule, an agent or a drug that can interact with TMEFF2 protein and inhibit a maximal or complete physiological or a pharmacological response characteristic of TMEFF2. Alternatively, a TMEFF2 antagonist can interact with the TMEFF2 gene so as to inhibit its transcription. In another alternative, a TMEFF2 antagonist can interact with a TMEFF2 transcript, i.e. unspliced or spliced mRNA so as to inhibit its translation and/or to cause degradation of a TMEFF2 transcript. The term "gene" has been described above in the context of TMEFF2 agonists and is also applicable in the context of TMEFF2 antagonists.

A "TMEFF2 antagonist" encompasses a full antagonist and partial antagonists. A partial antagonist of TMEFF2 is an endogenous substance, a compound, a small molecule, an agent, or a drug which possesses affinity for TMEFF2, but unlike a full antagonist, will inhibit only a small degree of physiological or a pharmacological response characteristic of TMEFF2. Accordingly, a partial TMEFF2 antagonist is capable of incompletely blocking the action of agonists through, inter alia, a non-competitive mechanism.

The term "TMEFF2 antagonist" comprises competitive, non-competitive, functional and chemical antagonists as described, inter alia, in Mutschler, "Arzneimittelwirkungen" (1986), Wissenschaftliche Verlagsgesellschaft mbH, Stuttgart, Germany.

In the context of the present invention, a TMEFF2 antagonist is preferably a drug that does not provoke a response itself, but blocks agonist-mediated responses. It is a chemical entity that opposes the receptor-associated responses normally induced by another bioactive agent.

TMEFF2 Modulators of the CRH Signalling Pathway, Preferably of the cAMP Signalling Pathway A TMEFF2 modulator being a TMEFF2 agonist of the CRH signalling pathway, preferably the cAMP signalling pathway, is preferred. In the context of the present invention a TMEFF2 agonist of the CRH signalling pathway, preferably the cAMP signalling pathway, decreases the level of a constituent of the cAMP signalling pathway, preferably the CRH signalling pathway, and, thus, leads to a decrease in ACTH production.

A TMEFF2 antagonist of the CRH signalling pathway, preferably the cAMP signalling pathway, however, increases the level of a constituent of the cAMP signalling pathway, preferably the CRH signalling pathway, and, thus, leads to an increase in ACTH production.

Since it was surprisingly found that activation of TMEFF2 inhibits CRH signalling and ACTH production, the modulator of TMEFF2 used for the preparation of a pharmaceutical composition for treating an affective disorder and/or Cushing's Syndromes is preferably an agonist of the CRH signalling pathway, preferably one which is also a modulator of the Activin signalling pathway, in particular a modulator which is capable of reducing the binding between Activin and TMEFF2.

Said TMEFF2 agonist which is applied in the uses and methods described herein is preferably identified by the methods as described herein.

TMEFF2 activation can be measured by determining the level of a constituent of the cAMP signalling pathway, preferably the CRH signalling pathway as will be described hereinbelow in more detail.

The term "cyclic AMP (cAMP) signalling pathway" when used in the context of the present application involves defined signalling elements such as protein Gs, adenylyl cyclase, cAMP; protein kinase A/cAMP-dependent protein kinase (PKA), Rap1, B-Raf, MEK1, ERK1/2, CREB, Nur, POMC and/or ACTH. The elements of the cyclic AMP (cAMP) signalling pathway are reviewed by Kovalovsky and colleagues which define the elements of the two signalling pathways (Kovalovsky et al. (2002) Mol Endocrinol 16:1638-1651). It is known that Gs, adenylyl cyclase, protein kinase A/cAMP-dependent protein kinase, Rap1, B-Raf, MEK1, ERK1/2, CREB and Nur regulate POMC expression and ACTH production. The cyclic AMP signalling pathway can be regulated by different mechanisms such as binding of CRH to the CRH receptors. Thus, the term "CRH signalling pathway" is a preferred definition of the term "cyclic AMP (cAMP) signalling pathway" since it combines CRH and the CRH receptor with the cyclic AMP signalling pathway.

The term "level of a constituent of the cAMP signalling pathway" encompasses the amount of a constituent of the cAMP signalling pathway. The amount can be the amount of a transcript (including spliced and/or unspliced mRNA) encoding a constituent of the cAMP signalling pathway, the amount of protein of a constituent of the cAMP signalling pathway (including a pre-pro-form, pre-form, pro-form, mature form of a protein) and/or the amount of a constituent as such, e.g., the amount of cAMP.

The amount of a transcript can be determined be methods well known in the art, e.g., Northern Blot, RT-PCR, Realtime-PCR or the like or reporter gene assays as described in the appended Examples using luciferase. Of course, also other reporter genes such as GUS, GFP and the like can be used.

The amount of protein can be determined by methods well known in the art, e.g. Western Blot, ELISA, RIA etc.

The amount of a constituent as such, e.g. cAMP can be determined by methods well known in the art, e.g., using a cAMP detection kit as described in the appended Examples.

The term "level of a constituent of the cAMP signalling pathway" also includes the stability of a constituent of the cAMP signalling pathway. For example, the Gs protein being a constituent of the cAMP signalling pathway can also be influenced by a TMEFF2 modulator with respect to its stability. For example, a TMEFF2 agonist which activates TMEFF2 influences directly the inhibitory effect of TMEFF2 on the Gs protein insofar as the Gs protein is inhibited. Thereby, the dissociation of the Gs protein in its subunits is inhibited and, thus, the Gs protein is more stable.

Taking into account the above, TMEFF2 activation can, for example, be measured by G-protein activity detected using non-hydrolysable GTP-analogs. Alternatively, the dissociation of the beta-gamma subunits of the G-protein heterotrimers can be detected. Further downstream events can also be used to measure TMEFF2 activity such as levels of phosphatidylinositol-4,5-bisphosphate (PIP2) and inositol 1,4,5-triphosphate (IP3) using radiolabeled precursors, calcium levels using fluorescent dyes, adenylate cyclase activity, and accumulation of cAMP TMEFF2 activity can, for example, also be estimated by measuring protein-protein interactions of CRHR1 or other GPCRs with G proteins. Alternatively, TMEFF2 can inhibit the activity of adenylate cyclase directly.

TMEFF2 activity can, for example, also be monitored according to cAMP levels. TMEFF2 expressing cells, such as cells transfected with a TMEFF2 encoding polynucleotide can be treated for 1 hour with 100 nM CRH and then the cell lysates can be collected for measuring intracellular cAMP levels. Radioimmunological cAMP determination can be performed with a commercial RIA kit from NEN™ Life Science Products Inc. (Boston, Mass.).

The cAMP to be measured can be either the basal cAMP levels or the cAMP produced after stimulation of the CRH receptor or any other GPCR that acts through the protein Gs.

The accumulation of cAMP can be measured by radiometric proximity methods using scintillants and anti-cAMP antibodies. It can also be measured by fluorescence polarization in the presence of labeled cAMP and anti-cAMP antibodies or by time-resolved fluorescence using FRET. Further methods to detect cAMP accumulation include the amplified luminiscence assay (ALPHAScreen), enzyme complementation using beta-galactosidase or other multimeric enzymes, and electrochemiluminiscence.

Moreover, to measure TMEFF2 activation, cAMP inhibition can be measured by radioimmunoassays (as described in Example 8), ELISA, enzyme fragmentation complementation of beta-galactosidase or any other standard method to screen for GPCR ligands (Williams (2004) Nat Rev Drug Discov 3:125-135; Gabriel et al (2003) Assay Drug. Dev. Techn. 1:291-303).

Another way for measuring TMEFF2 activity is the use of cell lines expressing TMEFF2 which can be transfected with expression vectors for different G proteins to link TMEFF2 to adenylate cyclase, phospholipase C or to calcium channels. Cells can then be stimulated with CRH or other peptides or with compounds that activate the CRHR1 receptor or other GPCRs. The effect of TMEFF2 activation can be measured by the inhibition of cAMP production, phospholipase activity, or calcium currents using calcium dyes such as Fluo-4.

The cell lines which can be used for identifying TMEFF2 modulators can also express reporter constructs to measure the cAMP response by assessing the activity of the CREB, Nurr1 and/or POMC promoter, as demonstrated in examples 4, 6 and 7. By that, of course, TMEFF2 activity is measured.

NFAT-RE can be used in a similar way. For example, single or repeated CRE elements (cAMP responding elements) can be incorporated in the promoter of a gene whose expression can be measured easily such as luciferase. Alternatively, the CRE sequence would control the expression of a fluorescent protein such as the green fluorescent protein. Moreover, the level of any of the constituents of the cAMP signalling pathway can be measured in order to test for TMEFF2 activity. In particular, the level of Gs proteins, adenylyl cyclase, PKA, Rap1, B-Raf, MEK1, ERK1/2, CREB, Nur, POMC and ACTH may be tested.

Any of these biochemical activities can be tested to select TMEFF2 agonists and partial agonists from compound libraries, such as combinatorial libraries, using conventional methods of screening described herein. Of course, any of these biochemical activities can also be used for identifying a TMEFF2 antagonist. Moreover, any of these biochemical activities can be used to test whether a TMEFF2 polypeptide as described herein has TMEFF2 activity.

In a specific aspect of the invention compounds, small molecules, and agents that can act as agonists and partial agonists of TMEFF2 preferably with regard to its involvement in the CRH signalling pathway, preferably in the cAMP signalling pathway can be identified, characterised, and developed by measuring cAMP synthesis (cAMP being a constituent of the cAMP signalling pathway) in cells which express TMEFF2.

TMEFF2 Modulators of the Activin Signalling Pathway

As mentioned above, it was not only found that TMEFF2 is involved in the CRH signalling pathway, preferably the cAMP signalling pathway, but that it is also involved in the Activin signalling pathway. In the appended Examples it has been demonstrated that inhibition of TMEFF2 has antidepressant effects; see Example 13. Specifically, in order to demonstrate that inhibition of TMEFF2 has antidepressive effects, TMEFF2 function was specifically inhibited by delivering double stranded small interference RNA molecules (siRNA) into the brain of mice. Two guide cannula (23 gauge, length 10 mm) were bilaterally inserted into amygdala of the brain of male DBA/2Jico mice. Insertion of the guide cannula was done using a stereotaxic instrument. The coordinates, in relation to bregma, were −1.0 mm posterior, ±3.1 mm lateral, and −1.6 mm ventral. Following a 10 days recovery period, the mice were divided into two experimental groups that were injected with either control double stranded missense RNA (control), or with TMEFF2 specific double stranded siRNA (TMEFF2 siRNA). The sequence used for control missense siRNA was 5'-CGC GUA GAA GAU GAA GUU G TT-3' (SEQ ID NO: 15). The sequence used for TMEFF2 siRNA were 5'-UCA GAA GGA UCC UGU GCU A-3' (SEQ ID NO: 16) and 5'-CGG UUA CGA UGA CAG AGA A-3' (SEQ ID NO: 17). On day 10 after surgery, control or TMEFF2 siRNA were infused in unanaesthetised mice at a concentration of 0.2 nmol/µl, and a volume of 0.5 µl per side, over a period of 2 min per side, using specifically adapted infusion systems (33 gauge, length 12 mm). The animals were left undisturbed until behavioural testing took place.

The effects of TMEFF2 inhibition on depressive-like behaviour was assessed 24 hours (FST1) and 48 hours (FST2) after infusion of control or TMEFF2 siRNA according to the forced swim test paradigm. The forced swim test is a standard test that is based on the assumption that animals will normally try to escape from an aversive stimulus. When the aversive stimulation is inescapable, the animal will eventually stop trying to escape. Early cessation of attempts to escape is considered a rodent analogue of stress-induced depression. The test is used to determine the effectiveness of antidepressants, test new pharmaceutical compounds and validate animal models of depression (Porsolt et al., Arch. Int. Pharmacodym. 229 (1977), 327-336; Porsolt, Rev. Neurosci. 11 (2000), 53-58; Rénéric et al., Behav. Brain Res. 136 (2002), 521-532; Page et al., Psychopharmacology 165 (2003), 194-201; Kelliher et al., Psychoneuroendocrinology 28 (2003), 332-347). The test consists of placing a mouse for a period of 5 minutes into a glass cylinder containing water. Under such circumstances, the mouse cannot touch the bottom of the cylinder and is thus forced to swim. Time, latency and frequency of struggling versus floating are scored as behavioural parameters. Floating (i.e. movements made only for keeping balance and breath) is a passive behaviour associated with despair and represents a depressive-like symptom since the animal does not make any effort to actively cope with the stressful situation. Increased struggling (i.e. active attempts to escape) indicates active coping behaviour that can be interpreted as an improvement of depression-like symptoms. For example, treatment with serotonergic antidepressants reduce the total time spent floating (Borsini, Neurosci. Biobehav. Rev. 19 (1995), 377-395; Redrobe and Bourin, Psychopharmacology 138 (1998), 198-206, and in parallel increases the time of active behaviour (i.e. swimming or struggling; Lucki et al., Psychopharmacology 155 (2001), 315-322).

Inhibition of TMEFF2 by siRNA for periods of 24 and 48 hours was found to increase active escape attempts (i.e. increase in time of struggling) while a decrease in passive behaviour (i.e. decrease in time and frequency of floating) was measured when compared to control mice injected with control siRNA (FIG. 20). These results demonstrate that TMEFF2 inhibition has antidepressant properties that results in improvements of depression-like behaviour.

Thus, in accordance with the present invention, a TMEFF2 modulator of the Activin signalling pathway is preferred. A TMEFF2 modulator of the Activin signalling pathway is a compound which reduces the binding of Activin to TMEFF2 as described herein above. Accordingly, the activation of smad signalling may be more efficiently facilitated. Therefore, such a modulator may also be regarded as an agonist of TMEFF2 as regards its effect on the Activin signalling pathway, i.e. an agonist of the Activin signalling pathway.

As mentioned herein above, infusion of Activin into the hippocampus of animal models of depression has been shown to have antidepressant-like effects. Accordingly, it is assumed that a higher amount of Activin can more efficiently facilitate induction of the Activin signalling pathway. It is thus assumed, without being bound by theory, that reducing/inhibiting the binding of TMEFF2 to Activin also leads to a more efficient activation of the Activin signalling pathway; see FIG. 19.

Binding of Activin to type II Activin receptors results in the phosphorylation of the Smad proteins such as Smad2 and Smad3 which form homo- and heteromeric complexes with other proteins to bind DNA and regulate gene transcription. Consequently, Activin signalling can be monitored by assessing the binding and activation of Smads target genes. When phosphorylated by Activin receptors, Smad proteins such as Smad3 and Smad4 can bind to the specific DNA sequence CAGA (Dennler et al., 1998, EMBO J. 17:3091-3100; Lin et al., 2005, J Immunol 175:547-554; Luo et al., 2006, Proc Natl Acad Sci USA 103:18326-18331). In order to demonstrate that activation of TMEFF2 can inhibit Activin signalling and Smad activity, AtT-20 cells were transfected with an expression vector containing the human TMEFF2 cDNA and plasmid containing 12 copies of the CAGA sequence in front of a luciferase reporter. The human TMEFF2 cDNA was inserted into the expression vector pcDNA3.1 (Invitrogen).

AtT-20 cells were cotransfected with either 1 µg/ml human TMEFF2 or pcDNA3.1 control plasmid and 1 µg/ml 12×CAGA(SEQ ID NO: 20)-luciferase plasmid. The culture medium was replaced by DMEM+10% FCS 24 hours later and 48 hours after transfection, cells were treated with 50 ng/ml Activin for 6 hours in medium containing 0% FCS. Luciferase activity was then measured in a Wallac luminometer as previously described (Páez-Pereda et al., 2001, J. Clin. Invest. 108: 1123-1131).

Figure 21:
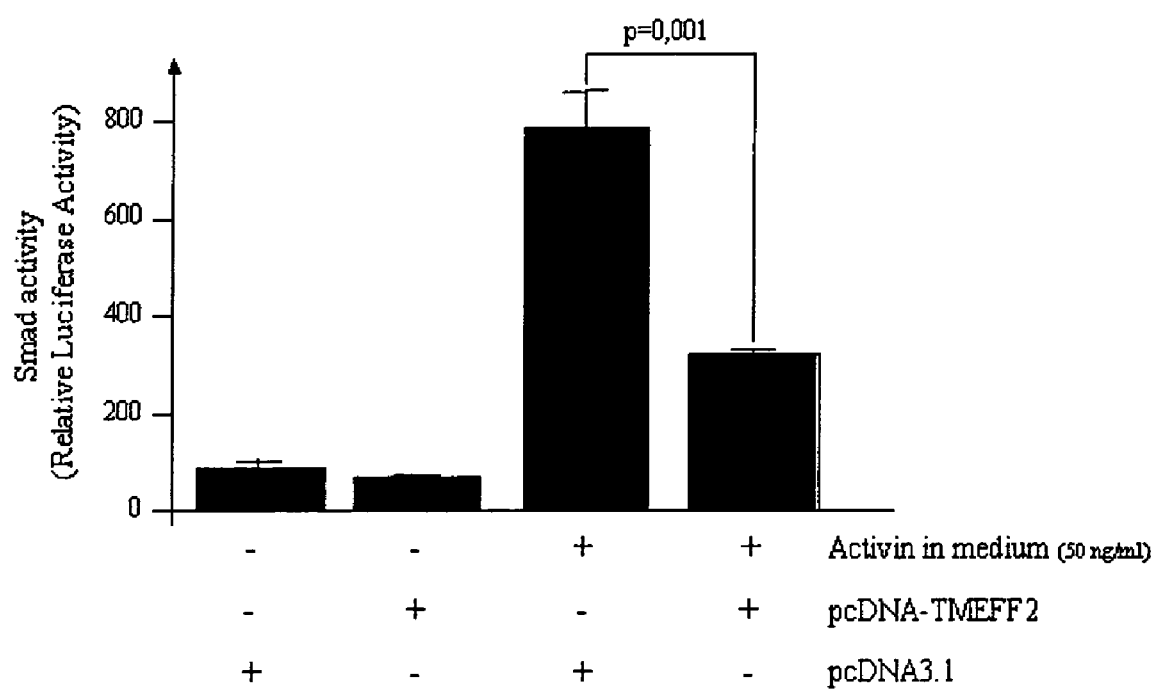

TMEFF2 expression reduced the transcriptional activation of the 12×CAGA(SEQ ID NO: 20)-luciferase plasmid by Activin (FIG. 21). This result demonstrates that TMEFF2 inhibits the Activin signalling pathway and activation of Smad proteins. Since active Activin signalling and increase Smad2 activity are known to be involved in antidepressant activity (Dow et al., 2005, J Neuroscience 25:4908-4916), a reduction of the expression of TMEFF2 can be used to treat affective disorders by promoting Activin signalling and Smad activity.

In view of the finding that TMEFF2 can act on the Activin signalling pathway, methods for identifying TMEFF2 modulators of the Activin signalling pathway are encompassed by the present invention.

It is believed that TMEFF2 follistatin-like domains are capable of binding to Activin through a protein-protein interaction.

Accordingly, methods for identifying TMEFF2 modulators of the Activin signalling pathway are envisaged. For example, screening assays that measure protein-protein interactions can be used to select compounds that disrupt TMEFF2 binding to Activin, such as scatchard analysis, scintillation proximity assays (SPA), Fluorescence resonance energy transfer (FRET), fluorescense polarisation, two hybrid assays, pull down assays, and others (for a review of screening methods, please see Warner et al., 2004, Curr Med Chem 11:721-730; Yin, Hamilton, 2005, Angew Chem Int Ed 44:4130-4163; Chène, 2006, ChemMedChem 1:400-411).

For example, Activin can be radioactively labelled with $I^{125}$ or $H^3$ and can be contacted with TMEFF2, fragments of TMEFF2 or cells that express TMEFF2. The fraction of free labelled Activin can be separated from the fraction bound to TMEFF2 by precipitation, filtration or column chromatography. The amount of radioactively labelled Activin that binds TMEFF2 can be estimated by measuring the radioactivity bound to TMEFF2 with a beta particle counter. The data can be analyzed using a Scatchard analysis. Alternatively, Activin can be labelled with fluorescent dyes or with fluorescent proteins and the amount of Activin bound to TMEFF2 can be measured by fluorescence detection.

Alternatively, the binding of Activin to TMEFF2 can be measured by "scintillation proximity assay" (SPA). In this case, TMEFF2 or fractions of TMEFF2 can be bound to SPA scintillation beads and Activin can be labelled for example with $I^{125}$ or $H^3$. If the two molecules are bound, the decay particles from the labelled Activin stimulate light emission from the SPA beads. The free Activin fraction does not produce light emission because it is not close enough to the beads. This assay can also be performed by labelling TMEFF2 and binding Activin to SPA beads. Details of such methods are well known in the art, see for example Wu and Lui, 2005, BioDrugs 19:383-392.

Yet another method to detect inhibitors of TMEFF2 is to measure TMEFF2 binding to Activin by FRET (Jares-Erijman and Jovin, 2003, Nat Biotechnol 21:1387-1395). This method consists in the energy transfer between two fluorescent dyes that are bound to two proteins, in this case Activin and TMEFF2. If Activin and TMEFF2 are bound together, the attached dyes transfer energy in such a way that one of the dyes absorbs the energy of the other and this produces an increase in the amount of fluorescence emitted by the acceptor dye. For example, one application of this principle is the Alphascreen platform. Alphascreen donor beads could be attached to Activin and Alphascreen acceptor beads could be attached to TMEFF2 or vice versa. The donor beads are stimulated by UV light with a particular wavelength. The emission of the activated donor stimulates the acceptor beads, which emit light in a different wavelength and this emission can be recorded. The acceptor beads are not activated if TMEFF2 and Activin are not bound.

Yet another possibility to screen for compounds that bind to TMEFF2 would be by using a functional assay. Free Activin binds to the Activin receptors and this results in receptor activation, phosphorylation and Smad activation. Therefore, the dissociation between TMEFF2 and Activin can be measured by an increase of receptor or Smad phosphorylation as well as an increase of Smad transcriptional activity. The Smad transcriptional activity can be measured for example with a reporter construct having a sequence 12×CAGA(SEQ ID NO: 20) cloned in the enhancer region of a Luciferase reporter (as described in detail in Example 14).

In the above described examples for identifying compounds that reduce the binding between Activin and TMEFF2, also cells which express TMEFF2 and/or Activin can be used, i.e. cell-based assays.

Expression of TMEFF2

"A cell which expresses TMEFF2" is a cell as described herein which is capable of expressing TMEFF2 as described herein. A cell which expresses TMEFF2 may naturally occur and, thus, expresses endogenously TMEFF2. Alternatively, such a cell may be prepared by genetically engineering said cell with a TMEFF2 encoding polynucleotide as described in more detail hereinbelow. Said cell may be selected from the group consisting of an animal cell, e.g., a mammalian cell, insect cell, amphibian cell or fish cell, a plant cell, fungal cell and bacterial cell as will be described in more detail hereinbelow. Preferably, said cell is an AtT-20 cell (Leung et al. (1982) Virchows Arch. 396: 303-312; ATCC Number CCL-89).

By way of example, in the methods for identifying TMEFF2 modulators, cell lines or primary cells that endogenously express TMEFF2, such as AtT-20 cells, can be used to measure TMEFF2 activity. Alternatively, TMEFF2 expression can be achieved by the transfection of expression vectors into cells lines that normally do not express TMEFF2 or the infection with modified viruses that express TMEFF2 as is explained herein in more detail. Constitutive activation of TMEFF2 can be used to screen for TMEFF2 modulators. Constitutive activation can be achieved by overexpression, natural genetic mutation or site-directed mutagenesis (Behan and Chalmers (2001) Curr. Opin. Drug Discov. Devel. 4:548-560; Chalmers and Behan (2002) Nat. Rev. Drug Discov. 1:599-608). Agonists, antagonists or inverse agonists can be further used through medicinal chemistry to find TMEFF2 modulators.

As described herein, TMEFF2 is membrane-bound (see also Example 3) and is also believed to be released into the extracellular matrix via proteolytic cleavage; see Horie et al. (2002), cited above. However, in the context of the present invention it is preferred that TMEFF2 is not released from the cells which express TMEFF2 and which are used for identifying a TMEFF2 modulator. Alternatively, it is preferred that at least a portion of TMEFF2 is membrane-bound, wherein said portion can modulate the cAMP signalling pathway, preferably the CRH signalling pathway and wherein said portion is accessible to the action of a TMEFF2 modulator, preferably a TMEFF2 agonist of the CRH signalling pathway, preferably the cAMP signalling pathway.

Example 5 provides guidance how to test whether TMEFF2 is membrane-bound or whether the afore described portion of TMEFF2 is still active and to thus evaluate whether the effect of a TMEFF2 modulator can be linked to the membrane-bound form or portion of TMEFF2.

Moreover, even if the extracellular portion of TMEFF2 may be released from cells by proteolytic cleavage releases, which then can act as a cytokine or growth factor capable of binding to the erbB family of EGF receptors (Horie et al. (2002) Genomics 67:146-152), it is noteworthy that this family of receptors does not act through the cAMP pathway but can regulate cell proliferation through kinases such as MAPK and PKC (Moghal and Sternberg (1999) Curr Opin Cell Biol 11:190-196). Hence, any effect caused by a soluble form of TMEFF2 is believed to not interfere with the cAMP signalling pathway through which the membrane-bound form of TMEFF2 is believed to act. Moreover, if desired the binding of the soluble TMEFF2 extracellular domain to the EGF receptor family can be inhibited by TMEFF2 antibodies that prevent the activation of the EGF receptor family or by antibodies against the soluble form of TMEFF2.

As described above in the context of the involvement of TMEFF2 in the CRH signalling pathway, preferably cAMP signalling pathway and in the Activin signalling pathway, respectively, it is possible to discriminate both signalling pathways. As mentioned above, the Activin signalling pathway does not act through the cAMP pathway and, thus, it is possible to discriminate between both signalling pathways.

For the purpose of expressing TMEFF2 in a cell, a nucleic acid molecule having a nucleotide sequence encoding TMEFF2 can be inserted into vector which, in turn, can be used to genetically engineer a host cell.

In particular, the nucleic acid molecules of the present invention may be inserted into several commercially available vectors. Nonlimiting examples include plasmid vectors compatible with mammalian cells, such as pUC, pBluescript (Stratagene), pET (Novagen), pREP (Invitrogen), pCRTopo (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRS-Vgpt, pRSVneo, pSV2-dhfr, pUCTag, pIZD35, pLXIN and pSIR (Clontech) and pIRES-EGFP (Clontech). Baculovirus vectors such as pBlueBac, BacPacz Baculovirus Expression System (CLONTECH), and MAXBAC™ Baculovirus Expression System, insect cells and protocols (Invitrogen) are available commercially and may also be used to produce high yields of biologically active protein. (see also, Miller (1993), Curr. Op. Genet. Dev., 3, 9; O'Reilly, Baculovirus Expression Vectors: A Laboratory Manual, p. 127). In addition, prokaryotic vectors such as pcDNA2; and yeast vectors such as pYes2 are nonlimiting examples of other vectors suitable for use with the present invention. For vector modification techniques, see Sambrook and Russel (2001), cited herein. Vectors can contain one or more replication and inheritance systems for cloning or expression, one or more markers for selection in the host, e.g., antibiotic resistance, and one or more expression cassettes.

The coding sequences inserted in the vector can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

Furthermore, the vectors may, in addition to the nucleic acid sequences of the invention, comprise expression control elements, allowing proper expression of the coding regions in suitable hosts. Such control elements are known to the artisan and may include a promoter, translation initiation codon, translation and insertion site or internal ribosomal entry sites (IRES) (Owens, Proc. Natl. Acad. Sci. USA 98 (2001), 1471-1476) for introducing an insert into the vector. Preferably, the nucleic acid molecule of the invention is operatively linked to said expression control sequences allowing expression in eukaryotic or prokaryotic cells. Particularly preferred are in this context control sequences which allow for correct expression in neuronal cells and/or cells derived from nervous tissue.

Control elements ensuring expression in eukaryotic and prokaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcoma virus), human elongation factor 1α-promoter, CMV enhancer, CaM-kinase promoter or SV40-enhancer.

For the expression for example in nervous tissue and/or cells derived therefrom, several regulatory sequences are well known in the art, like the minimal promoter sequence of human neurofilament L (Charron, J. Biol. Chem. 270 (1995), 25739-25745). For the expression in prokaryotic cells, a multitude of promoters including, for example, the tac-lac-promoter, the lacUV5 or the trp promoter, has been described. Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11.

An expression vector according to this invention is at least capable of directing the replication, and preferably the expression, of the nucleic acids and protein of this invention. Suitable origins of replication include, for example, the Col E1, the SV40 viral and the M 13 origins of replication. Suitable promoters include, for example, the cytomegalovirus (CMV) promoter, the lacZ promoter, the gai10 promoter and the *Autographa californica* multiple nuclear polyhedrosis virus (AcMNPV) polyhedral promoter. Suitable termination sequences include, for example, the bovine growth hormone, SV40, iacZ and AcMNPV polyhedral polyadenylation signals. Examples of selectable markers include neomycin, ampicillin, and hygromycin resistance and the like. Specifically-designed vectors allow the shuttling of DNA between different host cells, such as bacteria-yeast, or bacteria-animal cells, or bacteria-fungal cells, or bacteria invertebrate cells.

Beside the nucleic acid molecules of the present invention, the vector may further comprise nucleic acid sequences encoding for secretion signals. Such sequences are well known to the person skilled in the art. Furthermore, depending on the expression system used leader sequences capable of directing the expressed polypeptide to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a part thereof, into, inter alia, the extracellular membrane. Optionally, the heterologous sequence can encode a fusion protein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the proteins, antigenic fragments or fusion proteins of the invention may follow The present invention can not only be used to identify TMEFF2 agonists, but it can also be used to identify compounds, small molecules, and agents that are antagonists, and inverse agonists of TMEFF2. A prototype of such a procedure for identifying agonists, antagonists or inverse agonists of the CRH signalling pathway, preferably cAMP signalling pathway is presented in Example 8 and FIG. 5. A prototype for identifying compounds, small molecules, and agents that are TMEFF2 modulators of the Activin signalling pathway is presented in Example 15. Cells expressing TMEFF2 can be generated from AtT-20 cells, HEK293 cells, or other cell lines (e.g., HCN-1A, HCN-2, HIT-T15, RIN-m5F, betaTC3, PC12, HT22, SH-SY5Y, Neuro2A or CA77) which can be stably transfected with cDNA encoding TMEFF2 and plated in 12, 96 and 384 well plates. Nucleic acid sequences and cDNA of TMEFF2 are well known in the art, see for example Genbank Accession numbers NM_016192, NM_019790, BC034850, BC008973, AY412287, AY412288, AY412289, AB017270, and AB017269. A preferred TMEFF2 nucleic acid sequence or cDNA is a human TMEFF2 nucleic acid sequence or cDNA as shown in FIG. 16. Said cells are cultured in appropriate medium. Examples of such medium are well known in the art, see, for example Freshney, "Culture of Animal Cells: A Manual of Basic Technique, 4th edition, Wiley-Liss Publishing, 2000.

The term "a corresponding cell which does not express TMEFF2" includes cells which are essentially identical to cells which express TMEFF2 with the exception that these cells do not express TMEFF2, e.g., due to complete or partial inactivation of the gene encoding TMEFF2 achieved by a knock-out, siRNA or the like.

The term "contacting a cell" encompasses that a cell which expresses TMEFF2 or a corresponding cell which does not express TMEFF2 is contacted by any known means and methods in the art with a candidate compound.

The person skilled in the art can easily employ the compounds and the methods of this invention in order to elucidate the modulatory effects and/or characteristics of a test compound to be identified and/or characterized in accordance with any of the methods described herein.

The term "test compound" or "compound to be tested" refers to a molecule or substance or compound or composition or agent or any combination thereof to be tested by one or more screening method(s) of the invention as a putative TMEFF2 modulator. A test compound can be any chemical, such as an inorganic chemical, an organic chemical, a protein, a peptide, a carbohydrate, a lipid, or a combination thereof or any of the compounds, compositions or agents described herein. It is to be understood that the term "test compound" when used in the context of the present invention is interchangeable with the terms "test molecule", "test substance", "potential candidate", "candidate" or the terms mentioned hereinabove.

Accordingly, small peptides or peptide-like molecules as described hereinbelow are envisaged to be used in the method for identifying a TMEFF2 modulator. Such small peptides or peptide-like molecules bind to and occupy the active site of a protein thereby making the catalytic site inaccessible to substrate such that normal biological activity is prevented. Moreover, any biological or chemical composition(s) or substance(s) may be envisaged as TMEFF2 modulator. The modulator function of the modulator can be measured by methods described herein. Such methods comprise interaction assays, like immunoprecipitation assays, ELISAs, RIAs as well as specific inhibition/activation, like the assays provided in the appended Examples. In the context of the present application it is envisaged that cells expressing TMEFF2 as described herein are used in the screening assays. It is also envisaged that elements of the cAMP signalling pathway, preferably the CRH signalling pathway, may be used, e.g., Gs proteins, adenylyl cyclase, cAMP, PKA, Rap1, B-Raf, MEK1, ERK1/2, CREB, Nur, POMC and ACTH. Said elements may be present in whole cell extracts of cells expressing TMEFF2 or said elements may be purified, partially purified or recombinantly expressed as described hereinbelow.

Also preferred potential candidate molecules or candidate mixtures of molecules to be used when contacting a cell expressing TMEFF2 or an element of the cAMP signalling pathway, preferably the CRH signalling pathway or an element of the Activin signalling pathway such as a serine/threonine receptor comprised of a type II ligand binding receptor ActRIIA and ActRIIB and a type I signal transducing receptor (ALK 4) Smad 2, Smad 3 and other Smad proteins, may be, inter alia, substances, compounds or compositions which are of chemical or biological origin, which are naturally occurring and/or which are synthetically, recombinantly and/or chemically produced. Thus, candidate molecules may be proteins, protein-fragments, peptides, amino acids and/or derivatives thereof or other compounds, such as ions, which bind to and/or interact with TMEFF2 or other elements of the cAMP signalling pathway, preferably the CRH signalling pathway or elements of the Activin signalling pathway. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means. Examples of further libraries which can be used for screening TMEFF2 modulators are found at ambinter.com, ibscreen.com, chembridge.com/chembridge/products.html, asinex.com/prod/download.html.

In addition, the generation of chemical libraries is well known in the art. Chemical libraries encompass numerous chemical classes, though typically they are organic molecules, preferably small organic compounds having a molecular weight of more than 50 and less than about 2,500 Daltons. Candidate compounds, small molecules, and agents comprise functional groups necessary for structural interaction with proteins, particularly hydrogen bonding, and typically include at least an amine, carbonyl, hydroxyl or carboxyl group, preferably at least two of the functional chemical groups. The candidate compounds, small molecules, and agents often comprise carbocyclic or heterocyclic structures and/or aromatic or polyaromatic structures substituted with one or more of the above functional groups.

Candidate compounds, small molecules, and agents are also found among biomolecules including peptides, amino acids, saccharides, fatty acids, steroids, purines, pyrimidines, nucleic acids and derivatives, structural analogs or combinations thereof. Candidate compounds, small molecules, and agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

For example, combinatorial chemistry is used to generate a library of compounds to be screened in the assays described herein. A combinatorial chemical library is a collection of diverse chemical compounds generated by either chemical synthesis or biological synthesis by combining a number of chemical "building block" reagents. For example, a linear combinatorial chemical library such as a polypeptide library is formed by combining amino acids in every possible combination to yield peptides of a given length. Millions of chemical compounds can theoretically be synthesized through such combinatorial mixings of chemical building blocks. For example, one commentator observed that the systematic, combinatorial mixing of 100 interchangeable chemical building blocks results in the theoretical synthesis of 100 million tetrameric compounds or 10 billion pentameric compounds. (Gallop, Journal of Medicinal Chemistry, Vol. 37, No. 9, 1233-1250 (1994)). Other chemical libraries known to those in the art may also be used, including natural product libraries. Once generated, combinatorial libraries are screened for compounds that possess desirable biological properties. For example, compounds which may be useful as drugs or to develop drugs would likely have the ability to bind to the target protein identified, expressed and purified as described herein.

In the context of the present invention, libraries of compounds are screened to identify compounds that function as modulators of TMEFF2. First, a library of small molecules is generated using methods of combinatorial library formation well known in the art. U.S. Pat. Nos. 5,463,564 and 5,574,656 are two such teachings. Then the library compounds are screened to identify those compounds that possess desired structural and functional properties. U.S. Pat. No. 5,684,711, discusses a method for screening libraries. To illustrate the screening process, the target cell or gene product and chemical compounds of the library are combined and permitted to interact with one another. A labeled substrate is added to the incubation. The label on the substrate is such that a detectable signal is emitted from metabolized substrate molecules. The emission of this signal permits one to measure the effect of the combinatorial library compounds on the activity of TMEFF2 by comparing it to the signal emitted in the absence of combinatorial library compounds. The characteristics of each library compound are encoded so that compounds demonstrating activity on TMEFF2 can be analyzed and features common to the various compounds identified can be isolated and combined into future iterations of libraries. Once a library of compounds is screened, subsequent libraries are generated using those chemical building blocks that possess the features shown in the first round of screen to have activity against the target cell/enzyme. Using this method, subsequent iterations of candidate compounds will possess more and more of those structural and functional features required to inhibit the function of the target cell/enzyme, until a group of (enzyme) inhibitors with high specificity for the enzyme can be found. These compounds can then be further tested for their safety and efficacy as antibiotics for use in animals, such as mammals. It will be readily appreciated that this particular screening methodology is exemplary only. Other methods are well known to those skilled in the art. For example, a wide variety of screening techniques are known for a large number of naturally-occurring targets when the biochemical function of the target protein is known. For example, some techniques involve the generation and use of small peptides to probe and analyze target proteins both biochemically and genetically in order to identify and develop drug leads. Such techniques include the methods described in PCT publications No. WO 99/35494, WO 98/19162, WO 99/54728.

Preferably, candidate agents encompass numerous chemical classes, though typically they are organic molecules, preferably small organic compounds having a molecular weight of more than 50 and less than about 2,500 Daltons, preferably less than about 750, more preferably less than about 350 Daltons.

Candidate agents may also comprise functional groups necessary for structural interaction with proteins, particularly hydrogen bonding, and typically include at least an amine, carbonyl, hydroxyl or carboxyl group, preferably at least two of the functional chemical groups. The candidate agents often comprise carbocyclic or heterocyclic structures and/or aromatic or polyaromatic structures substituted with one or more of the above functional groups.

Exemplary classes of candidate agents may include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like. Other methods of stabilization may include encapsulation, for example, in liposomes, etc.

As mentioned above, candidate agents are also found among biomolecules including peptides, amino acids, saccharides, fatty acids, steroids, purines, pyrimidines, nucleic acids and derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Other candidate compounds to be used as a starting point for the screening of modulators of TMEFF2 are aptamers, aptazymes, RNAi, shRNA, RNAzymes, ribozymes, antisense DNA, antisense oligonucleotides, antisense RNA, antibodies, affybodies, trinectins, anticalins, or the like compounds. Yet, these candidate compounds are not only starting points, they are preferably TMEFF2 agonists, antagonists or modulators actingon the Activin signaling pathway. It is envisaged that a compound of interest is a molecule that is capable of acting as a TMEFF2 agonist on the CRH signalling pathway, preferably cAMP signalling pathway and simultaneously reduces the binding of Activin to TMEFF2. It is envisaged that such a compound of interest could be, e.g., a small molecule or a peptide or protein which is capable of binding to TMEFF2, thereby reducing the binding of Activin to TMEFF2 and simultaneously acting in an agonistsic fashion on TMEFF2 so that TMEFF2 is capable of acting as an agonist on the CRH signalling pathway, preferably cAMP signalling pathway.

An siRNA approach is, for example, disclosed in EP-B1 1 214 945, EP-B1 1 144 623 or Elbashir ((2001), Nature 411, 494-498)). It is also envisaged in accordance with this invention that for example short hairpin RNAs (shRNAs) are employed in accordance with this invention as pharmaceutical composition. The shRNA approach for gene silencing is well known in the art and may comprise the use of st (small temporal) RNAs; see, inter alia, Paddison (2002) Genes Dev. 16, 948-958. As mentioned above, approaches for gene silencing are known in the art and comprise "RNA"-approaches like RNAi or siRNA. Successful use of such approaches has been shown in Paddison (2002) Genes Dev. 16:948-58, Elbashir (2002) Methods 26, 199-213; Novina (2002) Mat. Med. Jun. 3, 2002; Donze (2002) Nucl. Acids Res. 30, e46; Paul (2002) Nat. Biotech 20, 505-508; Lee (2002) Nat. Biotech. 20, 500-505; Miyagashi (2002) Nat. Biotech. 20, 497-500; Yu (2002) PNAS 99, 6047-6052 or Brummelkamp (2002), Science 296, 550-553. These approaches may be vector-based, e.g. the pSUPER vector, or RNA polIII vectors may be employed as illustrated, inter alia, in Yu (2002) loc. cit.; Miyagishi (2002) loc. cit. or Brummelkamp (2002) loc. cit.

Accordingly, the person skilled in the art is readily in a position to have candidate compounds at his disposal which can be used in the screening methods for modulators of TMEFF2 as a basis to, inter alia, improve or further develop the capability of such compounds to modulate TMEFF2. Accordingly, the person skilled in the art can readily modify such compounds by methods known in the art to improve their capability of acting as a modulator in the sense of the present invention. The capability of one or more of the aforementioned compounds to modulate TMEFF2 is tested as described hereinabove.

Another technique for drug screening, which may be used, provides for high throughput screening of compounds having suitable binding affinity to the TMEFF2 protein as described in published PCT application WO 84/03564. In this method, as applied to the proteins of the invention large numbers of different small test compounds, e.g. aptamers, peptides, low-molecular weight compounds etc., are provided or synthesized on a solid substrate, such as plastic pins or some other surface. The test compounds are reacted with the proteins or fragments thereof, and washed. Bound proteins are then detected by methods well known in the art. Purified proteins can also be coated directly onto plates for use in the aforementioned drug screening techniques. Alternatively, non-neutralizing antibodies can be used to capture the peptide and immobilize it on a solid support. In another embodiment, one may use competitive drug screening assays in which neutralizing antibodies capable of binding the protein specifically compete with a test compound for binding the protein. In this manner, the antibodies can be used to detect the presence of any peptide, which shares one or more antigenic determinants with the protein.

The present invention envisages in a furthermore preferred embodiment that the compound to be tested for its capability to modulate TMEFF2 is synthetically, recombinantly and/or chemically produced as is described in detail hereinabove.

Moreover, in a preferred embodiment TMEFF2 modulators are screened in a high throughput screening assay. High-throughput screening (HTS) is the process of testing a large number of diverse chemical structures against disease targets to identify 'hits'. Compared to traditional drug screening methods, HTS is characterized by its simplicity, rapidness, low cost, and high efficiency, taking the ligand-target interactions as the principle, as well as leading to a higher information harvest. As a multidisciplinary field, HTS involves an automated operation-platform, highly sensitive testing system, specific screening model (in vitro), an abundant components library, and a data acquisition and processing system. Various technologies, especially the novel technologies such as fluorescence, nuclear-magnetic resonance, affinity chromatography, surface plasmon resonance, and DNA microarray, are now available, and the screening of more than 100 000 samples per day is already possible (see for example, Liu et al. (2004) Am. J. Pharmacogenomics 4:263-276). High-throughput screens can be carried out robotically in 1536- or 3456-well titer plates on small (submicrogram) amounts of compound (dissolved in the submicroliter volumes). Combinatorial chemistry can supply huge numbers of compounds in a short period of time, which provides an increased number of hits i.e. compounds that elicit a predetermined level of activity in the bioassay (Silverman, "The organic chemistry of drug design and drug action" 2nd ed. Elsevier Academic Press, 2004).

High-throughput screening methods are also described in U.S. Pat. Nos. 5,585,277 and 5,679,582, in U.S. Ser. No. 08/547,889, and in the published PCT application PCT/US96/19698, and may be used for identifying a TMEFF2 modulator as described herein. High-throughput screening methods and similar approaches which are known in the art (Spencer, Biotechnol. Bioeng. 61 (1998), 61-67; Oldenburg, Annu. Rev. Med. Chem. 33 (1998), 301-311) carried out using 96-well, 384-well, 1536-well (and other) commercially available plates. In this method, large numbers of different small test compounds, e.g. aptamers, peptides, low-molecular weight compounds as described herein, are provided or synthesized on a solid substrate, such as plastic pins or some other surface. Further methods to be employed in accordance with the present invention comprise, but are not limited to, homogenous fluorescence readouts in high-throughput screenings (as described, inter alia, in Pope, Drug Discovery Today 4 (1999), 350-362).

The term "increases" or "decreases" as used herein in the context of screening a TMEFF2 modulator defines the increase or decrease, respectively, of the level of a constituent of the CRH signalling pathway, preferably a constituent of the cAMP signalling pathway, in a cell which expresses TMEFF2 when compared to a corresponding cell which does not express TMEFF2. Thus, the level of a constituent of the CRH signalling pathway, preferably a constituent of the cAMP signalling pathway, present in a cell which does not express TMEFF2 is understood to present the "reference value" to which an increased or decreased level of a constituent of the CRH signalling pathway, preferably a constituent of the cAMP signalling pathway, should be compared when evaluating whether a test compound increases or decreases the level a constituent of the CRH signalling pathway, preferably a constituent of the cAMP signalling pathway.

A decrease or increase of the reference value is thus indicative whether a test compound acts as an agonist or antagonist of TMEFF2 and, thus, as a possible inhibitor or activator of the CRH signalling pathway, preferably the cAMP signalling pathway. Of course, it is envisaged that the effect of a test compound on TMEFF2 and, thus, on the CRH signalling pathway, preferably the cAMP signalling pathway, will be further investigated by, e.g., comparing the effect of said test compound on cells of a healthy individual, i.e. an individual not having an affective disorder and/or Cushing's Syndromes to see whether said test compound increases or decreases the level of a constituent of the CRH signalling pathway, preferably a constituent of the cAMP signalling pathway. Namely, it is assumed that a healthy subject not suffering from an affective disorder and/or Cushing's Syndromes has a normal level of constituents of the CRH signalling pathway, preferably a constituent of the cAMP signalling pathway, and, thus, a normal signal transduction as regards perception and transduction of stimuli via the CRH receptor. "Normal" when used herein in connection with the level of a constituent of CRH signalling pathway, preferably a constituent of the cAMP signalling pathway, means a level of a constituent of CRH signalling pathway, preferably a constituent of the cAMP signalling pathway, present in a sample from a subject which does not have an affective disorder and/or Cushing's Syndromes.

As is illustrated herein in the appended Examples, e.g., in Examples 4, 6, 7 or 8 inhibition of TMEFF2 enhances CRH effects on POMC, Nur and CREB transcriptional activity and increases the CRH-induced stimulation of cAMP. Accordingly, it will be understood that the increase of a constituent of the CRH signalling pathway, preferably a constituent of the cAMP signalling pathway, mediated by a test compound which acts as a modulator, in particular as an antagonist of TMEFF2, increases the signal transduction through the CRH signalling pathway, preferably the cAMP signalling pathway, by increasing the level of one or more of the constituents of the CRH signalling pathway, preferably a constituent of the cAMP signalling pathway. An increase of a constituent of the CRH signalling pathway, preferably a constituent of the cAMP signalling pathway, is thus believed to lead to an increase of the level of ACTH which is desirable if the ACTH level in a subject is lower than the normal level. Examples of diseases that are associated with low ACTH levels include secondary hypoadrenalism, and ACTH deficiency. Secondary hypoadrenalism is commonly observed in patients with Cushing's disease following successful, selective removal of the ACTH-secreting pituitary adenoma. ACTH deficiency can be due to a range of congenital disorders or be acquired due to structural or functional diseases of the pituitary or, less commonly, the hypothalamus (Cooper and Stewart (2005) Rev. Endocr. Metab. Dis. 6:47-54). The commonest cause of ACTH deficiency is recent use of therapeutic glucocorticoids since approximately 1% of the population in Western countries are taking oral glucocorticoids at any one time. ACTH deficiency is an important condition that can be life threatening if not recognised. A decline in the concentration of ACTH in the blood leads to a reduction in the secretion of adrenal hormones, resulting in adrenal insufficiency (hypoadrenalism). Adrenal insufficiency leads to weight loss, lack of appetite (anorexia), weakness, nausea, vomiting, and low blood pressure (hypotension).

Consequently, an antagonist of TMEFF2 in particular of the CRH signalling pathway, preferably cAMP pathway, can be used to elevate ACTH levels for the treatment of secondary hypoadrenalism, or ACTH deficiency.

Accordingly, it is envisaged that the increase of the level of a constituent of the CRH signalling pathway, preferably a constituent of the cAMP signalling pathway, mediated by a TMEFF2 antagonist is at least 1%, 2%, 3%, 4%, 5%, 10%, 20%, 30%, 40%, 50%, 60%, 70%, 80%, 90% or even 100% when compared to level of a constituent of the CRH signalling pathway, preferably a constituent of the cAMP signalling pathway, that is achieved without the addition of said TMEFF2 antagonist.

As demonstrated in Example 11, activation of TMEFF2 inhibits CRH signalling and ACTH production. Accordingly, it is believed that a decrease of a constituent of the CRH signalling pathway, preferably a constituent of the cAMP signalling pathway, mediated by a test compound which acts as a modulator, in particular as an agonist of TMEFF2 decreases the signal transduction through the CRH signalling pathway, preferably the cAMP signalling pathway, by decreasing the level of one or more of the constituents of the CRH signalling pathway, preferably a constituent of the cAMP signalling pathway. A decrease of a constituent of the CRH signalling pathway, preferably a constituent of the cAMP signalling pathway, is thus believed to lead to a decrease in the level of ACTH which may desirable if the ACTH level in a subject is higher than the normal level/natural state.

Accordingly, it is envisaged that the decrease of the level of a constituent of the CRH signalling pathway, preferably a constituent of the cAMP signalling pathway, mediated by a TMEFF2 agonist is at least 1%, 2%, 3%, 4%, 5%, 10%, 20%, 30%, 40%, 50%, 60%, 70%, 80%, 90% or even 100% when compared to level of a constituent of the CRH signalling pathway, preferably a constituent of the cAMP signalling pathway, that is achieved without the addition of said TMEFF2 agonist.

The present invention also relates to the use of a TMEFF2 agonist preferably a TMEFF2 agonist of the CRH signalling pathway, preferably of the cAMP signalling pathway, for the preparation of a pharmaceutical composition for treating an affective disorder and/or preferably Cushing's Syndromes. Also, said TMEFF2 agonist can be used in a method of treating an affective disorder and/or preferably Cushing's Syndromes comprising administering a therapeutically effective amount of said TMEFF2 agonist to a subject in need thereof. The TMEFF2 agonist preferably a TMEFF2 agonist of the CRH signallingp pathway, preferably the cAMP signalling pathway, to be applied in the uses and methods of treatment can be any of the herein described compounds. Preferably, said TMEFF2 agonist is identified by the methods described herein.

In the uses and methods for the treatment of affective disorders and/or Cushing's Syndromes, the TMEFF2 agonist preferably a TMEFF2 agonist of the CRH signalling pathway, preferably of the cAMP signalling pathway, to be applied as described herein leads preferably to the decrease of the level of a constituent of the CRH signalling pathway, preferably a constituent of the cAMP signalling pathway, as described herein.

In the uses and methods for the treatment of affective disorders a TMEFF2 modulator of the Activin signalling pathway is applied. However, as mentioned herein, also a TMEFF2 agonist or antagonist of the CRH signalling pathway can act as a TMEFF2 modulator of the Activin signalling pathway and can thus be useful in the treatment of affective disorders.

The increase or decrease of the level of a constituent of the CRH signalling pathway, preferably a constituent of the cAMP signalling pathway or the reduction of binding of Activin to TMEFF2 and thus the more efficient activation of the Activin signalling pathway, will also depend on the dosage and on the way of administration of the TMEFF2 agonist or antagonist, respectively. The dosage regimen utilizing the TMEFF2 agonist or antagonist of the present invention is therefore selected in accordance with a variety of factors including type, species, age, weight, sex and medical condition of the patient; the severity of the condition to be treated; the route of administration; and the particular compound employed. It will be acknowledged that an ordinarily skilled physician or veterinarian can easily determine and prescribe the effective amount of the compound required to prevent, counter or arrest the progress of the condition. Test-systems which are suitable for such purposes, i.e. which allow to measure the effect of a TMEFF2 agonist or antagonist are described herein.

In the context of the present invention the term "subject" means an individual in need of a treatment of an affective disorder and/or Cushing's Syndromes. Preferably, the subject is a vertebrate, even more preferred a mammal, particularly preferred a human.

The term "administered" means administration of a therapeutically effective dose of a TMEFF2 agonist or modulator to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art. The uses methods for treatment described herein are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents maybe administered alone or in combination with other treatments.

The administration of the pharmaceutical composition can be done in a variety of ways as discussed above, including, but not limited to, intracerebral, orally, subcutaneously, intravenously, intra-arterial, intranodal, intramedullary, intrathecal, intraventricular, intranasally, intrabronchial, transdermally, intranodally, intrarectally, intraperitoneally, intramuscularly, intrapulmonary, vaginally, rectally, or intraocularly. In some instances, for example, in the treatment of wounds and inflammation, the candidate agents may be directly applied as a solution dry spray.

For oral administration, the pharmaceutical composition of a TMEFF2 agonist or partial agonist or antagonist or modulator may take the form of, for example, tablets, films or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration may take the form of, for example, solutions, syrups, or suspensions, or may be presented as a dry product for constitution with water or other suitable vehicle before use. Such liquid preparation may be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, soric acids). The preparations may also contain buffer salts, flavouring, coloring and sweetening agents as deemed appropriate. Preparations for oral administration may be suitably formulated to give controlled release of the agent modulating TMEFF2 activity.

For administration by inhalation, a TMEFF2 agonist or partial agonist or antagonist or modulator may conveniently be delivered in the form of an aerosol spray presentation from a pressurised pack or a nebulizer, with the use of a suitable propellant (e.g., dichlorodifluoromethane, trichlorofluoromethane, dichlorotetrafluoroethane, carbon dioxide or other suitable gas). In the case of a pressurised aerosol, the dosage unit may be determined by providing a valve to deliver a metered amount. Capsules and cartridges of, for example, gelatine, for use in an inhaler or insufflator may be formulated containing a powder mix of the TMEFF2 activity modulating agent and a suitable powder base such as lactose or starch.

A TMEFF2 agonist or partial agonist or antagonist or modulator may be formulated for parenteral administration by injection, for example, by bolus injection or continuous infusion. Site of injections include intra-venous, intra-peritoneal or sub-cutaneous. Formulations for injection may be presented in units dosage form (e.g., in phial, in multi-dose container), and with an added preservative. A TMEFF2 agonist or partial agonist or antagonist or modulator may take such forms as suspensions, solutions or emulsions in oily or aqueous vehicles, and may contain formulatory agents such as suspending, stabilizing, or dispersing agents. Alternatively, the agent may be in powder form for constitution with a suitable vehicle (e.g., sterile pyrogen-free water) before use.

A TMEFF2 agonist or partial agonist or antagonist or modulator may, if desired, be presented in a pack, or dispenser device which may contain one or more unit dosage forms containing the said agent. The pack may for example comprise metal or plastic foil, such as blister pack. The pack or dispenser device may be accompanied with instruction for administration.

Dosage, pharmaceutical preparation and delivery of a TMEFF2 agonist or partial agonist or antagonist or modulator for the treatment of affective disorders and/or Cushing's Syndromes may be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. Thus, the TMEFF2 modulating agent and its physiologically acceptable salts and solvates may be formulated for administration by inhalation, insufflation (either through the mouth, or nose), oral, buccal, parenteral, or rectal administration.

The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, however, during progression of the treatment the dosages can be given in much longer time intervals and in need can be given in much shorter time intervals, e.g., daily. In a preferred case the immune response is monitored using herein described methods and further methods known to those skilled in the art and dosages are optimized, e.g., in time, amount and/or composition. If the regimen is a continuous infusion, it should also be in the range of 1 µg to 10 mg units per kilogram of body weight per minute, respectively. Progress can be monitored by periodic assessment. The pharmaceutical composition of the invention may be administered locally or systemically. Administration will preferably be parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium ion solution, Ringer's dextrose, dextrose and sodium ion, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the aforementioned compounds, preferably in purified form, together with a suitable amount of carrier so as to provide the form for proper administration to the patient. The formulation should suit the mode of administration.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The pharmaceutical composition is preferably designed for the application in gene therapy. The technique of gene therapy has already been described above in connection with the nucleic acid molecules of the invention and all what has been said there also applies in connection with the pharmaceutical composition. For example, the nucleic acid molecule in the pharmaceutical composition is preferably in a form which allows its introduction, expression and/or stable integration into cells of an individual to be treated.

As described herein, the TMEFF2 agonist which is preferably a TMEFF2 agonist of the CRH signalling pathway, preferably of the cAMP signalling pathway can be identified by the methods described herein. Since is demonstrated in Example 11 herein, that overexpression of a polynucleotide encoding TMEFF2 leads to the activation of TMEFF2 and, thus, to the inhibition of CRH signalling and ACTH production, a TMEFF2 agonist, preferably of the CRH signalling pathway, preferably the cAMP signalling pathway can also be a TMEFF2 polynucleotide or a TMEFF2 polypeptide as described herein. Moreover, a TMEFF2 agonist or antagonist, preferably a TMEFF2 agonist or antagonist of the CRH signalling pathway, preferably of the cAMP signalling pathway can be a TMEFF2 antibody, preferably an agonistic or antagonistic antibody. Of course, a modulator, preferably of the Activin signalling pathway can be a TMEFF2 antibody, e.g. an antibody which interferes with the binding of Activin and TMEFF2. It can be tested by the skilled person whether an antibody is agonistic or antagonistic for TMEFF2 by applying the tests for TMEFF2 activity as described herein.

Hence, an antibody which is agonistic or antagonistic for TMEFF2 with regard to its involvement in the CRH signalling pathway, preferably cAMP signalling pathway can also reduce the binding of Activin to TMEFF2. Accordingly, such an antibody is an example that a TMEFF2 agonist or antagonist of the CRH signalling pathway, preferably cAMP The antibody of the present invention can be, for example, polyclonal or monoclonal. The term "antibody" also comprises derivatives or fragments thereof which still retain the binding specificity. Techniques for the production of antibodies are well known in the art and described, e.g. in Harlow and Lane "Antibodies, A Laboratory Manual", CSH Press, Cold Spring Harbor, 1988.

The present invention furthermore includes chimeric, single chain and humanized antibodies, as well as antibody fragments, like, inter alia, Fab fragments. Antibody fragments or derivatives further comprise F(ab')2, Fv or scFv fragments; see, for example, Harlow and Lane, loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies to polypeptide(s) of this invention. Also, transgenic animals may be used to express humanized antibodies to polypeptides of this invention. Most preferably, the antibody of this invention is a monoclonal antibody. For the preparation of monoclonal antibodies, any technique which provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Techniques describing the production of single chain antibodies (e.g., U.S. Pat. No. 4,946,778) can be adapted to produce single chain antibodies to immunogenic polypeptides as described above. Furthermore, transgenic mice may be used to express humanized antibodies directed against said immunogenic polypeptides. It is in particular preferred that the antibodies/antibody constructs as well as antibody fragments or derivatives to be employed in accordance with this invention or capable to be expressed in a cell. This may, inter alia, be achieved by direct injection of the corresponding proteineous molecules or by injection of nucleic acid molecules encoding the same. Furthermore, gene therapy approaches are envisaged. Accordingly, in context of the present invention, the term "antibody molecule" relates to full immunoglobulin molecules as well as to parts of such immunoglobulin molecules. Furthermore, the term relates, as discussed above, to modified and/or altered antibody molecules, like chimeric and humanized antibodies. The term also relates to monoclonal or polyclonal antibodies as well as to recombinantly or synthetically generated/synthesized antibodies. The term also relates to intact antibodies as well as to antibody fragments thereof, like, separated light and heavy chains, Fab, Fab/c, Fv, Fab', F(ab')$_2$. The term "antibody molecule" also comprises bifunctional antibodies and antibody constructs, like single chain Fvs (scFv) or antibody-fusion proteins. It is also envisaged in context of this invention that the term "antibody" comprises antibody constructs which may be expressed in cells, e.g. antibody constructs which may be transfected and/or transduced via, inter alia, viruses or vectors. It is in particular envisaged that such antibody constructs specifically recognize the polypeptides of the present invention. It is, furthermore, envisaged that said antibody construct is employed in gene therapy approaches.

In one aspect of the invention, activation of TMEFF2 for the treatment of Cushing's Syndromes can be achieved by introducing nucleic acids sequences comprising a sequence encoding the TMEFF2 protein by way of gene therapy. Gene therapy, which is based on introducing therapeutic genes (for example for vaccination) into cells by ex-vivo or in-vivo techniques is one of the most important applications of gene transfer. Any of the methods for gene therapy available in the art can be used in the present invention. For general reviews of the methods of gene therapy, see Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; Morgan and Anderson (1993) Ann. Rev. Biochem. 62: 191-217; May (1993) TIBTECH 11 (5):155-215; Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957; Schaper, Current Opinion in Biotechnology 7 (1996), 635-640 or Verma, Nature 389 (1997), 239-242; Benitez and Segovia (2003) Curr. Gene Ther. 3:127-145. Methods commonly known in the art of recombinant DNA technology that can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY. Dosages will vary but a preferred dosage for intravenous administration of DNA is from approximately $10^6$ to $10^{12}$ copies of the DNA molecule.

In the present invention, a TMEFF2 nucleic acid is part of an expression vector that expresses a functional TMEFF2 protein. In particular, a TMEFF2 nucleic acid has a promoter operably linked to the TMEFF2 coding region, such a promoter can be inducible or constitutive, and optionally, tissue-specific. Furthermore a TMEFF2 nucleic acid molecule can be used in which the TMEFF2 coding sequences and any other desired sequences are flanked by regions that promote homologous recombination at a desired site in the genome, thus providing for intrachromosomal expression of the TMEFF2 nucleic acid (Koller and Smithies (1989) Proc. Natl. Acad. Sci. USA 86:8932-8935; Zijlstra et al. (1989) Nature 342:435-438). Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

A TMEFF2 nucleic acid can be directly administered in vivo, where it is expressed to produce an active TMEFF2 protein. This can be accomplished by any of numerous methods known in the art, for example by constructing it as part of an appropriate nucleic acid expression vector and administering it so that it becomes intracellular, for example by infection using a defective or attenuated retroviral or other viral vector (see U.S. Pat. No. 4,980,286), or by direct injection of naked DNA, or by use of microparticle bombardment (for example by using a gene gun; Biolistic, Dupont), or coating with lipids or cell-surface receptors or transfecting agents, encapsulation in liposomes, microparticles, or microcapsules, or by administering it in linkage to a peptide that is known to enter the nucleus, by administering it in linkage to a ligand subject to receptor-mediated endocytosis (see Wu and Wu (1987) J. Biol. Chem. 262:4429-4432) that can be used to target cell types specifically expressing the receptors.

A combination of TMEFF2 nucleic acid-ligand complex can be formed in which the ligand comprises a fusogenic viral peptide to disrupt endosomes, allowing the nucleic acid to avoid lysosomal degradation. A TMEFF2 nucleic acid can be targeted in vivo for cell specific uptake and expression, by targeting a specific receptor (see for example WO 92/06180; WO 92/22635; WO92/20316; WO93/14188; WO 93/20221). Alternatively, a TMEFF2 nucleic acid can be introduced intracellularly and incorporated within the host cell's DNA for expression, by homologous recombination (Koller and Smithies (1989) Proc. Natl. Acad. Sci. USA 86:8932-8935; Zijlstra et al. (1989) Nature 342:435-438).

For gene therapy, various viral vector that contains a TMEFF2 nucleic acid can also be used for example, adenovirus, herpes virus, vaccinia, or, preferably, an RNA virus such as a retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Adenoviruses offer the advantage of being capable of infecting non-dividing cells (Sadeghi and Hitt (2005) Curr. Gene Ther. 5:411-427). Adeno-associated virus (AAV) can also be proposed for use in gene therapy (Walsh et al., 1993, Proc. Soc. Exp. Biol. Med. 204:289-300; Zolotukhin (2005) Hum. Gene Ther. 16:551-557; Carter (2005) Hum. Gene Ther. 16:541-550). A TMEFF2 nucleic acid to be used in gene therapy is cloned into such vectors, which facilitates delivery of the gene into a patient suffering from an affective disorder or Cushing's Syndromes. Such retroviral vectors are well known in the art, see Boesen et al. (1994) Biotherapy 6:291-302; Clowes et al. (1994) J. Clin. Invest. 93:644-651; Kiem et al. (1994) Blood 83:1467-1473; Salmons and Gunzberg (1993) Human Gene Therapy 4:129 141; and Grossman and Wilson (1993) Curr. Opin. in Genetics and Devel. 3:110-114; Falkner and Holzer (2004) Curr. Gene Ther. 4:469-485; Epstein and Manservigi (2004) Curr. Gene Ther. 4:409-416. A number of additional retroviral vectors can also incorporate multiple genes. All of these vectors can transfer or incorporate a gene for a selectable marker so that transduced cells can be identified and generated. By inserting a TMEFF2 sequence of interest encoding a functional TMEFF2 protein into the viral vector, along with another gene which encodes, for example, the ligand for a receptor on a specific target cell, for example, the vector is now target specific. Retroviral vectors can be made target specific by inserting, for example, a polynucleotide encoding a sugar, a glycolipid, or a protein. Those of skill in the art will know of, or can readily ascertain without undue experimentation, specific polynucleotide sequences which can be inserted into the retroviral genome to allow target specific delivery of the retroviral vector containing the inserted polynucleotide sequence.

Since recombinant retroviruses are preferably defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to w2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for TMEFF2 polynucleotides or polypeptides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 pm can encapsulate a substantial percentage of an aqueous buffer containing large macromolecules. RNA, DNA and intact virions can be encapsulated within the aqueous interior and be delivered to cells in a biologically active form (Fraley et al. (1981) Trends Biochem. Sci. 6:77). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al. (1988) Biotechniques 6:682). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries.

The present invention relates, inter alia, to uses and methods for treating affective disorders. An affective disorder is selected from the group consisting of major depression, generalized anxiety disorder and bipolar disorder.

A major depression is selected from the group consisting of major depression, dysthymia, atypical depression, premenstrual dysphoric disorder and seasonal affective disorder.

A generalized anxiety disorder is selected from the group consisting of panic disorder, phobias, agoraphobia, social phobia, specific phobia, obsessive-compulsive disorder, posttraumatic stress disorder, separation anxiety disorder, mania, hypomania and cyclothymic disorder.

A bipolar disorder is bipolar disorder type I or bipolar disorder type II.

In another preferred aspect of the present invention, the TMEFF2 agonist, preferably a TMEFF2 agonist of the CRH signalling pathway, preferably of the cAMP or the TMEFF2 modulator of the Activin signalling pathway applied in the uses and methods of treatment as described herein is administered in combination with another compound which is suitable for treating an affective disorder or Cushing's Syndromes.

Preferably, a compound which is administered in combination with the TMEFF2 agonist, preferably a TMEFF2 agonist of the CRH signalling pathway, preferably of the cAMP or the TMEFF2 modulator of the Activin signalling pathway for treating an affective disorder is selected from the group consisting of amitriptyline, amitriptyline oxide, desipramine, dibenzepin, dosulepin, doxepin, chloroimipramine, imipramine, nortriptyline, mianserin, maprotiline, trimipramine, CP-122721, elzasonan, PD-171729, MK-869, DOV-216303, DOV-21947, licarbazepine, amfebutamone, radafaxine, vilazodone, GSK-679769, GW-597599, NS-2359, GSK-876008, pramipexole, duloxetine, atomoxetine, LY-628535, desvenlafaxine, escitalopram, LU-AA21004, saredutant, SR-58611, SSR-149415, SSR-146977, moclobemide, R-673, R-1204, BMS-469458, DPC-368, Org-34517, Org-34850, inhibitors of the CRH receptors, ONO-2333Ms, NBI-876008, AAG-561, NBI-34041, DPC-368, PD-171729, SSR-125543, viloxazine, trazodone, nefazodone, mirtazapine, venlafaxine, reboxetine, tranylcypromine, brofaromine, moclobemide, citalopram, paroxetine, fluoxetine, fluvoxamine, sertraline, *Hypericum* (St. John's Wort), alprazolam, clonazepam, diazepam, lorazepam, halazepam, chlordiazepoxide, and other drugs such as buspirone, clonidine, pagoclone, risperidone, olanzapine, quetiapine, ziprasidone, celecoxib, piroxicam, parecoxib, valdecoxib, PMI-001, PH-686464, SC-58236, etoricoxib, rofecoxib, L-776967, lumiracoxib, GW-406381, GW-644784, meloxicam, SVT-2016, PAC-10649, CS-706, LAS-34475, cimicoxib, A-183827.0, or nimesulide. Of course, it is envisaged that one or more of the aforementioned compounds can be used in combination with a TMEFF2 agonist for treating an affective disorder. Moreover, it is envisaged that the TMEFF2 agonist and a further compound suitable for treating an affective disorder are administered simultaneously, sequentially or separately from each other.

Preferably, a compound which is administered in combination with the TMEFF2 agonist, preferably a TMEFF2 agonist of the CRH signalling pathway, preferably the cAMP signalling pathway for treating Cushing's Syndromes is selected from the group consisting of ketoconazole, sodium-valproate, bromocriptine, octreotide, o,p'DDD, amino-gluthethimide, metyrapone, retinoic acid, or cyproheptadine. Of course, it is envisaged that one or more of the aforementioned compounds can be used in combination with a TMEFF2 agonist, preferably a TMEFF2 agonist of the CRH signalling pathway, preferably the cAMP signalling pathway for treating Cushing's Syndromes. Moreover, it is envisaged that the TMEFF2 agonist, preferably a TMEFF2 agonist of the CRH signalling pathway, preferably the cAMP signalling pathway and a further compound suitable for treating Cushing's Syndromes are administered simultaneously, sequentially or separately from each other.

In another preferred embodiment the TMEFF2 agonist preferably a TMEFF2 agonist of the CRH signalling pathway, preferably the cAMP signalling pathway or the TMEFF2 modulator of the Activin signalling pathway applied in the uses and methods for the treatment of affective disorders and/or Cushing's Syndromes can be administered in combination with an antagonists against the CRH receptor 1. Such CRH receptor 1 antagonists have been shown to have antidepressant properties and are well known in the art, see for example U.S. Pat. Nos. 4,605,642; 5,063,245; 5,109,111; 5,132,111; 5,245,009; 5,439,885; 5,493,006; 5,510,458; 5,646,152; 5,663,292; 5,705,646; 5,712,303; 5,777,073; 5,874,227; 5,958,948; 5,962,479; 5,968,944; 6,001,807; 6,005,109; 6,060,478; 6,083,948; 6,103,737; 6,103,900; 6,107,294; 6,107,300; 6,124,289; 6,124,463; 6,136,809; 6,143,743; 6,159,980; 6,174,912; 6,191,131; 6,200,979; 6,218,391; 6,218,397; 6,245,769; 6,271,380; 6,294,671; 6,313,124; 6,323,312; 6,350,750; 6,358,950; 6,362,180; 6,365,589; 6,384,039; 6,387,894; 6,399,609; 6,432,989; 6,441,018; 6,448,261; 6,448,265; 6,482,608; 6,495,343; 6,509,338; 6,518,271; 6,525,056; 6,525,067; 6,586,456; 6,589,947; 6,589,958; 6,630,476; 6,638,905; 6,642,230; 6,723,841; 6,734,185; 6,765,008; 6,777,404; 6,821,984; 6,833,378; 6,844,351; 6,869,955; 6,956,047; US 2001/025042; US 2002/013461; US 2002/016328; US 2002/016333; US 2002/022619; US 2002/022632; US 2002/049227; US 2002/147338; US 2002/156089; US 2003/008885; US 2003/064993; US 2003/114451; US 2003/114468; US 2003/125330; US 2003/139426; US 2003/199527; US 2003/220333; US 2004/006066; US 2004/014760; US 2004/023965; US 2004/082597; US 2004/110815; US 2004/176376; US 2004/224964; US 2005/014781; US 2005/038052; US 2005/038055; US 2005/113382; US 2005/171095; WO 85/03705; WO 90/03392; WO 92/22576; WO 94/13643; WO 94/13644; WO 94/13661; WO 9413676; WO 9413677; WO 9533727; WO 9533750; WO 9534563; WO 9602569; WO 9619499; WO 9619499; WO 9728189; WO 9735539; WO 9735539; WO 9744038; WO 9803510; WO 9811075; WO 9854221; WO 9901439; WO 9901454; WO 9910350; WO 9911643; WO 9912908; WO 9938868; WO 9951608; WO 9967247; WO 00/01675; WO 00/01697; WO 00/11003; WO 00/39127; WO 00/59907; WO 00/59908; WO 01/29086; WO 01/53263; WO 01/58489; WO 02/04453; WO 02/072101; WO 02/072202; WO 03/008412; WO 04/050634; WO 04/094408; WO 05/026126; WO 05/039545; WO 05/067973.

In another aspect, the present invention relates an in vitro method for diagnosing an affective disorder comprising determining whether the expression of TMEFF2 in a sample obtained from a subject is decreased or increased compared to the expression of TMEFF2 in a healthy subject.

It is assumed that subjects with bipolar disorders undergo episodes of mania and depression. Consequently, it is most likely that TMEFF2 expression is increased during manic episodes while being decreased during depressive episodes. Accordingly, in order to evaluate whether a TMEFF2 agonist preferably a TMEFF2 agonist of the CRH signalling pathway, preferably the cAMP signalling pathway or a TMEFF2 modulator of the Activin pathway should be administered to a subject suffering from an affective disorder, e.g., a bipolar disorder, it is envisaged to diagnose whether expression of TMEFF2 in a sample obtained from a subject is decreased or increased compared to the expression of TMEFF2 in a healthy subject.

As illustrated in example 10, expression of TMEFF2 is downregulated in patients diagnosed with Cushing's Syndromes. Accordingly, in a further aspect of the present invention, the present invention relates to an in vitro method for diagnosing Cushing's syndrome comprising determining whether the expression of TMEFF2 in a sample obtained from a subject is decreased compared to the expression of TMEFF2 in a healthy subject.

In accordance with the present invention by the term "sample" is intended any biological sample obtained from an individual, cell line, tissue culture, or other source containing polynucleotides or polypeptides or portions thereof. As indicated, biological samples include body fluids (such as blood, sera, plasma, urine, synovial fluid and spinal fluid) and tissue sources found to express the polynucleotides of the present invention. Methods for obtaining tissue biopsies and body fluids from mammals are well known in the art. A biological sample which includes genomic DNA, mRNA or proteins is preferred as a source.

In a preferred embodiment of the described method of diagnosis the individual is a mammal and more preferably human. Moreover, the cells are preferably derived from skin, blood, urine or cerebral spinal fluid or the pituitary glands.

In accordance with this embodiment of the present invention, the diagnosis of an affective disorder or Cushing' Syndromes can, e.g., be effected by isolating cells from an individual, and isolating mRNA from such cells. Such cells can be collected from body fluids, skin, hair, biopsies and other sources. Collection and analysis of cells from bodily fluids such as blood, urine and cerebrospinal fluid is well known to the art; see for example, Rodak, "Haematology: Clinical Principles & Applications" second ed., WB Saunders Co, 2002; Brunzel, "Fundamentals of Urine and Body Fluids Analysis", WB Saunders Co, 1994; Herndon and Brumback (Ed.), "Cerebrospinal Fluid", Kluwer Academic Pub., 1989. In addition, methods for mRNA isolation are well described in the art; see, for example, Sambrook et al., "Molecular Cloning: A Laboratory Manual", $3^{rd}$ edition, Cold Spring Harbor Laboratory, 2001.

Preferably, TMEFF2 expression is determined on nucleic acid level or on protein level. The term "nucleic acid level" includes DNA, cDNA and/or mRNA. The term "protein level" includes protein and amino acids. By way of example, TMEFF2 ribonucleic acid can be measured by hybridisation assays (for example, Northern blot, dot blot) or by polymerase chain reaction (PCR). TMEFF2 amino acids can be measured by immunoassays (ELISA, Western blot, Radioimmunoassay). Antibodies for the TMEFF2 amino acid sequences are known in the art, see for example US 2004/0096392. Example of such antibodies are also commercially available (R&D System, Minneapolis; catalogue number AF1867).

Additionally, the present invention relates to a method for the production of a pharmaceutical composition comprising the steps of a method of the invention for identifying TMEFF2 modulators and further comprising a step, wherein a derivative of said identified TMEFF2 modulator is generated.

The invention furthermore relates to a method for the production of a pharmaceutical composition comprising the steps of a method of the invention for identifying TMEFF2 modulators and formulating the modulator identified, in pharmaceutically acceptable form.

The figures show:

FIG. 1: Diagram illustrating the soluble form of the TMEFF2 protein.

FIG. 2: Diagram illustrating the membrane form of the TMEFF2 protein and its corresponding signalling pathway.

Figure 3:
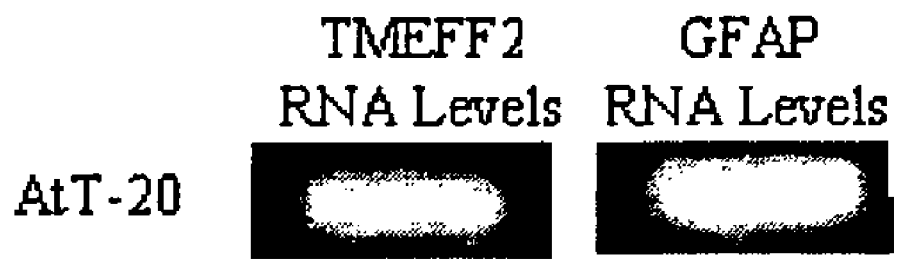

FIG. 3: Corticotroph cells express TMEFF2. The expression of TMEFF2 at the RNA level in the AtT-20 pituitary corticotroph tumour cells was detected by RT-PCR. GAPDH was used as positive control and H2O as negative control.

Figure 4:
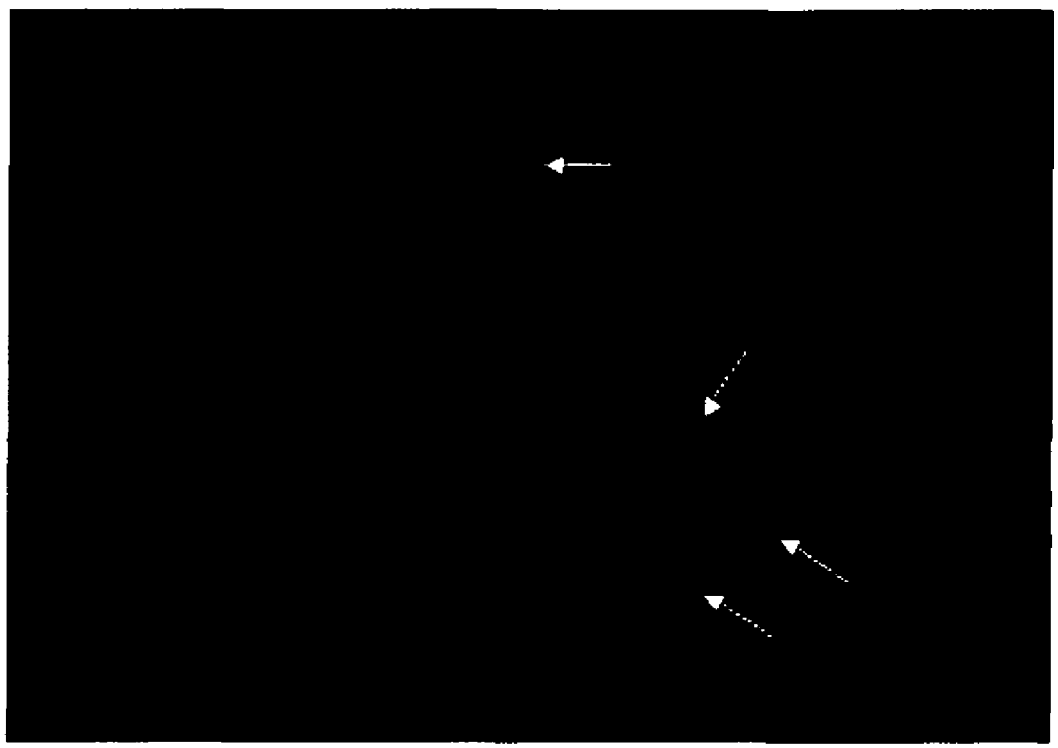

FIG. 4: Cellular localisation of TMEFF2. Arrows indicate the presence of TMEFF2 protein on the cytoplasmic membrane of cells of the chloroid plexus. Magnification: 400×

Figure 5:
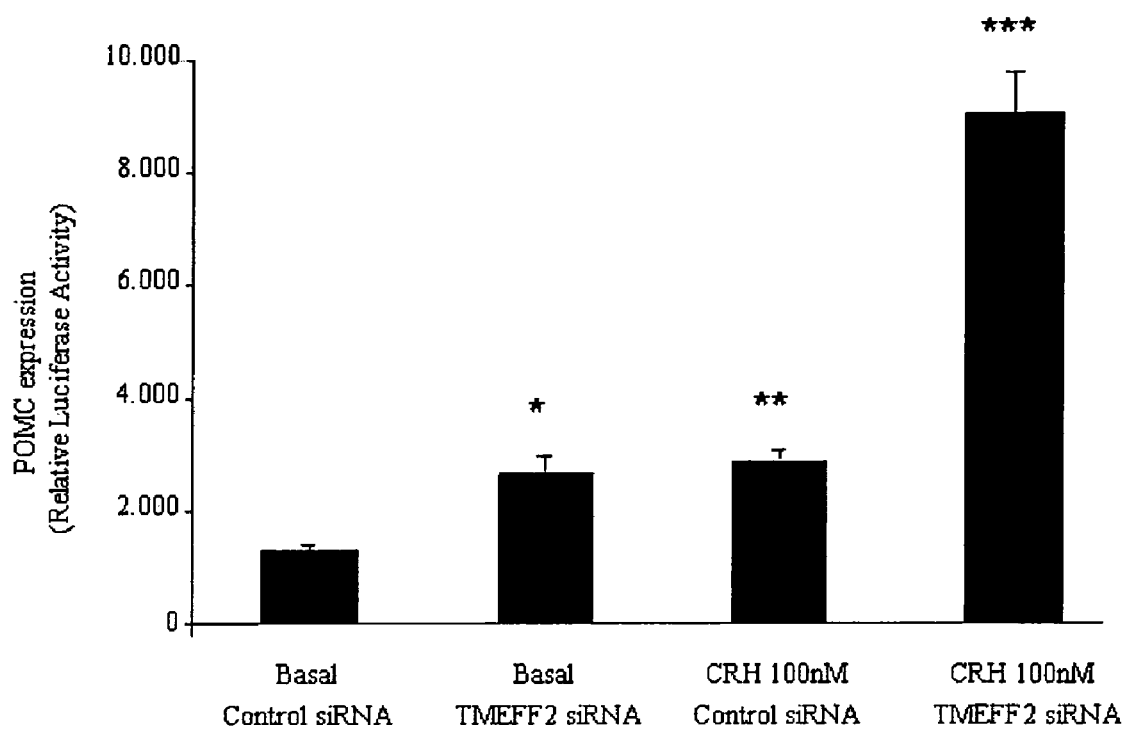

FIG. 5: TMEFF2 inhibition up-regulates POMC transcriptional activity. AtT-20 cells were cotransfected with either TMEFF2 siRNA or control siRNA and POMC-luc. After 48 hours cells were treated with 100 nM CRH for 6 hours. Luciferase activity was measured as described in Materials and Methods. The bars represent the mean and the corresponding SEs of triplicates for each treatment of one representative experiment out of three. *P<0.005 and P<0.001 compared to the corresponding basal value (control siRNA), *P<0.001 compared to CRH stimulation of control siRNA transfected cells.

Figure 6:
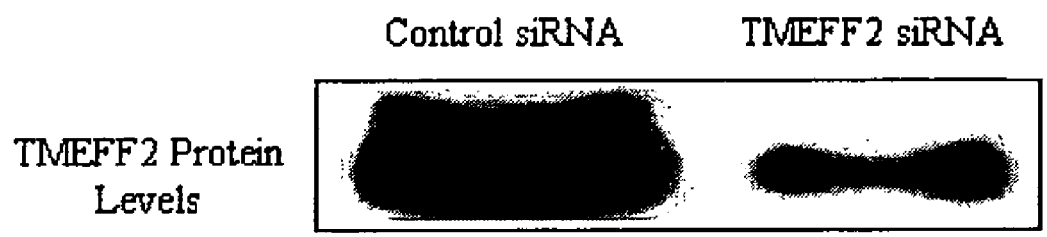

FIG. 6: TMEFF2 protein levels in normal AtT-20 cells and AtT-20 cells treated with siRNA targeting TMEFF2. Western blot analysis was done in AtT-20 cells transiently transfected with control siRNA or TMEFF2 siRNA.

Figure 7:
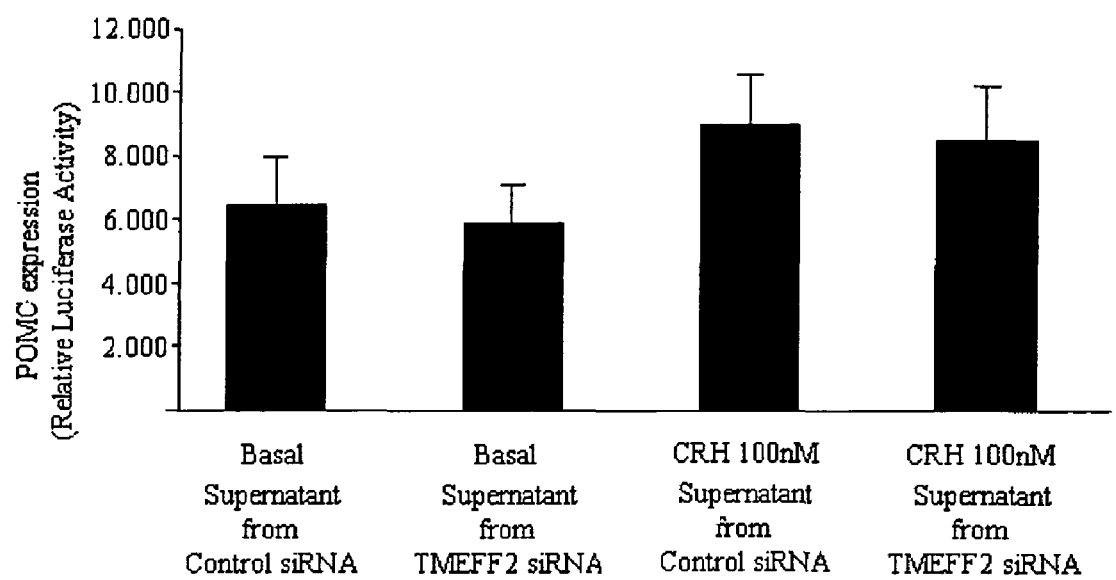

FIG. 7: Soluble TMEFF2 does not regulate POMC tranScriptional activity.

Supernatant from AtT-20 cells treated with control siRNA or TMEFF2 siRNA was applied to wild type AtT-20 cells in the presence or absence of CRH. No significant difference in POMC transcription on wild type AtT-20 cells treated with the supernatant from control siRNA cells or TMEFF2 siRNA cells, whether such cells were in the presence or absence of CRH.

Figure 8:
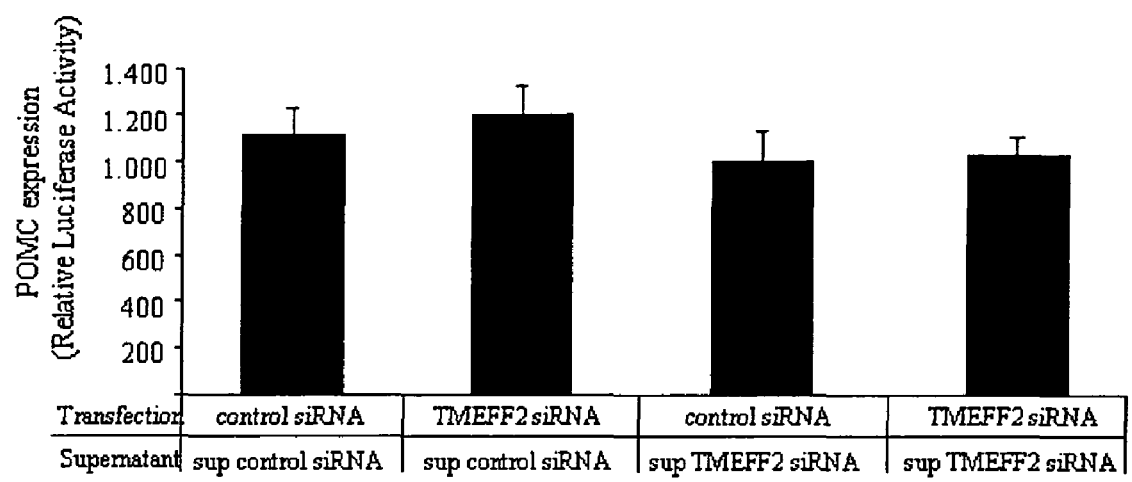

FIG. 8: Soluble TMEFF2 does not regulate POMC transcriptional activity the supernatant of AtT-20 cells treated with control siRNA or TMEFF2 siRNA was applied on AtT-20 cells transfected with control siRNA or TMEFF2 siRNA. No significant difference in POMC transcription on either AtT-20 cells transfected with control siRNA or TMEFF2 siRNA and treated with either the supernatant from control siRNA cells or the supernatant of TMEFF2 siRNA cells.

Figure 9:
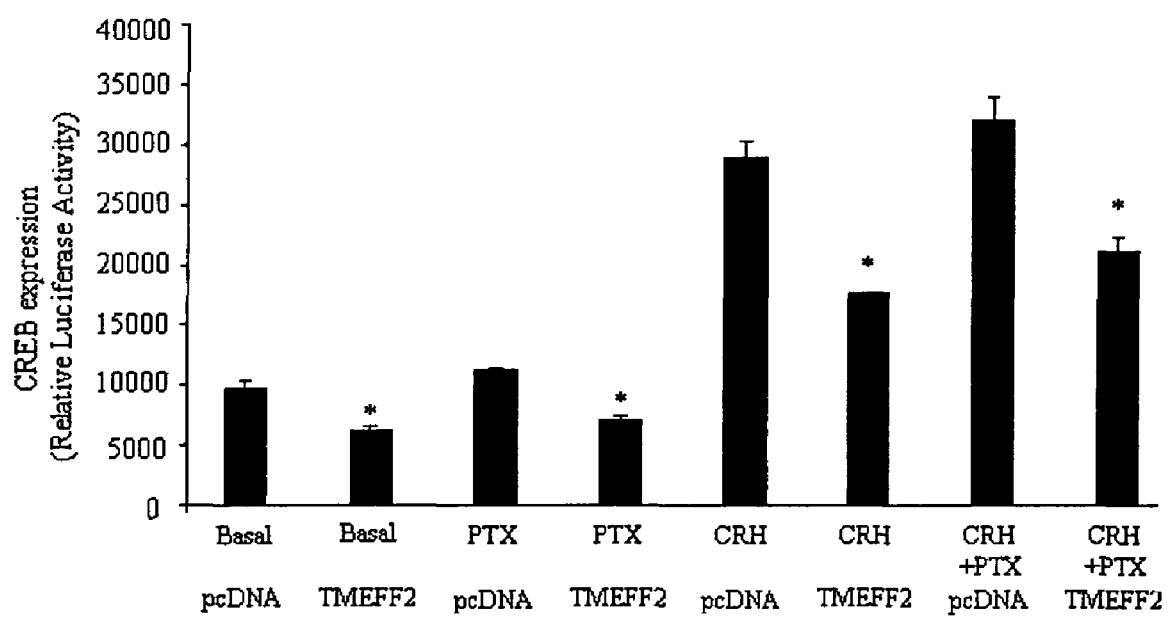

FIG. 9: TMEFF2 inhibition of CRH signalling is not inhibited by Pertussis toxin (PTX).

Figure 10:
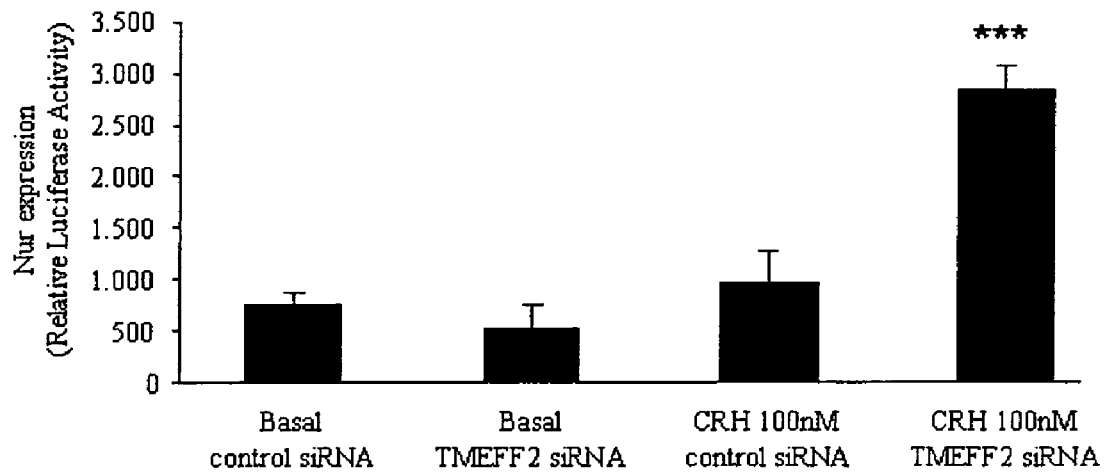

FIG. 10: TMEFF2 inhibition up-regulates Nur transcriptional activity. AtT-20 cells were cotransfected with either TMEFF2 siRNA or control siRNA and NuRE-luc. After 48 hours cells were treated with 100 nM CRH for 6 hours. Luciferase activity was measured as described in Materials and Methods. The bars represent the mean and the corresponding SEs of triplicates for each treatment of one representative experiment out of three. ***P<0.001 compared to CRH stimulation of control siRNA transfected cells.

Figure 11:
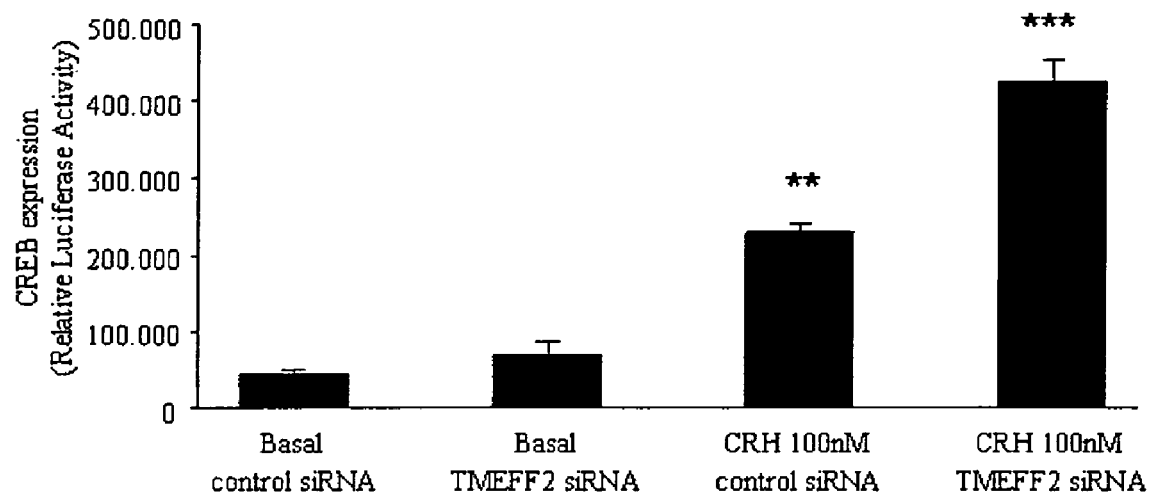

FIG. 11: TMEFF2 inhibition up-regulates CREB transcriptional activity. AtT-20 cells were cotransfected with either TMEFF2 siRNA or control siRNA and CRE-luc. After 48 hours cells were treated with 100 nM CRH for 6 hours. Luciferase activity was measured as described in Materials and Methods. The bars represent the mean and the corresponding SEs of triplicates for each treatment of one representative experiment out of three. P<0.001 compared to the corresponding basal value (control siRNA), *P<0.001 compared to CRH stimulation of control siRNA transfected cells.

Figure 12:
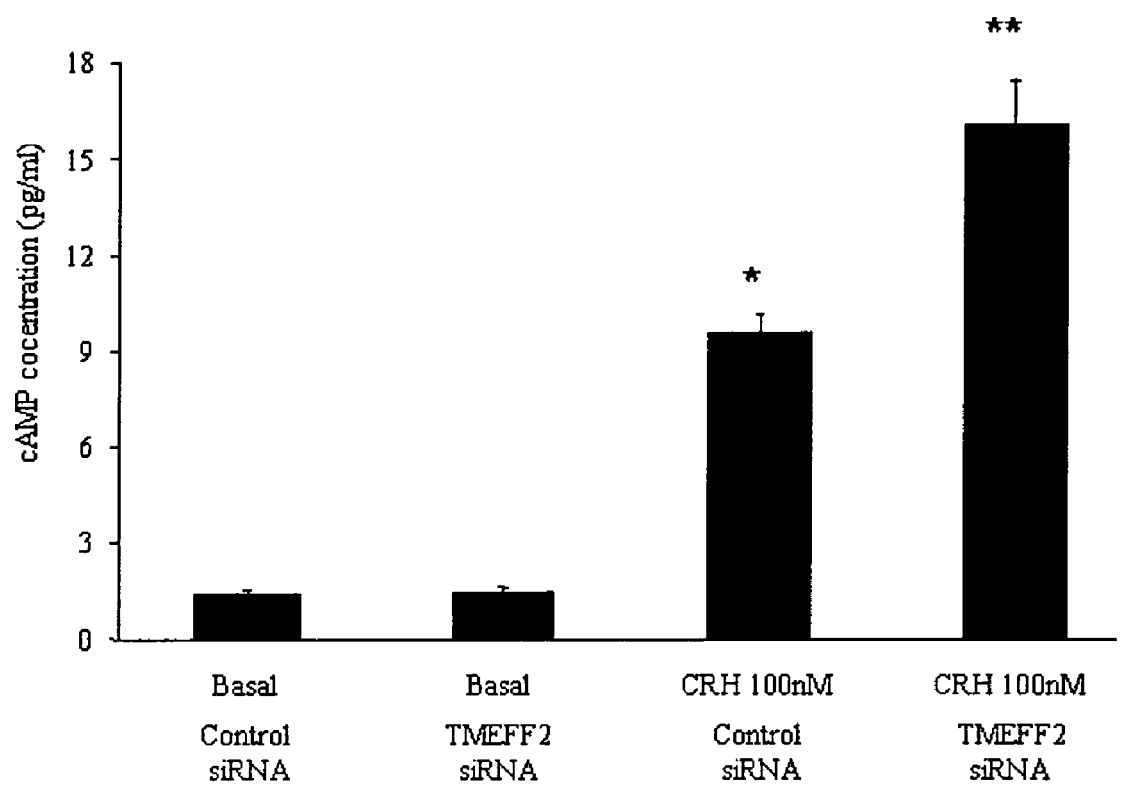

FIG. 12: TMEFF2 inhibition increases the CRH-induced stimulation of cAMP. AtT-20 cells were transfected with either TMEFF2 siRNA or control siRNA. After 48 hours cells were treated with 100 nM CRH for 1 hour. Intracellular cAMP levels were measured as described in Materials and Methods. The bars represent the mean and the corresponding SEs (n=6) of one representative experiment out of three. *P<0.001 compared to the corresponding basal value (cRNA), **P<0.001 compared to CRH stimulation of control siRNA transfected cells.

Figure 13:
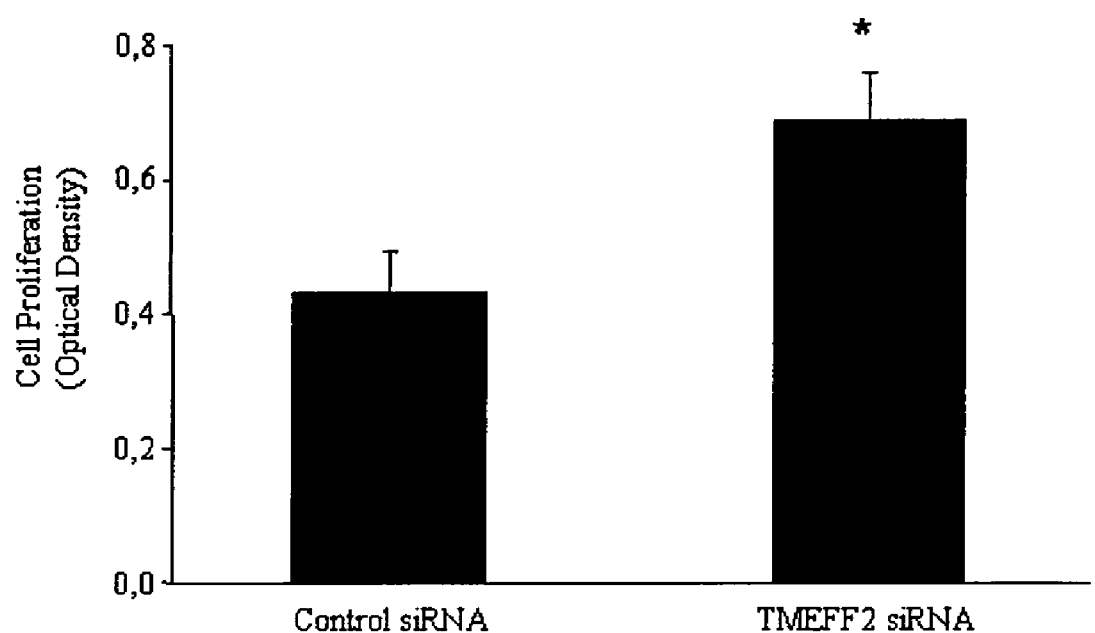

FIG. 13: TMEFF2 inhibition increases cell proliferation in the AtT-20 cell line. AtT-20 cells were transiently transfected with either TMEFF2 siRNA or control siRNA. After 24 hours cells were cultured in medium containing 10% FCS. The bars represent the mean and the corresponding SEs (n=3) of one representative experiment out of three. *P<0.05 compared to the corresponding basal value (control siRNA).

Figure 14:
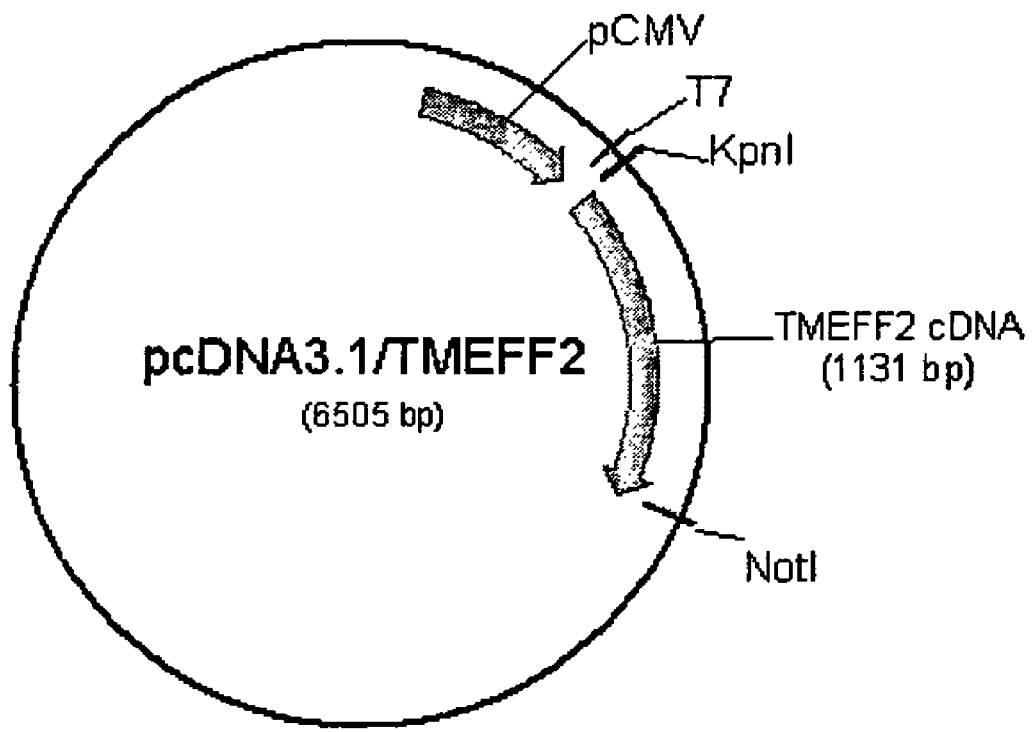

FIG. 14: TMEFF2 expression vector. The mouse TMEFF2 cDNA was inserted into the KpnI-NotI restriction site of the expression vector pcDNA3.1.

Figure 15:
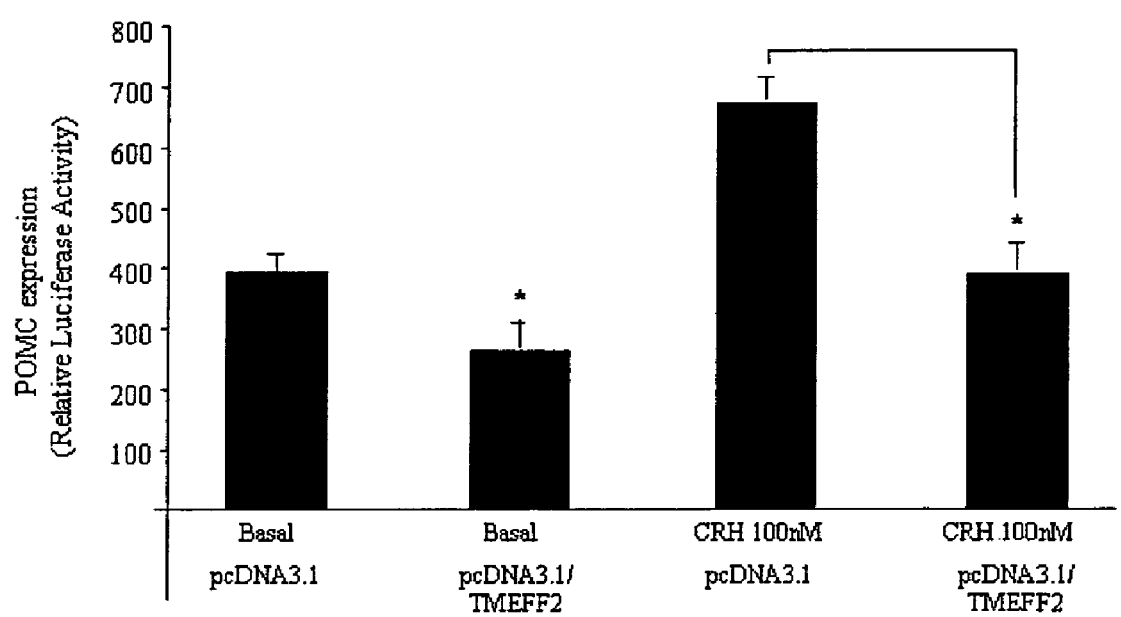

FIG. 15: Overexpression of TMEFF2 inhibits CRH signalling. AtT-20 were transfected with either a control pcDNA3.1 vector or a pcDNA3.1 vector containing the mouse TMEFF2 cDNA.

FIG. 16: Nucleotide and amino acid sequence of human TMEFF2.

FIG. 17: Activin is a secreted protein that binds a serine/threonine receptor complex comprised of a type II ligand binding receptor and a type I signal transducing receptor.

Figure 18:
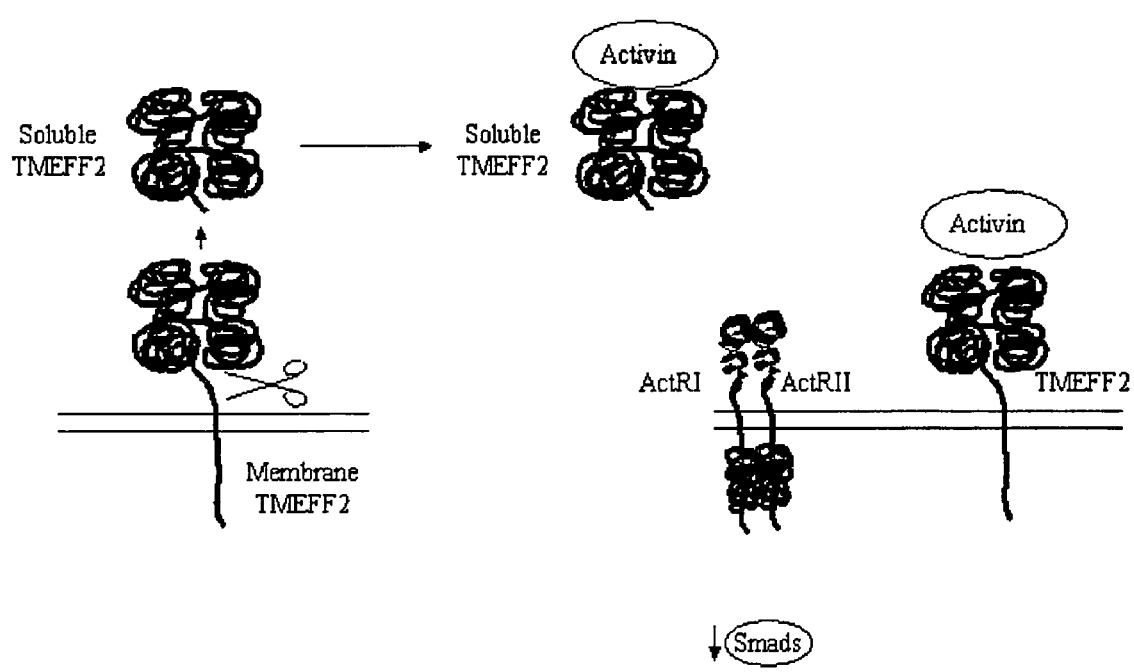
Figure 19:
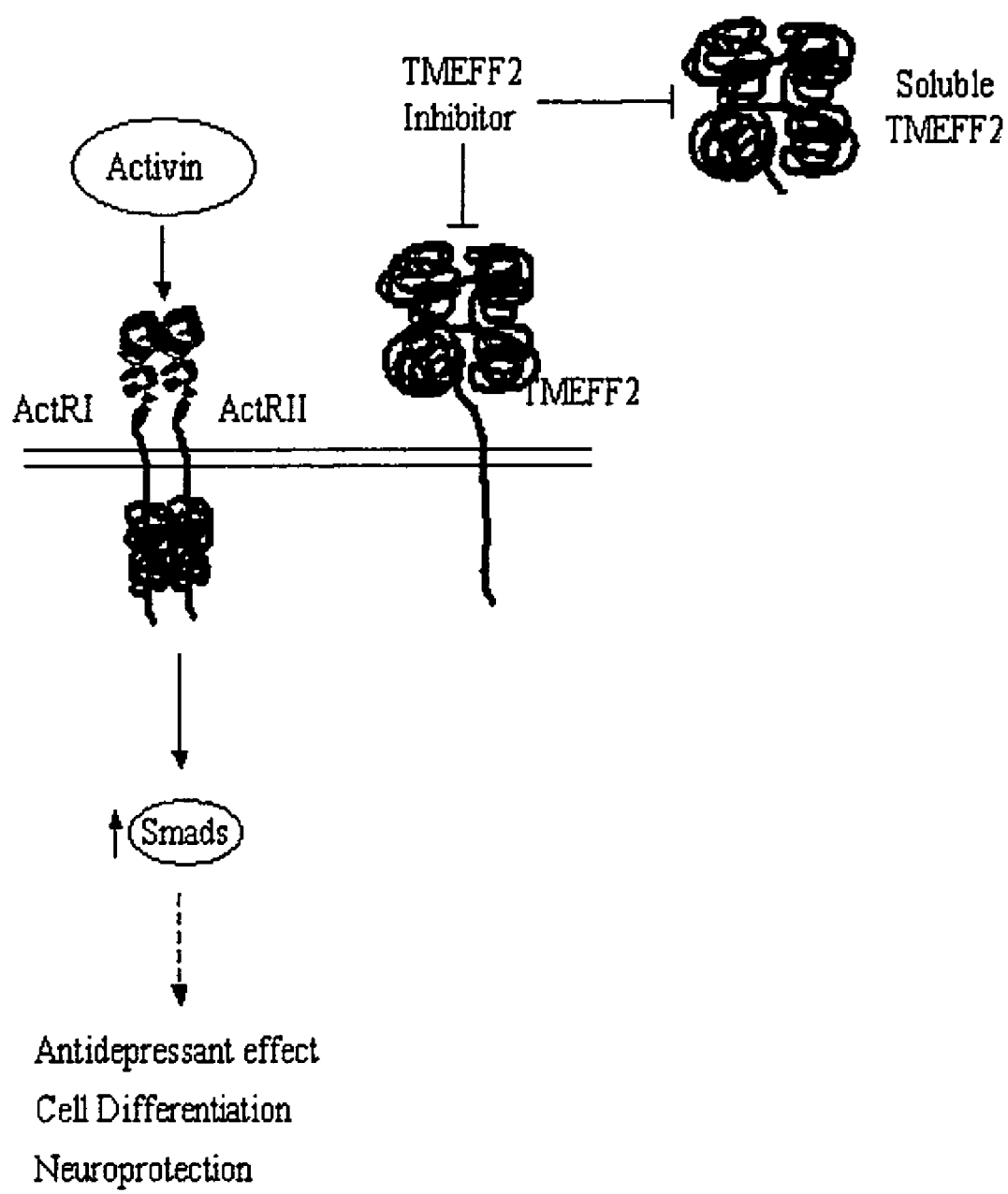

FIG. 18: TMEFF2 is capable of binding Activin through its follistatin-like domains and can prevent binding of Activin to type II Activin receptors, thereby inhibiting Activin signalling.

FIG. 19: Inhibition of TMEFF2 allows Activin to bind to its receptor leading to Smad activation and promotion of antidepressant effects, cell differentiation and neuronal survival.

FIG. 20: Inhibition of TMEFF2 by siRNA for periods of 24 and 48 hours increases active escape attempts and decreases passive behaviour in comparison to control mice.

FIG. 21: TMEFF2 inhibits the Activin signalling pathway and activation of Smad proteins.

FIG. 22: Nucleotide and amino acid sequence of human Activin.

The following examples illustrate the invention. These examples should not be construed as to limit the scope of this invention. The examples are included for purposes of illustration and the present invention is limited only by the claims.

EXAMPLE 1

TMEFF2 Signalling Pathways

The TMEFF2 protein possesses an extracellular region containing follistatin-like and EGF-like domains, a transmembrane region and a cytoplasmic tail (FIG. 1). The extracellular domain has been shown to be cleaved by proteases near the transmembrane region. This proteolytic cleavage releases the extracellular portion of TMEFF2, which then can act as a cytokine or growth factor capable of binding to the erbB family of EGF receptors (Horie et al. (2002) Genomics 67:146-152). This family of receptors does not act through the cAMP pathway but can regulate cell proliferation through kinases such as MAPK and PKC (Moghal and Sternberg (1999) Curr Opin Cell Biol 11:190-196). The binding of the soluble TMEFF2 extracellular domain to the EGF receptor family can be inhibited by TMEFF2 antibodies that prevent the activation of the EGF receptor family.

Besides the extracellular and transmembrane domains, the TMEFF2 protein has an intracellular domain. This intracellular domain contains a putative G-protein binding motif (FIG. 2). G proteins transduce the signals of GPCRs (G protein-coupled receptors) of the family of seven transmembrane proteins. For example, after binding of CRH to the CRH receptor type 1 (CRHR1), the activation of the protein Gs increases the activity of the enzyme adenylate cyclase that produces cAMP (Ulisee et al. (1989) J Biol Chem 264:2156-2163). This results in the activation of the transcription factors CREB and Nur (Paez-Pereda et al. (2001) J Clin Invest 108:1123-1131). These transcription factors promote the transcription of the POMC gene that results in an increase of ACTH production. TMEFF2 activation as a membrane receptor inhibits the G protein and therefore it inhibits cAMP, CREB, Nur, POMC and ACTH.

EXAMPLE 2

Corticotroph Cells Express TMEFF2

The expression of TMEFF2 was assessed in the pituitary corticotroph cell line AtT-20, which secrete ACTH (Leung et al. (1982) Virchows Arch. 396: 303-312; ATCC Number CCL-89). For all experiments, AtT-20 cells were cultured in 45 cm$^3$ culture flasks in Dulbecco's modified Eagle's medium (DMEM) supplemented with 10% foetal calf serum (FCS), 2 mM glutamine, 105 U/litre penicillin/streptomycin and 2.5 mg/litre amphotericin B. Cells were kept at 37° C. in 5% CO2. AtT-20 cells were then distributed in 6-well plates at 3.5×105 cells/ml. Unless stated otherwise, materials were obtained from Invitrogen (Carlsbad, Calif.). RT-PCR were performed as previously described (Paez-Pereda et al. (2003) Proc. Natl. Acad. Sci. 100:1034-1039). Briefly, PCR amplification was performed with the following primers: TMEFF2 sense primer 5'-CTG ATG GGA AAT CTT ATG ATA ATG-3' (SEQ ID NO: 3) and antisense primer 5'-CAG GAA CAA CGT AGA GAA CAC TGT-3' (SEQ ID NO: 4). Internal control was performed by amplifying 13-actin from the same human samples (human β-actin sense primer: 5'-ACG GGG TCA CCC ACA CTG TGC-3' (SEQ ID NO: 5) and antisense primer: 5'-CTA GAA GCA TTT GCG GTG GAC GAT G-3') (SEQ ID NO: 6) and GAPDH from the AtT-20 samples (mouse GAPDH sense primer: 5'-ATG GTG AAG GTC GGT GTG AAC G-3' (SEQ ID NO: 7) and antisense primer: 5'-GTT GTC ATG GAT GAC CTT GGC-3') (SEQ ID NO: 8). The expression of TMEFF2 was detected in AtT-20 cells (FIG. 3) confirming that TMEFF2 is expressed in pituitary cells.

EXAMPLE 3

Membrane Localisation of TMEFF2

The cellular location of the TMEFF2 protein was studied by immunohistochemistry of serial sections of complete mouse brains using a polyclonal antibody against TMEFF2 (R&D Systems). Briefly, brains from wild type mice were shock frozen, cut into 16 μm slices and fixed with paraformaldehide for 5 minutes. The sections were then blocked for 30 minutes at room temperature with 1:10 horse serum. All antibodies were diluted in TBST buffer (Tris-buffered saline with 0.05% Tween-20). The TMEFF2 antibody was used in a dilution 1:200 and incubated overnight. All washes were performed with TBST buffer. An anti-goat IgG antibody conjugated with the red dye Alexa-Fluor was used as secondary antibody (Molecular Probes). Cells were counterstained with bisbemzimide allowing visualisation of the cell nucleus. Strong fluorescence labelling was observed at the cytoplasmic membrane of cells (FIG. 4). Therefore, TMEFF2 is present at the cytoplasmic membrane of cells which support its function as a membrane bound receptor.

EXAMPLE 4

TMEFF2 Inhibition Enhances CRH Effects on POMC Transcriptional Activity

In order to elucidate the role of TMEFF2 on CRH-stimulated POMC transcription, AtT-20 cells were cotransfected with either TMEFF2 siRNA or control siRNA and a POMC-luciferase reporter plasmid, expressing all the sequences necessary for the in vivo POMC expression in mouse pituitary. Briefly, The sequences of the two mouse TMEFF2 siRNA oligo used were 5'-UCA GAA GGA UCC UGU GCU A-3' (SEQ ID NO: 9) and 5'-CGG UUA CGA UGA CAG AGA A-3' (SEQ ID NO: 10). Non-specific control RNA (control siRNA) oligos with similar GC content compared to siRNA were used as control (MWG-Biotech, Ebersberg, Germany). All AtT-20 cell transfection were performed using Lipofectamine 2000. Twenty-four hours after plating, cells were transfected in OPTIMEM medium using 10 µl Lipofectamine and 50 nM TMEFF2 siRNA or control siRNA per well. After 6 h the transfection medium was removed and the cells were cultured in DMEM supplemented with 2% FCS. The POMC-Luc plasmid containing the luciferase gene under the control of 770 by of the rat POMC promoter includes all the necessary sequences for the expression and regulation of POMC (Therrien and Drouin. (1991) Mol. Cell. Biol. 11: 3492-3503; Liu et al. (1992) Mol. Cell. Biol. 12: 3978-3990). The pEGFP-C2 Vector (Clontech, Palo Alto, Calif.) encoding an optimized variant of the green fluorescent protein (GFP) was used as the control for the transfection efficiency in all experiments. Cells were transfected using the TMEFF2 siRNA or control siRNA together with 1 µg reporter plasmid and 500 ng control pEGFP plasmid per well. After 48 hours in culture medium cells were incubated for 6 h with 100 nM CRH. At the end of the treatment the protein lysate was collected and the luciferase activity was measured in a Wallac luminometer as previously described (Paez-Pereda et al. (2001) J. Clin. Invest. 108: 1123-1131). The fluorescence values of the control pEGFP plasmid were measured in a Wallac fluorometer using a 485-nm excitation wavelength and a 535-nm emission wavelength.

Transfected cells were incubated in the presence or absence of 100 nM CRH, a physiological stimulus for POMC transcription. CRH stimulated POMC-transcriptional activity in control siRNA transfected cells (FIG. 5). We found for the first time that under CRH stimulation the TMEFF2 siRNA induced a three-fold increase in POMC promoter activity with respect to control siRNA transfected cells (FIG. 5). Moreover, the TMEFF2 siRNA produced a significant increase in POMC-dependent transcription with respect to control siRNA transfected cells. Results are expressed as mean±SE. Differences were assessed by one-way ANOVA in combination with Scheffé's test, taking P values less than 0.05 as significant. Inhibition of TMEFF2 expression was assessed by determining the levels of TMEFF2 protein. Briefly, AtT-20 cells were transfected either with TMEFF2 siRNA or with control siRNA as indicated above. After two days, cell lysates were collected and analyzed by Western blot as previously described (Paez-Pereda et al. (2003) Proc. Natl. Acad. Sci. 100:1034-1039) with an anti-TMEFF2 antibody (R&D systems, Wiesbaden, Germany). TMEFF2 protein can be detected in AtT-20 cells transfected with control siRNA while significant inhibition of TMEFF2 protein can be observed in AtT-20 transfected with siRNA targeting TMEFF2 (FIG. 6).

Taken together, these results indicate that TMEFF2 inhibition enhances POMC transcriptional activity under CRH stimulation and basal conditions. Since the POMC gene encodes ACTH, activation of TMEFF2 will consequently inhibit CRH activation of the POMC expression and reduce production of ACTH.

EXAMPLE 5

TMEFF2 Acts as an Integral Membrane Receptor

The extracellular domain of TMEFF2 has been proposed to be released into the extracellular matrix via proteolytic cleavage (Horie et al. (2002) Genomics 67:146-152). Consequently, the extracellular form of TMEFF2 can be found in the supernatant of AtT-20 cells.

To assess whether the therapeutic activity of TMEFF2 on affective disorders and Cushing's syndromes is due to its membrane bound form and not to its extracellular form, the supernatants of AtT-20 cells treated with control or TMEFF2 siRNA was applied to wild type AtT-20 cells and transcription of the POMC gene was assessed. As illustrated in FIG. 7, there was no significant difference in POMC transcription on wild type AtT-20 cells treated with the supernatant from control siRNA cells or TMEFF2 siRNA cells, whether such cells were in the presence or absence of CRH. Therefore, TMEFF2 extracellular domain is not responsible for the regulation of POMC transcription.

Similar results were observed when the supernatant of AtT-20 cells treated with control siRNA or TMEFF2 siRNA was applied on AtT-20 cells transfected with control siRNA or TMEFF2 siRNA (FIG. 8). Therefore, supernatants containing or not TMEFF2 soluble domain produced no effects on cells that express or not membrane bound TMEFF2.

Further evidence that the therapeutic activity of TMEFF2 on affective disorders and Cushing's syndromes is due to its membrane bound form and not to its extracellular form is provided by assessing the effect of TMEFF2 on G protein and CRH signalling. TMEFF2 has been suggested to act through activation of G proteins (Uchida et al. (1999) Biochem Biophys Res Comm 266:595-60002). G proteins include Gs proteins which are involved in the activation of membrane-bound adenylyl cyclase and increase cAMP production while activation of inhibitory G proteins (Gi proteins) decrease cAMP production. The Pertussis toxin from *Bordetella pertussis* is known to block the effects of Gi protein (Codina et al. (1983) Proc Natl Acad Sci USA 80:4276-4280). However, the effects of CRH, which are known to be mediated by the activation of protein Gs, are not affected by Pertussis toxin (Ulisee et al. (1989) J Biol Chem 264:2156-2163). Consequently, if the effect of TMEFF2 on the cAMP pathway would be through the activation of protein Gi, these effects would be inhibited by treatment with the Pertussis toxin.

AtT-20 cells were co-transfected with the reporter plasmid CRE-Luc and the expression vector of TMEFF2 (pcDNA3.1/TMEFF2) or empty pcDNA3.1 as control. After transfection the cells were treated with 0.1 ug/ml Pertussis toxin (PTX) for 16 hours and then with 100 nM CRH for 6 hours. Luciferase activity was measured at the end of the experiment. As illustrated in FIG. 9, overexpression of TMEFF2 inhibits the effects of CRH even in the presence of Pertussis toxin. This result demonstrate that TMEFF2 inhibits CRH signalling through Gs protein and not through Gi protein.

EXAMPLE 6

TMEFF2 Inhibition Enhances CRH Effects on Nur Transcriptional Activity

One of the transcription factors that controls POMC expression and, therefore, ACTH biosynthesis in response to CRH is Nur77 and other members of its family such as Nurr1. In order to elucidate the role of TMEFF2 on CRH-stimulated Nur transcriptional activity, AtT-20 cells were cotransfected with either TMEFF2 siRNA or control siRNA and a Nur reporter construct: NurRE-luciferase. Transfected cells were incubated in the presence or absence of 100 nM CRH. We found for the first time that under CRH stimulation the TMEFF2 siRNA induced an enhancement of the response of Nur to CRH (FIG. 10). These results indicate that TMEFF2 inhibition enhances the response to CRH stimulation at the level of Nur transcriptional activity. By contrast, activation of TMEFF2 will inhibit expression of Nur in the presence of CRH.

EXAMPLE 7

TMEFF2 Inhibition Enhances CRH Effects on CREB Transcriptional Activity

The cAMP pathway activates the transcriptional activity of CREB (cAMP responsive element binding protein). CREB plays an important role in the CRH signal transduction. In order to elucidate the role of TMEFF2 on CRH-stimulated CREB transcriptional activity, AtT-20 cells were cotransfected with either TMEFF2 siRNA or control siRNA and a CREB reporter construct: CRE-luciferase. Transfected cells were incubated in the presence or absence of 100 nM CRH. We found for the first time that under CRH stimulation the TMEFF2 siRNA induced an enhancement of the response of CREB to CRH (FIG. 11). These results indicate that TMEFF2 inhibition enhances the response to CRH stimulation at the level of CREB transcriptional activity. By contrast, activation of TMEFF2 will inhibit expression of CREB in the presence of CRH.

EXAMPLE 8

TMEFF2 Inhibition Increases the CRH-Induced Stimulation of cAMP

Activation of the CRH pathway increases the intracellular levels of cAMP. To determine whether the stimulation of CRH-induced POMC transcription by TMEFF2 siRNA is mediated by cAMP, AtT-20 cells were transfected with either control siRNA or TMEFF2 siRNA. Transfected cells were treated for 1 hour with 100 nM CRH and at the end of the treatment the cell lysates were collected and intracellular cAMP was assessed. Radioimmunological cAMP determination was performed with a commercial RIA kit from NEN™ Life Science Products Inc. (Boston, Mass.). In brief, 24 hours after transfection AtT-20 cells were cultured in 48 well plates. The next day cells were washed, and stimulated with 100 nM CRH (Bachem, Heidelberg, Germany). The phosphodiesterase inhibitor IBMX (5 mM) was added to all stimulation solutions. The supernatants were collected and assayed after 1 h of incubation with CRH as previously described (Stalla et al. (1989) Endocrinology 125: 699-706).

In the presence of CRH, TMEFF2 siRNA produced a significant increase in the levels of cAMP with respect to those of the control siRNA (FIG. 12), whereas the inhibition of TMEFF2 using siRNA had no significant effect on the basal values of cAMP. This result indicates that TMEFF2 regulates the CRH-induced POMC-transcriptional activity through the modulation of cAMP.

EXAMPLE 9

TMEFF2 Inhibition Increases Cell Proliferation in the AtT-20 Cell Line

Studies in prostate cancer cells showed anti-proliferative effects of TMEFF2 (Afar et al., 2004, Mol. Cancer. Ther. 3:921-932). To determine whether this also occurs in corticotroph tumour cells, AtT-20 cells were transiently transfected with TMEFF2 siRNA or control siRNA. 24 hours after transfection cells were incubated in DMEM medium containing 10% FCS. The next day a colorimetric assay WST-1 based assay (Roche Molecular Biochemicals, Basel, Switzerland) was used to measure cell proliferation and cell viability following the manufacturer's instructions (Páez-Pereda et al. (2000) J. Clin. Endocrinol. Metab. 85:263-269). The values of the background absorbance were subtracted from the absorbance of all samples. Acridine orange-ethidium bromide staining was used to rule out cell death due to toxic effects.

24 hours after transfection, cells were stimulated with 10% FCS, and incubated for another 24 hours. Cell proliferation was measured by the WST-1 method (FIG. 13). Inhibition of TMEFF2 was found to produced an increase in the cell proliferation with respect to the cells transfected with control siRNA.

EXAMPLE 10

TMEFF2 Expression is Downregulated in Cushing's Syndromes

Expression of TMEFF2 was then analysed in ACTH producing pituitary adenomas isolated from patients suffering from Cushing's Syndromes (table 1). PCR amplification was performed with the following primers: TMEFF2 sense primer 5'-CTG ATG GGA AAT CTT ATG ATA ATG-3' (SEQ ID NO: 11) and antisense primer 5'-CAG GAA CAA CGT AGA GAA CAC TGT-3' (SEQ ID NO: 12). Internal control was performed by amplifying β-actin from the same human samples (human β-actin sense primer: 5'-ACG GGG TCA CCC ACA CTG TGC-3' (SEQ ID NO: 13) and antisense primer: 5'-CTA GAA GCA TTT GCG GTG GAC GAT G-3') (SEQ ID NO: 14).

TABLE 1

Expression of TMEFF2 in human normal pituitary and ACTH-secreting pituitary ademonas

| Sample | Phenotype | TMEFF2 expression levels[1] |
|---|---|---|
| 1 | Normal Pituitary | +++ |
| 2 | Normal Pituitary | +++ |
| 3 | Cushing Pituitary | ++ |
| 4 | Cushing Pituitary | − |
| 5 | Cushing Pituitary | − |
| 6 | Cushing Pituitary | + |
| 7 | Cushing Pituitary | + |
| 8 | Cushing Pituitary | − |
| 9 | Cushing Pituitary | + |
| 10 | Cushing Pituitary | − |
| 11 | Cushing Pituitary | − |
| 12 | Cushing Pituitary | − |
| 13 | Cushing Pituitary | + |
| 14 | Cushing Pituitary | ++ |
| 15 | Cushing Pituitary | − |

−: No TMEFF2 expression
+: weak TMEFF2 expression
++: Moderate TMEFF2 expression
+++: Strong TMEFF2 expression TMEFF2 expression was reduced in ACTH producing pituitary adenomas from patients with Cushing's Syndromes as compared to the human normal pituitary. In corticotrophinomas there was either no signal or low expression of the gene compared to the expression detected in normal tissue (Table 1).

These data demonstrate that Cushing's Syndromes can be diagnosed according to the expression levels of TMEFF2.

EXAMPLE 11

Activation of TMEFF2 Inhibits CRH Signalling and ACTH Production

In order to demonstrate that activation of TMEFF2 can inhibit CRH signalling, AtT-20 cells were transfected with an expression vector containing the mouse TMEFF2 cDNA and a POMC-luciferase reporter plasmid. Briefly, the mouse TMEFF2 cDNA was inserted into the expression vector pcDNA3.1 (Invitrogen; FIG. 14). AtT-20 cells were then transfected with 1 μg POMC-luc reporter plasmid with either 1 μg control pcDNA3.1 (i.e. not containing TMEFF2) or 1 μg pcDNA3.1 containing TMEFF2. After 48 hours in culture medium cells were incubated for 6 h with 100 nM CRH. At the end of the treatment the protein lysate was collected and the luciferase activity was measured in a Wallac luminometer as previously described (Páez-Pereda et al. (2001) J. Clin. Invest. 108: 1123-1131).

The expression of TMEFF2 produces a reduction of POMC transcription under basal conditions and it inhibits the stimulatory effect of CRH (FIG. 15). Thus, a higher activity of TMEFF2 reduces POMC transcription and inhibits CRH signal transduction. Since active CRH signalling and ACTH production is involved in affective disorders and Cushing's syndromes activation of TMEFF2 can be used to treat affective disorders and Cushing's syndromes by inhibiting CRH signalling and ACTH production.

EXAMPLE 12

TMEFF2-Activin Signalling Pathway

The TMEFF2 protein possesses an extracellular region containing follistatin-like and EGF-like domains, a transmembrane region and a cytoplasmic tail (FIG. 17). The extracellular domain has been shown to be cleaved by proteases near the transmembrane region. This proteolytic cleavage releases the extracellular portion of TMEFF2, which then can act as a cytokine or growth factor capable of binding to the erbB family of EGF receptors (Horie et al. (2002) Genomics 67:146-152). Proteins containing follistatin-like domains are capable of binding to the growth factor Activin with high affinity (Schneyer et al., 2001, Mol Cell Endocrinol 180:33-38; Sidis et al., 2001, J Biol Chem 276:17718-17726).

Activin is a member of the TGF-13 superfamily and participates in several biological processes such as cell differentiation, neurogenesis, hormonal secretion, and neuronal survival (Schubert et al., 1990, Nature 344:868-870; Ameerum et al., 1996, Cell Growth Differ 12:1679-1688; Iwahori et al., 1997, Brain Res 760:52-58; Sulyok et al., 2004, Mol Cell Endocrinol 225:127-132). Activin is a secreted protein that binds a serine/threonine receptor complex comprised of a type II ligand binding receptor and a type I signal transducing receptor (FIG. 17). There are two subtypes of the type II Activin receptor in vertebrates, type IIA (ActRIIA) and IIB (ActRIIB). ActRIIA and ActRIIB are the primary Activin receptor and are constitutively active serine/threonine kinases that recruit type I receptor ALK4 (Activin receptor-like kinase 4) by means of bound Activin (Greenwald et al. (1999) Nat Struct Biol 6:18-22; Bernard et al. (2002) Mol Cell Endo-crinol 196:79-93; Thompson et al. (2003) EMBO J. 22:1555-1566). The functional complex of Activin receptors at the cell surface consists of two type II receptors and two type I receptors. The cellular responses to Activin are mediated by phosphorylation of the transcription factors Smad2, Smad3 and other Smad proteins (Abe et al, 2004, Growth Factors 22:105-110). Smad proteins form homo- and heteromeric complexes that are capable of binding to DNA and regulate the expression of target genes.

Activin expression and Smad2 phosphorylation are increased during treatment with antidepressant drugs (Dow et al., 2005, J Neuroscience 25:4908-4916). Infusion of Activin into the hippocampus of animal models of depression has also been shown to have antidepressant-like effects. Consequently, regulation of Activin and Smad2 signalling can contribute to the action of antidepressant drugs.

TMEFF2 through its follistatin-like domains is capable of binding Activin, prevent the binding of Activin to type II Activin receptors, and by consequence inhibit Activin signalling (FIG. 18) and reduce activity of Smad proteins. Inhibitors of TMEFF2 allows Activin to bind its receptor, activate Smads and promoters antidepressant effects, cell differentiation and neuronal survival (FIG. 19).

EXAMPLE 13

Inhibition of TMEFF2 has Antidepressive Effects

In order to demonstrate that inhibition of TMEFF2 has antidepressive effects, TMEFF2 function was specifically inhibited by delivering double stranded small interference RNA molecules (siRNA) into the brain of mice. Two guide cannula (23 gauge, length 10 mm) were bilaterally inserted into amygdala of the brain of male DBA/2Jico mice. Insertion of the guide cannula was done using a stereotaxic instrument. The coordinates, in relation to bregma, were −1.0 mm posterior, ±3.1 mm lateral, and −1.6 mm ventral. Following a 10 days recovery period, the mice were divided into two experimental groups that were injected with either control double stranded missense RNA (control), or with TMEFF2 specific double stranded siRNA (TMEFF2 siRNA). The sequence used for control missense siRNA was 5'-CGC GUA GAA GAU GAA GUU G TT-3' (SEQ ID NO: 15). The sequence used for TMEFF2 siRNA were 5'-UCA GAA GGA UCC UGU GCU A-3' (SEQ ID NO: 16) and 5'-CGG UUA CGA UGA CAG AGA A-3' (SEQ ID NO: 17). On day 10 after surgery, control or TMEFF2 siRNA were infused in unanaesthetised mice at a concentration of 0.2 nmol/μl, and a volume of 0.5 μl per side, over a period of 2 min per side, using specifically adapted infusion systems (33 gauge, length 12 mm). The animals were left undisturbed until behavioural testing took place.

The effects of TMEFF2 inhibition on depressive-like behaviour was assessed 24 hours (FST1) and 48 hours (FST2) after infusion of control or TMEFF2 siRNA according to the forced swim test paradigm. The forced swim test is a standard test that is based on the assumption that animals will normally try to escape from an aversive stimulus. When the aversive stimulation is inescapable, the animal will eventually stop trying to escape. Early cessation of attempts to escape is considered a rodent analogue of stress-induced depression. The test is used to determine the effectiveness of antidepressants, test new pharmaceutical compounds and validate animal models of depression (Porsolt et al., Arch. Int. Pharmacodym. 229 (1977), 327-336; Porsolt, Rev. Neurosci. 11 (2000), 53-58; Rénéric et al., Behav. Brain Res. 136 (2002), 521-532; Page et al., Psychopharmacology 165 (2003), 194-

201; Kelliher et al., Psychoneuroendocrinology 28 (2003), 332-347). The test consists of placing a mouse for a period of 5 minutes into a glass cylinder containing water. Under such circumstances, the mouse cannot touch the bottom of the cylinder and is thus forced to swim. Time, latency and frequency of struggling versus floating are scored as behavioural parameters. Floating (i.e. movements made only for keeping balance and breath) is a passive behaviour associated with despair and represents a depressive-like symptom since the animal does not make any effort to actively cope with the stressful situation. Increased struggling (i.e. active attempts to escape) indicates active coping behaviour that can be interpreted as an improvement of depression-like symptoms. For example, treatment with serotonergic antidepressants reduce the total time spent floating (Borsini, Neurosci. Biobehav. Rev. 19 (1995), 377-395; Redrobe and Bourin, Psychopharmacology 138 (1998), 198-206, and in parallel increases the time of active behaviour (i.e. swimming or struggling; Lucki et al., Psychopharmacology 155 (2001), 315-322).

Inhibition of TMEFF2 by siRNA for periods of 24 and 48 hours was found to increase active escape attempts (i.e. increase in time of struggling) while a decrease in passive behaviour (i.e. decrease in time and frequency of floating) was measured when compared to control mice injected with control siRNA (FIG. 20). These results demonstrate that TMEFF2 inhibition has antidepressant properties that results in improvements of depression-like behaviour.

EXAMPLE 14

TMEFF2 Inhibits Activin Signalling and Reduce the activity of Smad proteins

Binding of Activin to type II Activin receptors results in the phosphorylation of the Smad proteins such as Smad2 and Smad3 which form homo- and heteromeric complexes with other proteins to bind DNA and regulate gene transcription. Consequently, Activin signalling can be monitored by assessing the binding and activation of Smads target genes. When phosphorylated by Activin receptors, Smad proteins such as Smad3 and Smad4 can bind to the specific DNA sequence CAGA (Dennler et al., 1998, EMBO J. 17:3091-3100; Lin et al., 2005, J Immunol 175:547-554; Luo et al., 2006, Proc Natl Acad Sci USA 103:18326-18331). In order to demonstrate that activation of TMEFF2 can inhibit Activin signalling and Smad activity, AtT-20 cells were transfected with an expression vector containing the human TMEFF2 cDNA and plasmid containing 12 copies of the CAGA sequence in front of a luciferase reporter. The human TMEFF2 cDNA was inserted into the expression vector pcDNA3.1 (Invitrogen).

AtT-20 cells were cotransfected with either 1 μg/ml human TMEFF2 or pcDNA3.1 control plasmid and 1 μg/ml 12×CAGA(SEQ ID NO: 20)-luciferase plasmid. The culture medium was replaced by DMEM+10% FCS 24 hours later and 48 hours after transfection, cells were treated with 50 ng/ml Activin for 6 hours in medium containing 0% FCS. Luciferase activity was then measured in a Wallac luminometer as previously described (Páez-Pereda et al., 2001, J. Clin. Invest. 108: 1123-1131).

TMEFF2 expression reduced the transcriptional activation of the 12×CAGA(SEQ ID NO: 20)-luciferase plasmid by Activin (FIG. 21). This result demonstrates that TMEFF2 inhibits the Activin signalling pathway and activation of Smad proteins. Since active Activin signalling and increase Smad2 activity are known to be involved in antidepressant activity (Dow et al., 2005, J Neuroscience 25:4908-4916), inhibition of TMEFF2 can be used to treat affective disorders by promoting Activin signalling and Smad activity.

EXAMPLE 15

Methods for Identifying TMEFF2 Inhibitors

TMEFF2 follistatin-like domains are capable of binding to Activin through a protein-protein interaction. Screening assays that measures protein-protein interactions can be used to select compounds that disrupt TMEFF2 binding to Activin, such as scatchard analysis, scintillation proximity assays (SPA), Fluorescence resonance energy transfer (FRET), fluorescense polarisation, two hybrid assays, pull down assays, and others (for a review of screening methods, please see Warner et al., 2004, Curr Med Chem 11:721-730;Yin, Hamilton, 2005, Angew Chem Int Ed 44:4130-4163; Cheme, 2006, ChemMedChem 1:400-411).

For example, Activin can be radioactively labelled with $I^{125}$ or $H^3$ and can be contacted with TMEFF2, fragments of TMEFF2 or cells that express TMEFF2. The fraction of free labelled Activin can be separated from the fraction bound to TMEFF2 by precipitation, filtration or column chromatography. The amount of radioactively labelled Activin that binds TMEFF2 can be estimated by measuring the radioactivity bound to TMEFF2 with a beta particle counter. The data can be analyzed using a Scatchard analysis. Alternatively, Activin can be labelled with fluorescent dyes or with fluorescent proteins and the amount of Activin bound to TMEFF2 can be measured by fluorescence detection.

Alternatively, the binding of Activin to TMEFF2 can be measured by "scintillation proximity assay" (SPA). In this case, TMEFF2 or fractions of TMEFF2 can be bound to SPA scintillation beads and Activin can be labelled for example with $I^{125}$ or $H^3$. If the two molecules are bound, the decay particles from the labelled Activin stimulate light emission from the SPA beads. The free Activin fraction does not produce light emission because it is not close enough to the beads. This assay can also be performed by labelling TMEFF2 and binding Activin to SPA beads. Details of such methods are well known in the art, see for example Wu and Lui, 2005, BioDrugs 19:383-392.

Yet another method to detect inhibitors of TMEFF2 is to measure TMEFF2 binding to Activin is by FRET (Jares-Erijman and Jovin, 2003, Nat Biotechnol 21:1387-1395). This method consists in the energy transfer between two fluorescent dyes that are bound to two proteins, in this case Activin and TMEFF2. If Activin and TMEFF2 are bound together, the attached dyes transfer energy in such a way that one of the dyes absorbs the energy of the other and this produces an increase in the amount of fluorescence emitted by the acceptor dye. For example, one application of this principle is the Alphascreen platform. Alphascreen donor beads could be attached to Activin and Alphascreen acceptor beads could be attached to TMEFF2 or vice versa. The donor beads are stimulated by UV light with a particular wavelength. The emission of the activated donor stimulates the acceptor beads, which emit light in a different wavelength and this emission can be recorded. The acceptor beads are not activated if TMEFF2 and Activin are not bound.

Yet another possibility to screen for compounds that bind to TMEFF2 would be by using a functional assay. Free Activin binds to the Activin receptors and this results in receptor activation, phosphorylation and Smad activation. Therefore, the dissociation between TMEFF2 and Activin can be measured by an increase of receptor or Smad phosphorylation as well as an increase of Smad transcriptional activity. The Smad transcriptional activity can be measured for example with a reporter construct having a sequence 12×CAGA(SEQ ID NO: 20) cloned in the enhancer region of a Luciferase reporter (as 20) described in details in Example 14).

The invention claimed is:

1. A method of treating depression in a patient comprising administering to the patient an effective amount of a pharmaceutical composition comprising an antibody antagonist of transmembrane protein with EGF-like and two follistatin-like domains 2 (TMEFF2) wherein TMEFF2 has an amino acid sequence, SEQ ID NO:2, encoded by the nucleic acid sequence, SEQ ID NO: 1.

2. The method of claim 1, wherein said pharmaceutical composition is administered in combination with a compound selected from the group consisting of: amitriptyline, amitriptyline oxide, desipramine, dibenzepin, dosulepin, doxepin, chloroimipramine, imipramine, nortriptyline, mianserin, maprotiline, trimipramine, elzasonan, MK-869, DOV-216303, DOV-21947, licarbazepine, amfebutamone, radafaxine, vilazodone, GSK-679769, GW-597599, NS-2359, pramipexole, duloxetine, atomoxetine, desvenlafaxine, escitalopram, LU-AA21004, saredutant, SR-58611, SSR-149415, SSR-146977, moclobemide, Org-34517 Org-34850, ONO-2333Ms, NBI-34041, PD-171729, SSR-125543 viloxazine, trazodone, nefazodone, mirtazapine, venlafaxine, reboxetine, tranylcypromine, brofaromine, moclobemide, citalopram, paroxetine, fluoxetine, fluvoxamine, sertraline, Hypericum (St. John's Wort), alprazolam, clonazepam, diazepam, lorazepam, halazepam, chlordiazepoxide, buspirone, clonidine, pagoclone, risperidone, olanzapine, quetiapine, ziprasidone, and celecoxib.

3. The method of claim 1, wherein said pharmaceutical composition is administered in combination with a compound selected from the group consisting of: amitriptyline, amitriptyline oxide, desipramine, dibenzepin, dosulepin, doxepin, chloroimipramine, imipramine, nortriptyline, mianserin, maprotiline, trimipramine, DOV-21947, amfebutamone, vilazodone, GSK-679769, GW-597599, pramipexole, duloxetine, atomoxetine, desvenlafaxine, escitalopram, LU-AA21004, saredutant, SSR-149415, moclobemide, Org-34517, ONO-2333Ms, SSR-125543, viloxazine, trazodone, nefazodone, mirtazapine, venlafaxine, reboxetine, tranylcypromine, brofaromine, citalopram, paroxetine, fluoxetine, fluvoxamine, sertraline, Hypericum (St. John's Wort), alprazolam, clonazepam, diazepam, lorazepam, halazepam, chlordiazepoxide, buspirone, clonidine, pagoclone, risperidone, olanzapine, quetiapine, and ziprasidone.

* * * * *

SEQUENCE LISTING

<160> NUMBER OF SEQ ID NOS: 20

<210> SEQ ID NO 1
<211> LENGTH: 1627
<212> TYPE: DNA
<213> ORGANISM: Homo sapiens
<220> FEATURE:
<223> OTHER INFORMATION: TMEFF2 human

<400> SEQUENCE: 1

| cagtagcccg | ctgcccggcc | cccgcgatcc | tgtgttcctc | ggaagccgtt | tgctgctgca | 60 |
| gagttgcacg | aactagtcat | ggtgctgtgg | gagtccccgc | ggcagtgcag | cagctggaca | 120 |
| ctttgcgagg | gcttttgctg | gctgctgctg | ctgcccgtca | tgctactcat | cgtagcccgc | 180 |
| ccggtgaagc | tcgctgcttt | ccctacctcc | ttaagtgact | gccaaacgcc | caccggctgg | 240 |
| aattgctctg | gttatgatga | cagagaaaat | gatctcttcc | tctgtgacac | caacacctgt | 300 |
| aaatttgatg | gggaatgttt | aagaattgga | gacactgtga | cttgcgtctg | tcagttcaag | 360 |
| tgcaacaatg | actatgtgcc | tgtgtgtggc | tccaatgggg | agagctacca | gaatgagtgt | 420 |
| tacctgcgac | aggctgcatg | caaacagcag | agtgagatac | ttgtggtgtc | agaaggatca | 480 |
| tgtgccacag | atgcaggatc | aggatctgga | gatggagtcc | atgaaggctc | tggagaaact | 540 |
| agtcaaaagg | agacatccac | ctgtgatatt | tgccagtttg | gtgcagaatg | tgacgaagat | 600 |
| gccgaggatg | tctggtgtgt | gtgtaatatt | gactgttctc | aaaccaactt | caatcccctc | 660 |
| tgcgcttctg | atgggaaatc | ttatgataat | gcatgccaaa | tcaagaagc | atcgtgtcag | 720 |
| aaacaggaga | aaattgaagt | catgtctttg | ggtcgatgtc | aagataacac | aactacaact | 780 |
| actaagtctg | aagatgggca | ttatgcaaga | acagattatg | cagagaatgc | taacaaatta | 840 |
| gaagaaagtg | ccagagaaca | ccacataccct | tgtccggaac | attacaatgg | cttctgcatg | 900 |
| catgggaagt | gtgagcattc | tatcaatatg | caggagccat | cttgcaggtg | tgatgctggt | 960 |
| tatactggac | aacactgtga | aaaaaaggac | tacagtgttc | tatacgttgt | tcccggtcct | 1020 |
| gtacgatttc | agtatgtctt | aatcgcagct | gtgattggaa | caattcagat | tgctgtcatc | 1080 |
| tgtgtggtgg | tcctctgcat | cacaaggaaa | tgccccagaa | gcaacagaat | tcacagacag | 1140 |
| aagcaaaata | cagggcactg | tgggtataat | actaagttga | gatgatatca | tttacgggg | 1200 |
| aaggcgcttt | gtgaagtagg | ccttatttct | cttgtccttt | cgtacaggga | ggaatttgaa | 1260 |
| gtagatagaa | accgacctgg | attactccgg | tctgaactca | gatcacgtag | gactttaatc | 1320 |
| gttgaacaaa | cgaaccttta | atagcggctg | caccatcggg | atgtcctgat | ccaacatcga | 1380 |
| ggtcgtaaac | cctattgttg | atatggactc | tagaatagga | ttgcgctgtt | atccctaggg | 1440 |
| taacttgttc | cgttggtcaa | gttattggat | caattgagta | tagtagttcg | ctttgactgg | 1500 |
| tgaagtctta | gcatgtactg | ctcggaggtt | gggttctgct | ccgaggtcgc | cccaaccgaa | 1560 |
| atttttaatg | caggtttggt | agtttaggac | ctgtgggttt | gttaggtact | gtttgcatta | 1620 |
| ataaatt | | | | | | 1627 |

<210> SEQ ID NO 2
<211> LENGTH: 368
<212> TYPE: PRT
<213> ORGANISM: Homo sapiens
<220> FEATURE:
<223> OTHER INFORMATION: TMEFF2 human

<400> SEQUENCE: 2

Met Val Leu Trp Glu Ser Pro Arg Gln Cys Ser Ser Trp Thr Leu Cys
1               5                   10                  15

Glu Gly Phe Cys Trp Leu Leu Leu Pro Val Met Leu Leu Ile Val
            20                  25                  30

Ala Arg Pro Val Lys Leu Ala Ala Phe Pro Thr Ser Leu Ser Asp Cys
        35                  40                  45

Gln Thr Pro Thr Gly Trp Asn Cys Ser Gly Tyr Asp Asp Arg Glu Asn
    50                  55                  60

Asp Leu Phe Leu Cys Asp Thr Asn Thr Cys Lys Phe Asp Gly Glu Cys
65                  70                  75                  80

Leu Arg Ile Gly Asp Thr Val Thr Cys Val Gln Phe Lys Cys Asn
                85                  90                  95

Asn Asp Tyr Val Pro Val Cys Gly Ser Asn Gly Glu Ser Tyr Gln Asn
            100                 105                 110

Glu Cys Tyr Leu Arg Gln Ala Ala Cys Lys Gln Ser Glu Ile Leu
            115                 120                 125

Val Val Ser Glu Gly Ser Cys Ala Thr Asp Ala Gly Ser Gly Ser Gly
    130                 135                 140

Asp Gly Val His Glu Gly Ser Gly Glu Thr Ser Gln Lys Glu Thr Ser
145                 150                 155                 160

Thr Cys Asp Ile Cys Gln Phe Gly Ala Glu Cys Asp Glu Asp Ala Glu
                165                 170                 175

Asp Val Trp Cys Val Cys Asn Ile Asp Cys Ser Gln Thr Asn Phe Asn
            180                 185                 190

Pro Leu Cys Ala Ser Asp Gly Lys Ser Tyr Asp Asn Ala Cys Gln Ile
            195                 200                 205

Lys Glu Ala Ser Cys Gln Lys Gln Glu Lys Ile Glu Val Met Ser Leu
    210                 215                 220

Gly Arg Cys Gln Asp Asn Thr Thr Thr Thr Lys Ser Glu Asp Gly
225                 230                 235                 240

His Tyr Ala Arg Thr Asp Tyr Ala Glu Asn Ala Asn Lys Leu Glu Glu
                245                 250                 255

Ser Ala Arg Glu His His Ile Pro Cys Pro Glu His Tyr Asn Gly Phe
            260                 265                 270

Cys Met His Gly Lys Cys Glu His Ser Ile Asn Met Gln Glu Pro Ser
        275                 280                 285

Cys Arg Cys Asp Ala Gly Tyr Thr Gly Gln His Cys Glu Lys Lys Asp
        290                 295                 300

Tyr Ser Val Leu Tyr Val Pro Gly Pro Val Arg Phe Gln Tyr Val
305                 310                 315                 320

Leu Ile Ala Ala Val Ile Gly Thr Ile Gln Ile Ala Val Ile Cys Val
                325                 330                 335

Val Val Leu Cys Ile Thr Arg Lys Cys Pro Arg Ser Asn Arg Ile His
            340                 345                 350

Arg Gln Lys Gln Asn Thr Gly His Cys Gly Tyr Asn Thr Lys Leu Arg
        355                 360                 365

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctgatgggaa atcttatgat aatg                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 4
caggaacaac gtagagaaca ctgt                                          24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 5
acggggtcac ccacactgtg c                                             21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 6
ctagaagcat ttgcggtgga cgatg                                         25

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 7
atggtgaagg tcggtgtgaa cg                                            22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 8
gttgtcatgg atgaccttgg c                                             21

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 9
ucagaaggau ccugugcua                                                19

```
<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cgguuacgau gacagagaa                                                   19

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgatgggaa atcttatgat aatg                                             24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caggaacaac gtagagaaca ctgt                                             24

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acggggtcac ccacactgtg c                                                21

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctagaagcat ttgcggtgga cgatg                                            25

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
cgcguagaag augaaguugt t                                                21
```

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ucagaaggau ccugugcua                                                  19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
cgguuacgau gacagagaa                                                  19

<210> SEQ ID NO 18
<211> LENGTH: 2175
<212> TYPE: DNA
<213> ORGANISM: Homo sapiens

<400> SEQUENCE: 18
agtacagtat aaaacttcac agtgccaata ccatgaagag gagctcagac agctcttacc     60
acatgataca agagccggct ggtggaagag tggggaccag aaagagaatt tgctgaagag    120
gagaaggaaa aaaaaaacac caaaaaaaaa aataaaaaaa tccacacaca caaaaaaacc    180
tgcgcgtgag gggggaggaa aagcagggcc ttttaaaaag gcaatcacaa caacttttgc    240
tgccaggatg cccttgcttt ggctgagagg atttctgttg gcaagttgct ggattatagt    300
gaggagttcc cccaccccag gatccgaggg gcacagcgcg gcccccgact gtccgtcctg    360
tgcgctggcc gccctcccaa aggatgtacc caactctcag ccagagatgg tggaggccgt    420
caagaagcac attttaaaca tgctgcactt gaagaagaga cccgatgtca cccagccggt    480
acccaaggcg gcgcttctga acgcgatcag aaagcttcat gtgggcaaag tcggggagaa    540
cggggtatgt gagatagagg atgacattgg aaggagggca gaaatgaatg aacttatgga    600
gcagacctcg gagatcatca cgtttgccga gtcaggaaca gccaggaaga cgctgcactt    660
cgagatttcc aaggaaggca gtgacctgtc agtggtggag cgtgcagaag tctggctctt    720
cctaaaagtc cccaaggcca acaggaccag gaccaaagtc accatccgcc tcttccagca    780
gcagaagcac ccgcagggca gcttggacac aggggaagag gccgaggaag tgggcttaaa    840
gggggagagg agtgaactgt tgctctctga aaaagtagta gacgctcgga gagcacctg    900 gcatgtcttc cctgtctcca gcagcatcca gcggttgctg gaccagggca gagctccct    960 ggacgttcgg attgcctgtg agcagtgcca ggagagtggc gccagcttgg ttctcctggg   1020
caagaagaag aagaaagaag aggagggga agggaaaaag aagggcggag gtgaaggtgg   1080
ggcaggagca gatgaggaaa aggagcagtc gcacagacct ttcctcatgc tgcaggcccg   1140
gcagtctgaa gaccaccctc atcgccggcg tcggcggggc ttggagtgtg atggcaaggt   1200
caacatctgc tgtaagaaac agttctttgt cagtttcaag gacatcggct ggaatgactg   1260
gatcattgct ccctctggct atcatgccaa ctactgcgag ggtgagtgcc cgagccatat   1320
agcaggcacg tccgggtcct cactgtcctt ccactcaaca gtcatcaacc actaccgcat   1380

```
gcggggccat agccccttg ccaacctcaa atcgtgctgt gtgcccacca agctgagacc    1440
catgtccatg ttgtactatg atgatggtca aacatcatc aaaaaggaca ttcagaacat    1500
gatcgtggag gagtgtgggt gctcatagag ttgcccagcc caggggggaaa gggagcaaga  1560 gttgtccaga gaagacagtg gcaaaatgaa gaaattttta aggtttctga gttaaccaga   1620
aaaatagaaa ttaaaaacaa aacaaaaaaa aaaacaaaaa aaaacaaaag taaattaaaa   1680
acaaaacctg atgaaacaga tgaaggaaga tgtggaaaaa atccttagcc agggctcaga   1740
gatgaagcag tgaaagagac aggaattggg agggaaaggg agaatggtgt acccttattt   1800
tcttctgaaa tcacactgat gacatcagtt gtttaaacgg ggtattgtcc tttccccct    1860 tgaggttccc ttgtgagcct tgaatcaacc aatctagtct gcagtagtgt ggactagaac   1920
aacccaaata gcatctagaa agccatgagt ttgaagggc ccatcacagg cactttccta    1980
cccaattacc caggtcataa ggtatgtctg tgtgacactt atctctgtgt atatcagcat   2040
acacacacac acacacacac acacacacac acacaggcat ttccacacat tacatatata   2100
cacatactgg taaaagaaca atcgtgtgca ggtggtcaca cttccttttt ctgtaccact   2160
tttgcaacaa aacaa                                                    2175
```

<210> SEQ ID NO 19
<211> LENGTH: 426
<212> TYPE: PRT
<213> ORGANISM: Homo sapiens

<400> SEQUENCE: 19

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
```

```
                225                 230                 235                 240
Arg Ile Ala Cys Glu Gln Cys Gln Glu Ser Gly Ala Ser Leu Val Leu
                    245                 250                 255

Leu Gly Lys Lys Lys Lys Glu Glu Glu Gly Glu Gly Lys Lys Lys
                260                 265                 270

Gly Gly Gly Glu Gly Gly Ala Gly Ala Asp Glu Glu Lys Glu Gln Ser
                275                 280                 285

His Arg Pro Phe Leu Met Leu Gln Ala Arg Gln Ser Glu Asp His Pro
        290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
                340                 345                 350

Glu Cys Pro Ser His Ile Ala Gly Thr Ser Gly Ser Ser Leu Ser Phe
                355                 360                 365

His Ser Thr Val Ile Asn His Tyr Arg Met Arg Gly His Ser Pro Phe
        370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
                420                 425

<210> SEQ ID NO 20
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cagacagaca gacagacaga cagacagaca gacagacaga cagacaga                    48
```